US007897338B2

(12) United States Patent
Woo et al.

(10) Patent No.: US 7,897,338 B2
(45) Date of Patent: *Mar. 1, 2011

(54) MOBILITY-MODIFIED NUCLEOBASE POLYMERS AND METHODS OF USING SAME

(75) Inventors: Sam Lee Woo, Redwood City, CA (US); Ronald J. Graham, San Ramon, CA (US); Jing Tian, Mountain View, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/456,836

(22) Filed: Jul. 11, 2006

(65) Prior Publication Data

US 2007/0026434 A1    Feb. 1, 2007

Related U.S. Application Data

(62) Division of application No. 10/856,752, filed on May 28, 2004, now Pat. No. 7,074,569, which is a division of application No. 09/836,704, filed on Apr. 16, 2001, now Pat. No. 6,743,905.

(51) Int. Cl.
*C12Q 1/68* (2006.01)
*C07H 21/00* (2006.01)
*C07H 21/02* (2006.01)

(52) U.S. Cl. .......................... 435/6; 536/23.1; 536/25.3; 536/26.6

(58) Field of Classification Search ....................... None
See application file for complete search history.

(56) References Cited

U.S. PATENT DOCUMENTS

| | | | |
|---|---|---|---|
| 4,914,210 A | 4/1990 | Levenson et al. | |
| 5,185,444 A | 2/1993 | Summerton et al. | |
| 5,470,705 A | 11/1995 | Grossman et al. | |
| 5,470,967 A | 11/1995 | Huie et al. | |
| 5,470,974 A | 11/1995 | Summerton et al. | |
| 5,514,543 A | 5/1996 | Grossman et al. | |
| 5,580,732 A | 12/1996 | Grossman et al. | |
| 5,624,800 A | 4/1997 | Grossman et al. | |
| 5,703,222 A | 12/1997 | Grossman et al. | |
| 5,777,096 A | 7/1998 | Grossman et al. | |
| 5,807,682 A | 9/1998 | Grossman et al. | |
| 6,013,785 A | 1/2000 | Bruice et al. | |
| 6,063,569 A | 5/2000 | Gildea et al. | |
| 6,087,325 A | 7/2000 | Meers et al. | |
| 6,143,716 A | 11/2000 | Meers et al. | |
| 6,339,069 B1 | 1/2002 | Meers et al. | |
| 6,395,486 B1 | 5/2002 | Grossman | |
| 6,743,905 B2 * | 6/2004 | Woo et al. | 536/23.1 |
| 7,074,569 B2 * | 7/2006 | Woo et al. | 435/6 |

FOREIGN PATENT DOCUMENTS

| | | | |
|---|---|---|---|
| CA | 2 443 122 A1 | 10/2003 | |
| EP | 1 379 698 B1 | 8/2009 | |
| WO | WO 93/20236 A1 | 10/1993 | |
| WO | WO 93/20239 A1 | 10/1993 | |
| WO | WO 02/083954 A1 | 10/2002 | |

OTHER PUBLICATIONS

Stratagene catalog, 1998, p. 39.*
Herdewijn et al., "Nucleotides (Part XXXII), Synthesis of 2'-5' Connected Oligonucleotides. Prodrugs for Antiviral and Antitumoral Nucleosides" Helvetica Chimica Acta, vol. 72, No. 8, 1989, pp. 1739-1748.
W. Kuijpers et al., "A New Strategy for the Solid-Phase Synthesis of 5'-Thiolated Oligodeoxynucleotides" Tetrahedron, Elsevier Science Publishers, Amsterdam, NL, vol. 49, No. 47, Nov. 19, 1993, pp. 10931-10944.
B. Seelig et al., "Site-specific Modification of Enzymatically Synthesized RNA: Transcription Initiation and Diels-Alder Reaction",Tetrahedron Letters, Elsevier, Amsterdam, NL, vol. 38, No. 44, Nov. 3, 1997, pp. 7729-7732.
B. Connolly, "Solid Phase 5' Phosphorylation of Oligonucleotides" Tetrahedron Letters, vol. 28, No. 4, 1987, pp. 463-466.
L. Mizrakh et al., "Reactions of Alkyl Tetraalkylphosphorodiamidites with N-(hydroxyethyl)Acetamide" J. Gen. Chem. USSR, vol. 45, 1975, p. 2301.
J. Verheijen et al, "2',5'-Oligoadenylate-Peptide Nucleic Acids (2-5A-PNAS) Activate RNASE L" Bioorganic & Medicinal Chemistry, Elsevier Science LTD, GB, vol. 7, 1999, pp. 449-455.
S. Rumney et al., "Structural Optimisation of Non-Nucleotide Loop Replacements for Duplex and Triplex DNAs" J. Am. Chem. Soc., vol. 117, 1995, pp. 5637-5646.
Supplementary European Search Report dated Mar. 14, 2007 cited in EP Application No. 02731376.6, 4 pages.
English version of Abstract for Japanese Patent Publication No. JP 4452445 B2, of Issue Date Apr. 21, 2010, based upon the Abstract for corresponding publication WO02/083954.
English translation of Abstract for Japanese Patent Publication No. JP2009240332 (A), published on Oct. 22, 2009.
Official Communication from the European Patent Office, dated Aug. 29, 2007, for EP Application No. 02 731 376.8.
Official Communication from the European Patent Office, dated Mar. 6, 2008, for EP Application No. 02 731 376.8.
English translation of the Japanese Patent Office's Notice of Reasons for Rejection for Application No. 2002-581693, dated Jan. 30, 2009.

* cited by examiner

*Primary Examiner* — Mark Staples

(57) ABSTRACT

The present invention relates generally to nucleobase polymer functionalizing reagents, to mobility-modified sequence-specific nucleobase polymers, to compositions comprising a plurality of mobility-modified sequence-specific nucleobase polymers, and to the use of such polymers and compositions in a variety of assays, such as, for example, for the detection of a plurality of selected nucleotide sequences within one or more target nucleic acids. The mobility-modifying polymers of the present invention include phosphoramidite reagents which can be joined to other mobility-modifying monomers and to sequence-specific oligonucleobase polymers via uncharged phosphate triester linkages. Addition of the mobility-modifying phosphoramidite reagents of the present invention to oligonucleobase polymers results in unexpectedly large effects the mobility of those modified oligonucleobase polymers, especially upon capillary electrophoresis in non-sieving media.

32 Claims, No Drawings

```
                       SEQUENCE LISTING

<160> NUMBER OF SEQ ID NOS: 12

<210> SEQ ID NO 1
<211> LENGTH: 8
<212> TYPE: DNA
<213> ORGANISM: Artificial
<220> FEATURE:
<223> OTHER INFORMATION: Synthetic DNA

<400> SEQUENCE: 1 atgcatgc                                                        8

<210> SEQ ID NO 2
<211> LENGTH: 8
<212> TYPE: DNA
<213> ORGANISM: Artificial
<220> FEATURE:
<223> OTHER INFORMATION: Synthetic DNA

<400> SEQUENCE: 2 atgcatgc                                                        8

<210> SEQ ID NO 3
<211> LENGTH: 9
<212> TYPE: DNA
<213> ORGANISM: Artificial
<220> FEATURE:
<223> OTHER INFORMATION: Synthetic DNA

<400> SEQUENCE: 3 cgtacgtat                                                       9

<210> SEQ ID NO 4
<211> LENGTH: 15
<212> TYPE: DNA
<213> ORGANISM: Artificial
<220> FEATURE:
<223> OTHER INFORMATION: Synthetic DNA

<400> SEQUENCE: 4
gggacggggt tcagc                                               15

<210> SEQ ID NO 5
<211> LENGTH: 15
<212> TYPE: DNA
<213> ORGANISM: Artificial
<220> FEATURE:
<223> OTHER INFORMATION: Synthetic DNA

<400> SEQUENCE: 5
gggacggggt tcagc                                               15
```

<210> SEQ ID NO 6
<211> LENGTH: 15
<212> TYPE: DNA
<213> ORGANISM: Artificial
<220> FEATURE:
<223> OTHER INFORMATION: Synthetic DNA

<400> SEQUENCE: 6
gggacggggt tcagc                                                    15

<210> SEQ ID NO 7
<211> LENGTH: 20
<212> TYPE: DNA
<213> ORGANISM: Artificial
<220> FEATURE:
<223> OTHER INFORMATION: Synthetic DNA

<400> SEQUENCE: 7
gagtctccgg gtcagaatga                                               20

<210> SEQ ID NO 8
<211> LENGTH: 20
<212> TYPE: DNA
<213> ORGANISM: Artificial
<220> FEATURE:
<223> OTHER INFORMATION: Synthetic DNA

<400> SEQUENCE: 8
tctcggtttc ttctccatcg                                               20

<210> SEQ ID NO 9
<211> LENGTH: 26
<212> TYPE: DNA
<213> ORGANISM: Artificial
<220> FEATURE:
<223> OTHER INFORMATION: Synthetic DNA

<400> SEQUENCE: 9
gaggcaatag tttttgaggg gcatgt                                        26

<210> SEQ ID NO 10
<211> LENGTH: 15
<212> TYPE: DNA
<213> ORGANISM: Artificial
<220> FEATURE:
<223> OTHER INFORMATION: Synthetic DNA

<400> SEQUENCE: 10
gggacggggt tcagc                                                    15

<210> SEQ ID NO 11
<211> LENGTH: 15
<212> TYPE: DNA
<213> ORGANISM: Artificial
<220> FEATURE:
<223> OTHER INFORMATION: Synthetic DNA

<400> SEQUENCE: 11
gggacggggt tcagc                                                    15

<210> SEQ ID NO 12
<211> LENGTH: 15
<212> TYPE: DNA
<213> ORGANISM: Artificial
<220> FEATURE:
<223> OTHER INFORMATION: Synthetic DNA -continued

<400> SEQUENCE: 12
gggacggggt tcagc                    15

MOBILITY-MODIFIED NUCLEOBASE POLYMERS AND METHODS OF USING SAME

1. CROSS REFERENCE OF THE RELATED APPLICATIONS

This application is a divisional of U.S. application Ser. No. 10/856,752, filed May 28, 2004 (now U.S. Pat. No. 7,074, 569), which is a divisional of U.S. application Ser. No. 09/836,704, filed Apr. 16, 2001 (now U.S. Pat. No. 6,743, 905), all of which are incorporated herein by reference.

2. FIELD OF THE INVENTION

The present invention relates generally to nucleobase polymer functionalizing reagents, to mobility-modified sequence-specific nucleobase polymers, to compositions comprising a plurality of mobility-modified sequence-specific nucleobase polymers, and to the use of such polymers and compositions in a variety of assays, such as, for example, for the detection of a plurality of selected nucleotide sequences within one or more target nucleic acids.

3. BACKGROUND OF THE INVENTION

Methods used to detect selected nucleotide sequences within target nucleic acids underlie an extensive array of practical applications including, but not limited to, paternity testing, forensic analysis, organ donor recipient matching, disease diagnosis, prognosis and treatment, and prenatal counseling.

There exists a need in the art for materials and methods that permit pluralities of selected nucleotide sequences to be simultaneously detected and analyzed, under uniform experimental conditions, preferably in a single, automated, assay reaction. One approach towards meeting this need has been the development of mobility-modifying polymers that can be attached to sequence-specific nucleobase polymers that act to increase the effective size of the modified nucleobase polymers. Where the charge to translational frictional drag ratio of the mobility-modifying polymer differs from that of the nucleobase polymer to which it is attached, the resulting modified nucleobase polymer will have an electrophoretic mobility that differs from that of the unmodified nucleobase polymer. This alteration of the charge to translational frictional drag ratio may be employed in various applications to effect electrophoretic separation of similarly-sized nucleobase polymers under both sieving and non-sieving conditions.

The most commonly employed mobility-modifying polymers are polyethylene oxides (PEO) that are attached to a nucleobase polymer using standard DNA chemistry (Grossman et al. (1994) *Nucleic Acids Research* 22 (21): 4527-34). An exemplary standard PEO phosphoramidite reagent ("PEO reagent") that can be added to a nucleobase polymer using standard DNA chemistry is illustrated below:

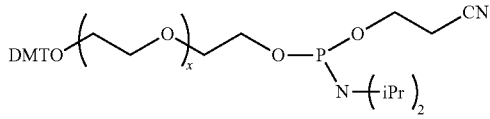

In the illustration, DMT represents dimethoxytrityl and iPr represents isopropyl. When x=5, each PEO reagent added to the nucleobase polymer imparts the nucleobase polymer with an electrophoretic retardation of approximately 2 nucleotides as compared to the unmodified nucleobase polymer under both sieving and nonsieving electrophoretic conditions. Due to limitations of DNA chemistry, no more than about 40 PEO reagents can be coupled to a nucleobase polymer and result in homogenous product. Accordingly, the greatest electrophoretic mobility retardation that can be achieved using these standard PEO modifying reagents is about 80 nucleotides.

However, in light of the increasing need to simultaneously analyze vast numbers of nucleotide sequences in a single experiment, e.g., the 200 identified alleles associated with cystic fibrosis, there remains a need in the art for new mobility-modifying polymers that have different charge to translational frictional drag ratios than currently available mobility-modifying polymers, and that can impart electrophoretic mobility retardations of greater than the 80 nucleotides achievable with available PEO modifying reagents. The availability of such new mobility-modifying polymers would greatly increase the repertoire of available mobility modifications, thereby enabling the ability to perform extremely complex sequence analyses in simple, preferably automated, formats.

4. SUMMARY OF THE INVENTION

In one aspect, the present invention provides mobility-modifying phosphoramidite functionalizing reagents comprising a polymeric portion and a phosphoramidite moiety. The phosphoramidite moiety comprises an oxygen-protecting group that, quite unlike the β-cyanoethyl oxygen protecting group used in conventional phosphoramidite reagents, is stable to basic conditions such as the conditions and reagents used in conventional phosphoramidite oligonucleotide synthesis and deprotection. As a consequence of this stable oxygen protecting group, the bond formed between the functionalizing reagent and the compound functionalized is an uncharged phosphate triester. The mobility-modifying phosphoramidite reagents of the invention may be used to functionalize a wide variety of substances and materials to add mass and size to the substance or material without substantially altering its overall net charge.

The mobility-modifying phosphoramidite reagents of the invention are compatible with standard phosphoramidite synthetic schemes and can be used with commercially available nucleobase polymer synthesis instruments. Thus, the mobility-modifying phosphoramidite reagents of the present invention are particularly convenient for mobility-modifying synthetic sequence-specific nucleobase polymers such as, for example, 2'-deoxyoligonucleotides. They may be readily attached to the 5'-terminus of the nucleobase polymer, to the 3'-terminus, or to both the 5'- and 3'-termini, depending on the particular application and/or desired degree of mobility modification.

The terminus of the polymeric portion that is distal to the phosphoramidite moiety may be protected with a group that is selectively removable under the desired synthesis conditions, or it may comprise a group that is essentially non-reactive, such as, for example an alkyl, aryl, arylakyl, etc. group. In the former embodiment, the protecting group may be selectively removed for sequential condensation of one or more additional phosphoramidite reagents. Suitable selectively removable protecting groups will depend upon the identity of the group being protected and will be apparent to those of skill in the art. Selectively removable groups suitable for protecting hydroxyl groups include, by way of example and not limitation, any of the acid-labile groups that are commonly used to protect the 5'-hydroxyl of conventional nucleoside phosphoramidites oligonucleotide synthesis reagents, such as acid-labile trityl groups (e.g., monomethoxytrityl, dimethoxytrityl, etc.).

The mobility-modifying phosphoramidite reagents of the invention may be used alone to mobility-modify substances such as nucleobase polymers to add mass and size to the nucleobase polymer without altering its overall net charge. Alternatively, they may be used in conjunction with conventional mobility-modifying reagents, such as the PEO reagent illustrated above, to mobility-modify substances such as nucleobase polymers. Because the mobility-modifying phosphoramidite reagents of the invention may be used to add mass and size to a substance such as a nucleobase polymer without altering its overall charge, when used in conjunction with conventional reagents such as PEO reagents, they vastly increase the repertoire of available mobility-modifications that can be added to substances such as nucleobase polymers.

The polymeric portion composing the reagent may be any of a variety of polymers that are soluble under the desired conditions of use and that either include, or can be modified to include, a functional group, such as, for example, a primary hydroxyl group, that can be conveniently converted to a phosphoramidite moiety, typically using standard art-known chemistries. Typical polymers include, but are not limited to, polyoxides, polyamides, polyimines and polysaccharides. The polymers may be used singly or in combinations, such as in the form of copolymers or block polymers. Exemplary polymers include linear or branched polyalkylene oxides, or derivatives thereof, comprising from about 2 to 10 monomer units. Typical derivatives include, for example, those in which the terminal hydroxyl is replaced with a sulfanyl group or an amino group. A useful polyalkylene oxide polymer is polyethylene glycol. The polymer may optionally include a label or other reporter group or molecule, a protecting group for protecting the mobility-modified nucleobase polymer during subsequent synthesis reactions, or other groups for, e.g., binding the mobility-modified nucleobase polymer to other moieties or chemical species, such as, e.g., ligands, etc.

As discussed above, the group protecting the phosphoramidite oxygen atom of the reagents of the invention is stable to the basic conditions used to deprotect and/or cleave synthetic nucleobase polymers such as oligonucleotides. Thus, the oxygen protecting group should generally be stable to treatment with ammonium hydroxide at a temperature of 55° C. for a period of about 18 hrs. Of course, if milder deprotection and/or cleavage conditions are used, the oxygen protecting group need only be stable to these milder conditions. Groups stable to such basic conditions that can be used to protect the oxygen atom of the phosphoramidite reagents of the invention will be apparent to those of skill in the art, and include by way of example and not limitation, alkyls comprising at least two carbon atoms, aryls and $(R^8)_3Si-$ where each $R^8$ is independently selected from the group consisting of linear and branched chain alkyl and aryl. Alternatively, the oxygen protecting group may be a polymer segment, optionally having a selectively removable terminal protecting group as described above. In this latter embodiment, the reagents of the invention permit the formation of mobility-modified substances comprising branched or dendritic polymer segments.

In one convenient embodiment, the polymer portion of the mobility-modifying phosphoramidite reagents of the present invention is a polyalkylene oxide, an illustrative embodiment of which is depicted as Formula (I) below:

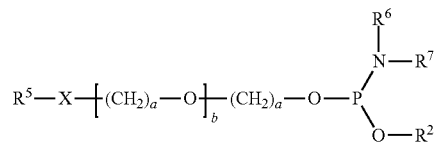

wherein:
$R^5$ is selected from the group consisting of hydrogen, protecting group, reporter molecule, and ligand;
X is selected from the group consisting of O, S, NH, and NH—C(O);
each a is, independently, an integer from 1 to 6;
b is an integer from 0 to 40;
$R^6$ and $R^7$ are each independently selected from the group consisting of $C_1$-$C_6$ alkyl, $C_3$-$C_{10}$ cycloalkyl, $C_6$-$C_{20}$ aryl, and $C_{20}$-$C_{27}$ arylalkyl; and
$R^2$ is selected from the group consisting of alkyl comprising at least two carbon atoms, aryl, $(R^8)_3$ Si— where each $R^8$ is independently selected from the group consisting of linear and branched chain alkyl and aryl, base-stable protecting groups, and $R^5$—X—$[(CH_2)_a$—O$]_b$—$(CH_2)_a$—.

In another aspect, the present invention provides sequence-specific nucleobase polymers that have been mobility-modified with the mobility-modifying phosphoramidite reagents of the invention, either alone or in combination with conventional mobility-modified reagents. Such sequence-specific mobility-modified nucleobase polymers generally comprise a mobility-modifying polymeric segment and a sequence-specific nucleobase segment.

The nucleobase polymer segment is typically an oligonucleotide such as a DNA oligomer or an RNA oligomer, but may also be any of a number of different analogs or derivatives of DNA and/or RNA, as will be described in more detail in a later section. The nucleobase polymer has a sequence of nucleobases that is at least partially complementary to a desired nucleotide sequence of a target nucleic acid such that the nucleobase polymer segment specifically binds the target sequence, under specified conditions.

The mobility-modifying polymer segment has a ratio of charge-to-translational frictional drag that is different from that of the nucleobase polymer segment in a given electrophoretic medium. Consequently by virtue of the mobility-modifying polymer segment, the mobility-modified sequence-specific nucleobase polymers of the invention have electrophoretic mobilities that are retarded as compared with those of the corresponding unmodified nucleobase polymer.

According to one illustrative embodiment of the invention, the mobility-modified sequence-specific nucleobase polymer is a compound according to structural formula (II):

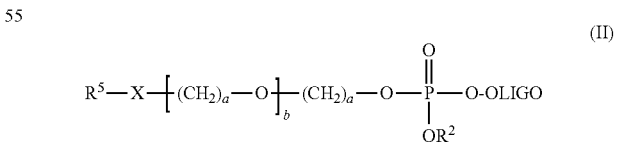

or a salt thereof, wherein:
$R^2$, $R^5$, X, a, and b are as in Formula (I); and
OLIGO is a sequence-specific nucleobase polymer comprising at least five nucleobases.

The mobility-modifying polymer can be attached to the 5'-end, the 3'-end, or both the 5'-end and the 3'-end of the OLIGO. The mobility-modifying polymer can also be attached to the 5'-end of a first nucleobase polymer and to the 3'-end of a second nucleobase polymer, thereby providing a mobility-modified oligonucleobase polymer having the mobility-modifying polymer segment linking two nucleobase polymer segments.

By virtue of substituent $R^2$ in the mobility-modified nucleobase polymers according to Formula (II), the illustrated phosphate triester is uncharged at physiological pH. The illustrated mobility-modifying polymeric group, therefore, would add only mass, and not charge, to the OLIGO.

The mobility-modified nucleobase polymer of the invention are not limited to those including only uncharged phosphate triester linkages. By judiciously selecting combinations of uncharged phosphate triester linkages and charged phosphate diester linkages, the repertoire of available mobility-modifications can be dramatically increased. Accordingly, in a second illustrative embodiment, the mobility-modified sequence-specific nucleobase polymer is a compound according to structural formula (III):

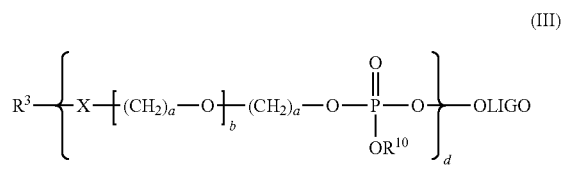

(III)

or a salt thereof, wherein:

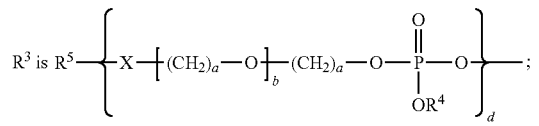

$R^2$, $R^5$, a, b, X, and OLIGO are as previously defined in Formulae (I) and (II);
each d is independently an integer from 1 to 200; and
each $R^4$ and each $R^{10}$ is independently selected from the group consisting of hydrogen and $R^2$, with the proviso that at least one $R^{10}$ or at least one $R^4$ is other than hydrogen.

In the compounds of structural formula (III), each a, b, d, X, $R^{10}$ and $R^4$ may, independently of one another, be the same or different. In certain embodiments of the compounds of structural formulae (III), at least some $R^{10}$ and/or $R^4$ are other than hydrogen. Where $R^{10}$ and $R^4$ are other than hydrogen, $R^{10}$ and/or $R^4$ are $R^2$.

In another embodiment, the present invention provides compositions comprising a plurality of mobility-modified sequence-specific nucleobase polymers of the invention, wherein, in certain embodiments, each said mobility-modified nucleobase polymer has a structure independently selected from the group consisting of structural formulae (II) and (III). At least two of the nobility-modified nucleobase polymers of the plurality has a distinctive ratio of charge to translational frictional drag such that each of the two or more mobility-modified nucleobase polymers has a distinct electrophoretic mobility. The distinctive ratios of charge to translational frictional drag may be due to differences in the lengths (i.e., the number of monomer units) of the mobility-modifying polymer segment of the molecule, differences in the number of mobility-modifying polymer segments attached to the nucleobase polymer (i.e., differences in: variable d in structural formulae (II) and (III)), the charges linking multiple mobility-modifying polymer segments, the number of charged versus uncharged subunits, the length and charge of the nucleobase polymer, or a combination of these features.

In yet another aspect, the present invention provides a method of detecting a plurality of nucleotide sequences within one or more target nucleic acids. According to the method, a plurality of mobility-modified sequence-specific nucleobase polymer probes, each of which optionally has a structure independently selected from the group consisting of structural formula (II) and (III), is contacted with one or more target nucleic acids, generally under conditions that distinguish those mobility-modified probes that hybridize to the target nucleic acid in a base-specific manner from those that do not. The mobility-modified nucleobase polymer probes that hybridize to the target are then fractionated by electrophoresis. The presence of selected sequence(s) in the target nucleic acid is detected according to the observed electrophoretic migration rates of the mobility-modified nucleobase polymer probes, or, optionally, according to the identity of a label or by a combination thereof.

The mobility-modified nucleobase polymer probes may be either labeled or unlabeled. Alternatively, they may be modified to include a label during the method, as well be described more fully below. When unlabeled, the electrophoretic migration rates of the mobility-modified probes may be monitored by conventional means, for example by absorbance spectroscopy. When labeled, for example with a fluorophore, the electrophoretic migration rates may be monitored by detecting the label.

In one embodiment of the present invention, in order to facilitate detection of the mobility-modified probes in a multiplex assay, the mobility-modified probes are labeled are labeled with different fluorescent labels such as, but not limited to, 5-carboxyfluorescein (5-FAM), 6-carboxy-fluorescein (6-FAM), 2',7'-dimethoxy-4',5'-dichloro-6-carboxyfluorescein (JOE), N,N,N'-N-tetramethyl-6-carboxy rhodamine (TAMRA), 6-carboxy-X-rhodamine (ROX), 4,7,2',4',5',7'-hexachloro-6-carboxy-fluorescein (HEX-1), 4,7,2',4',5', 7'-hexachloro-5-carboxy-fluorescein (HEX-2), 2',4',5',7'-tetrachloro-5-carboxy-fluorescein (ZOE), 4,7,2',7'-tetrachloro-6-carboxy-fluorescein (TET-1), 1',2',7',8'-dibenzo-4,7-dichloro-5-carboxyfluorescein (NAN-2), and 1',2',7', 8'-dibenzo-4,7-dichloro-6-carboxyfluorescein. Guidance for selecting appropriate fluorescent labels can be found in Smith et al. (1987) Meth. Enzymol. 155:260-301, Karger et al. (1991) Nucl. Acids Res. 19:4955-4962, Haugland (1989) Handbook of Fluorescent Probes and Research Chemicals (Molecular Probes, Inc., Eugene, Oreg.). Exemplary fluorescent labels include fluorescein and derivatives thereof, such as those disclosed in U.S. Pat. No. 4,318,846 to Khanna et al. and Lee et al. (1989) Cytometry 10:151-164, and 6-FAM, JOE, TAMA, ROX, HEX-1, HEX-2, ZOE, TET-1 or NAN-2, as described above, and the like. When a plurality of fluorescent dyes are employed, they should, in many cases be spectrally resolvable.

In one convenient embodiment of the method, the target nucleic acid(s) are immobilized on a solid support. Following hybridization, unhybridized probes are removed, typically by washing, and the hybridized probes are recovered, typically by denaturing the hybrids, and those recovered hybridized probes are fractionated by electrophoresis as described above.

In another embodiment of the method, mobility-modified probes that specifically hybridize to the target nucleic acid are modified to incorporate a label. The modification may be accomplished in numerous different ways, see, for example, U.S. Pat. Nos. 5,807,682, 5,703,222, and 5,470,705, which disclose methods and compositions useful for the selective modification of probes when bound to a target nucleic acid in a base-specific manner. In one general method a second sequence-specific nucleobase polymer probe which includes a detectable label is covalently joined to the hybridized mobility-modified probe. This second labeled probe may also optionally include a mobility-modifying polymer. The two probes can be covalently joined to one another when they both adjacently hybridize to the same target nucleic acid molecule (i.e., the probes have confronting terminal nucleobase residues that basepair with adjacent bases of the target nucleic acid). The covalent joining may be accomplished by chemical means or biological means, such as by a DNA or RNA ligase.

Thus, according to this aspect of the invention, the target nucleic acid(s), which may be in solution or immobilized, are contacted with a first plurality of nobility-modified sequence-specific nucleobase polymer probes according to the invention, each of which has a distinctive ratio of charge to translational frictional drag and is, optionally, selected from the group consisting of structural formula (II) and (III), and a second, labeled sequence-specific nucleobase polymer probe, generally under conditions that distinguish those probes that hybridize to the target in a sequence-specific maimer. Probes that adjacently hybridize to the same target nucleic acid molecule are then covalently joined together (ligated) to form a mobility-modified labeled ligation product. Each labeled ligation product has a distinctive ratio of charge to translational frictional drag. In a further aspect, three or more nucleobase polymer probes are hybridized to adjacent sequences of a target nucleic acid in such a maimer that at least three probes can be covalently joined to form a ligation product, wherein at least one of the probes so joined comprises a detectable label, and at least one of the probes so joined is a mobility-modified sequence-specific nucleobase polymer probe, optionally selected from the group consisting of structural formula (II) and (III) such that the ligation product bears a label and has a distinctive ratio of charge translational frictional drag. The labeled ligation products, which are hybridized to the target nucleic acid, are recovered and fractioned by electrophoresis, as described above.

This cycle of hybridization, joining, and denaturation, may be repeated in order to amplify the concentration of the ligation product formed. In this instance, the joining may be accomplished by means of a thermostable ligase. Furthermore, additional nucleobase polymer probes, which together are sufficiently complementary to the ligated product to hybridize thereto and be covalently joined to one another as above, are also included, thereby affording geometric amplification of the ligated product, i.e., a ligase chain reaction. The product of such a ligase chain reaction therefore is a double stranded molecule consisting of two strands, each of which is the product of the joining of at least two sequence-specific nucleobase polymer probes. Accordingly, in yet another aspect of the present invention, at least one of the sequence-specific nucleobase polymers incorporated within the ligase chain reaction product comprises a detectable label, and at one of the sequence-specific nucleobase polymers is a mobility-modified sequence-specific nucleobase polymer selected from the group consisting of structural formula (II) and (III) such that at least one strand of the ligase chain reaction product has a distinctive ratio of charge to translational frictional drag.

In a second general method, the modification is achieved via a template-directed fill-in reaction or via PCR. In this aspect, a target nucleic acid, which may be in solution or immobilized, is contacted with a plurality of sequence-specific nucleobase polymers probes, two of which hybridize to opposite ends of complementary strands flanking a nucleotide sequence of interest within the target nucleic acid. Repeated cycles of extension of the hybridized sequence-specific probes, optionally by a thermostable polymerase, thermal denaturation and dissociation of the extended product, and annealing, provide a geometric amplification of the region bracketed by the two nucleobase polymer probes. The product of such a polymerase chain reaction therefore is a double stranded molecule consisting of two strands, each of which comprises a sequence-specific nucleobase polymer probe. In this aspect of the present invention, at least one of the sequence-specific nucleobase polymer probes is a mobility-modified sequence-specific nucleobase polymer probe according to the invention, optionally a probe selected from the group consisting of structural formula (II) and (III), such that the double stranded polymerase chain reaction product has a distinctive ratio of charge to translational frictional drag. The polymerase chain reaction product formed in this aspect of the invention may further comprise a label, which may be incorporated within either of the sequence-specific nucleobase polymer probes used as primers, or it may be incorporated within the substrate deoxyribonucleoside triphosphates used by the polymerizing enzyme. In other instances, the polymerase chain reaction product may be labeled by intercalation with an intercalating dye or by other non-covalent association with a detectable indicator molecule. In yet another aspect, the polymerase chain reaction product formed is analyzed under denaturing conditions, providing separated single stranded products. In this aspect, at least one of the single stranded products comprises both a label and a mobility-modified sequence-specific nucleobase polymer of the invention, optionally selected from the group consisting of structural formula (II) and (III) such that the single stranded product derived from double stranded polymerase chain reaction product has a distinctive ratio of charge to translational frictional drag. As is well known in the art, such a single stranded product may also be generated by carrying out the PCR reaction with limiting amounts of one of the two sequence-specific nucleobase polymer probes used as a primer.

In a third general embodiment, bound mobility-modified probes are reacted with reporter-labeled nucleotide triphosphate molecules, in the presence of a DNA polymerase to attach reporter groups, which include but are not limited to radioactive and fluorescent moieties, to the 3' end of the probes.

In a fourth general embodiment, each mobility-modified probe includes a sequence that may be enzymatically cleaved when the probe is bound to a target nucleic acid. The cleavage reaction may remove a portion of the nucleobase polymer segment to modify the probe's ratio of charge/translational frictional drag, or may separate a reporter label carried at one end of the probe from a polymer chain carried at the other end of the probe to modify the charge/translational frictional drag of the portion carrying the reporter label. One method for detecting such events relies upon a process, referred to as fluorescence energy resonance transfer (FRET), in which energy is passed between a fluorophore donor and an acceptor molecule. Therefore, in one aspect of this embodiment, the mobility-modified probe comprises two moieties, separated by the cleavage site, which serve as photon donor and acceptor. Where the acceptor molecule is not a fluorophore, the effect is the quenching of donor fluorescence. Cleavage of the bound mobility-modified probe bound to the target nucleic acid physically separates the donor and acceptor moieties and restores fluorescence by the donor moiety, which is readily, and sensitively detected.

In still another aspect of the fourth general embodiment, each mobility-modified probe, which includes a sequence that may be cleaved when the probe is bound to a target nucleic acid, comprises a first mobility-modifying polymer attached to the labeled terminus of the probe, which can be either the 5'-end or the 3'-end of the probe, and a second mobility-modifying polymer attached to the unlabeled terminus of the probe. This aspect of the present invention is illustrated, in a non-limiting manner, by the use of the mobility-modifying polymers of the present invention in "invader assays," which are SNP-identifying procedures based upon flap endonuclease cleavage of structures formed by two overlapping nucleobase polymers that hybridize to a target nucleic acid (see e.g. Cooksey et al., 2000, Antimicrobial Agents and Chemotherapy 44: 1296-1301). Such cleavage reactions release products corresponding to the 5'-terminal nucleobase(s) of the "downstream" nucleobase polymer. Where those cleavage products are labeled and can be separated from the uncleaved nucleobase polymer, an invader assay can be used to discriminate single base differences in, for example, genomic sequences or PCR-amplified genomic sequences.

Attachment of the mobility-modifying polymers of the present invention to the labeled 5'-terminus of the downstream nucleobase polymer used in an invader assay provides cleavage products with distinctive charge to translational frictional drag ratios. Accordingly, a plurality of SNP's are analyzed simultaneously using a plurality of sequence-specific downstream nucleobase polymers, wherein the sequence-specific downstream nucleobase polymers comprise a mobility-modifying polymer of the present invention attached to the labeled 5'-terminus, such that the product generated by flap endonuclease cleavage at each SNP has a distinctive charge to translational frictional drag ratio.

In a further aspect of the invader assay, for example, the downstream nucleobase polymer, which carries a label and a first mobility-modifying polymer of the present invention attached to the 5'-terminus, further comprises a second mobility-modifying polymer attached to the 3'-terminus. The presence of the second mobility-modifying polymer increases the sensitivity of the invader assay by enhancing the difference between the electrophoretic mobility of the flap endonuclease generated product, comprising the 5'-terminus, label, and first mobility-modifying polymer, and the electrophoretic mobility of the uncleaved downstream nucleobase polymer. Accordingly, the second mobility-modifying polymer has a molecular weight of at least 2000. In other embodiments, the second mobility-modifying polymer has a molecular weight of at least 5,000, at least 10,000, at least 20,000, and at least 100,000. In one embodiment, the second mobility-modifying polymer is a mobility-modifying polymer of the present invention, while in other embodiments, the second mobility-modifying polymer is a mobility-modifying polymer of the art, which is, in one illustrative, non-limiting example, an uncharged mono methyl polyethyleneglycol polymer. Moreover, the second mobility-modifying polymer may comprise a mixture of species of different molecular weight, provided that those species do not interfere substantially with detection of the signal product, i.e., the flap endonuclease generated product, comprising the 5'-terminus, label, and first mobility-modifying polymer (see Example 5, below).

In a fifth general embodiment, bound mobility-modified probes are contacted with reporter molecules, including but not limited to intercalating dyes, that bind in a non-covalent manner to the duplex DNA structure formed between the probe and target nucleic acids. Such reporter molecules may form fluorescent complexes when bound to duplex DNA structures, or the non-covalently bound reporter molecule may comprise, for example, a radioactive moiety or other detectable moiety, or a chemical group forming one member of a cognate binding pair, thereby modifying those mobility-modified probes that have bound to a target nucleic acid.

In yet another aspect, the present invention provides a method for separating target nucleic acid molecules, which may comprise different numbers of nucleotide residues, but nevertheless have substantially the same ratio of charge to translational frictional drag. This method comprises contacting a mixture of target nucleic acid molecules with a mobility-modified sequence-specific nucleobase polymer, optionally having a structure selected from the group consisting of structural formula (II) and (III); attaching the mobility-modified sequence-specific nucleobase polymer to substantially all the target nucleic acids forming mobility-modified target nucleic acids, thereby providing each target nucleic acid molecule having the same number of nucleotide residues with a distinctive ratio of charge to translation frictional drag; and separating the mobility-modified target molecules. Generally, the mobility-modified target molecules so formed are separated by electrophoresis, e.g. by capillary electrophoresis, or by capillary electrophoresis in a non-sieving medium.

A mixture of such target molecules is generated, in one embodiment, by chain termination or chemical cleavage sequencing reactions, in which case the target nucleic acids generally comprise at least one detectable label. Where the target molecules are generated by chain termination reactions, those target molecules are primer extension products. In this aspect, the primer extension products and the sequence-specific mobility-modified nucleobase polymer are further contacted under suitable conditions with a template nucleic acid. The template nucleic acid has a 3'-region comprising at least 4 nucleotide residues and a 5'-region comprising at least 4 nucleotide residues, wherein the 3'-region is complementary to 3'-terminal residues of the mobility-modified sequence-specific nucleobase polymer, and wherein the 5'-region is complementary to 5'-terminal residues of each of the primer extension products, such that the 3'-terminal residue of the mobility-modified sequence-specific nucleobase polymer abuts the 5'-terminal residue of a primer extension product, when the mobility-modified nucleobase polymer and the primer extension product are hybridized to the template nucleic acid. Therefore, in this embodiment, the template nucleic acid is used to align the mobility-modified sequence-specific nucleobase polymer and primer extension products under appropriate conditions, so that the hybridized, aligned nucleobase polymers can be covalently joined to one another, optionally by enzymatic ligation. The product formed thereby comprises a mobility-modified sequence-specific nucleobase polymer and a primer extension product, providing a mobility-modified primer extension product having a distinctive ratio of charge to translational frictional drag. Generally, in this aspect of the invention the primer extension product will further comprise at least one detectable label. The detectable label, which may be incorporated into one or more of the mobility-modified sequence-specific primer, deoxyribonucleotide substrate(s) or dideoxyribonucleotide substrate(s), may be, as non-limiting examples, a radioactive label or a fluorescent label. In one embodiment, the chain termination sequencing reaction comprises each of the four dideoxyribonucleotide substrates, wherein each is labeled with a different fluorescent moiety and wherein each of the four different fluorescent moieties are spectrally resolvable from one another. In other aspects of this embodiment, four separate chain termination sequencing reactions are carried out, wherein each of those four reactions comprises a single dideoxyribonucleotide substrate and a mobility-modified sequence specific primer carrying a single, spectrally-resolvable fluorescent moiety. In this instance, the sequencing reactions are terminated and combined to provide a mixture of primer extension products each of which is terminated with a dideoxyribonucleotide residue and is labeled with a spectrally-resolvable fluorescent moiety that corresponds to that dideoxyribonucleotide residue.

In another aspect of this method, the template nucleic acid employed has a 3'-region comprising at least 4 nucleotide residues, a 5'-region comprising at least 4 nucleotide residues, and a central region disposed between the 3'-region and the 5'-region, wherein the 3'-region of the template nucleic acid is complementary to 3'-terminal residues of the mobility-modified sequence-specific nucleobase polymer, and wherein the 5'-region of the template nucleic acid is complementary to 5'-terminal residues of each of the primer extension products. In this instance, hybridization of the sequence-specific mobility-modified nucleobase polymer and a primer extension product to the template nucleic acid molecule, provides a structure in which the 3'-terminal residue of the mobility-modified sequence-specific nucleobase polymer is separated from the 5'-terminal nucleotide residue of a primer extension product by a nucleobase sequence corresponding to the central region of the template nucleic acid. In this instance, a gap remains between the hybridized nucleobase polymers which is filled with a DNA polymerase in the presence of at least one deoxyribonucleoside triphosphate substrate, thereby forming an extended mobility-modified sequence-specific nucleobase polymer. Upon filling of this gap, the extended mobility-modified sequence-specific nucleobase polymer is ligated to the 5'-terminal nucleotide residue of the primer extension product to form a mobility-modified primer extension product having a distinctive ratio of charge to translation frictional drag. The resulting product may also contain a detectable label, which may be incorporated into one or more of the mobility-modified sequence-specific primer, deoxyribonucleotide substrate(s). The detectable label, may be, but is not limited to, a radioactive label or a fluorescent label.

The invention also includes kits useful for carrying out the methods of the present invention. Kits of the invention comprise one or more mobility-modified sequence-specific nucleobase polymers. The kits may also comprise a second nucleobase polymer, typically an oligonucleotide, which is optionally mobility-modified, where the intended assay requires a second oligonucleotide; for example, kits for oligonucleotide ligation assays and PCR analysis. Similarly, kits designed for ligase chain reaction amplification will further comprise at least two additional nucleobase polymers, which together are complementary to a diagnostic ligase reaction product. The kits further may also comprise treating reagents such as restriction enzymes, DNA polymerases, RNases, mismatch binding proteins, ligases, and exonucleases. Primer extension kits appropriate for sequencing or oligonucleotide extension assays for detecting single nucleotide polymorphisms, may further comprise nucleoside triphosphates and/or chain terminating nucleotides. Therefore, components of the kits of the present invention include one more sequence-specific nucleobase polymers, one or more mobility-modified sequence-specific nucleobase polymers, and/or one or more nucleoside triphosphates and/or chain terminating nucleotides, wherein one or more of these components may comprise a reporter label. The kit may also comprise reaction buffers for carrying out hybridizations and enzymatic treatments.

In another embodiment, the invention includes kits comprising one or more of the mobility-modifying phosphoramidite reagents of present invention. One or more of the mobility-modifying phosphoramidite reagents, in such kits, may further comprise one or more protecting groups, reporter molecules, or ligands. Such kits may also comprise one or more solvents, reagents, or solid surface-bound nucleobase monomer for use in the synthesis of mobility-modified sequence specific nucleobase polymers.

The mobility-modified nucleobase polymers of the present invention provide one or more advantages over currently available modified oligonucleotides, as follows. For example, synthesis of the mobility-modified nucleobase polymers of the present invention is compatible with reagents and methods employed in conventional automated instruments for DNA synthesis. Furthermore, when the mobility-modified nucleobase polymers include only uncharged phosphate triester linkages, such as nucleobase polymers according to structural formulae (II) and (III), substantially greater alterations of electrophoretic mobilities can be achieved as compared with the charged PEO modifiers in current use. As illustrated in the working examples provided infra, there is a large difference in the electrophoretic mobilities between mobility-modified nucleobase polymers of the invention which differ by only a single mobility-modifying monomeric unit. As a consequence, the invention permits for greater mobility modifications than can be achieved using conventional PEO modifiers. Significantly, electrophoretic mobility retardations of greater than 100 nucleotides can be readily achieved using standard DNA and RNA chemistries.

Moreover, use of charged phosphate diester linkages in combination with uncharged phosphate triester linkages, such as the mobility-modified nucleobase polymers according to structural formulae (II) and (III), greatly increases the repertoire of available, resolvable mobility modifications. Thus, the present invention enables the ability to simultaneously analyze for greater numbers of target nucleic acid sequences than can be analyzed using currently available PEO modifiers.

5. DETAILED DESCRIPTION OF THE PREFERRED EMBODIMENTS

The present invention provides nucleobase polymer functionalizing reagents and methods for the synthesis of nucleobase polymer functionalizing reagents, as well as procedures for the polymerization of such functionalizing reagents and for their attachment to nucleobase polymers.

The present invention also relates to novel mobility-modified sequence-specific nucleobase polymers that comprise at least one mobility-modifying polymer attached to a nucleobase polymer though one or more mobility-modifying polymer subunits connected through uncharged linkages. The mobility-modified sequence-specific nucleic acids and nucleobase polymers provide improved ratios of charge to translational frictional drag, allowing more effective electrophoretic separation of individual nucleobase polymers within a larger population of nucleic acids, in both sieving and non-sieving electrophoretic media.

The present invention also provides methods for the detection of nucleotide sequences within one or more target nucleic acids using the mobility-modified, sequence-specific nucleobase polymers disclosed herein.

5.1 ABBREVIATIONS AND CONVENTIONS

The abbreviations used throughout the specification and in the FIGS. to refer to the naturally occurring encoding nucleobases are conventional and are as follows: adenine (A), guanine (G), cytosine (C), thymine (T) and uracil (U).

Unless specified otherwise, nucleobase polymer sequences and/or target nucleic acid sequences that are represented as a series of one-letter abbreviations are presented in the 5'→3' direction.

5.2 DEFINITIONS

As used herein, the following terms are intended to have the following meanings:

"Reporter, label," "reporter label" "label" or "tag:" refers to a fluorophore, chromophore, radioisotope, chemiluminescent, spin label, or an enzyme, which causes a detectable event or which allows direct detection of a labeled nucleobase polymer probe by a suitable detector, or a ligand or other first member of a cognate binding pair that can bind specifically and with high affinity to a detectable anti-ligand, anti-hapten, or other second member of a cognate binding pair, such as, but not limited to, reporter-labeled avidin or a reporter-labeled antibody.

"Spectrally resolvable:" means, in reference to a set of fluorescent dyes, that the fluorescence emission bands of the respective dyes are sufficiently distinct, i.e., sufficiently non-overlapping, that the dyes, either alone or when conjugated to other molecules or substances, are distinguishable from one another on the basis of their fluorescence signals using standard photodetection systems such as photodetectors employing a series of band pass filters and photomultiplier tubes, charged coupled devices (CCD), spectrographs, etc., as exemplified by the systems described in U.S. Pat. Nos. 4,230,558 and 4,811,218 or in Wheeless et al., 1985, Flow Cytometry: Instrumentation and Data Analysis, pp 21-76, Academic Press, New York. Generally, all of the dyes comprising a spectrally resolvable set of dyes are excitable by a single light source.

"Nucleobase:" refers to a substituted or unsubstituted nitrogen-containing parent heteroaromatic ring of a type that is commonly found in nucleic acids. Typically, but not necessarily, the nucleobase is capable of forming Watson-Crick and/or Hoogsteen hydrogen bonds with an appropriately complementary nucleobase. The nucleobases may be naturally occurring, such as the naturally-occurring encoding nucleobases A, G, C, T and U, or they may be modified or synthetic. Common modified or synthetic nucleobases include 3-methyluracil, 5,6-dihydrouracil, 4-thiouracil, 5-bromouracil, 5-chlorouracil, 5-iodouracil, 6-dimethyl amino purine, 6-methyl amino purine, 2-amino purine, 2,6-diamino purine, 6-amino-8-bromo purine, inosine, 5-methyl cytosine, 7-deazaadenine, and 7-deazaguanosine. Additional non-limiting examples of modified or synthetic nucleobases of which the target nucleic acid may be composed can be found in Fasmian, CRC PRACTICAL HANDBOOK OF BIOCHEMISTRY AND MOLECULAR BIOLOGY, 1985, pp. 385-392; Beilstein's Handbuch der Organischen Chemie, Springer Verlag, Berlin and Chemical Abstracts, all of which provide references to publications describing the structures, properties and preparation of such nucleobases.

As will be recognized by those of skill in the art, many of the above-described modified or synthetic nucleobases are capable of forming Watson-Crick base pairing interactions with the naturally occurring encoding nucleobases A, T, C, G and U. However, in certain embodiments of the invention, it may be desirable to include in a nucleobase polymer synthetic nucleobases which are not capable of forming Watson-Crick base pairs with either the naturally occurring encoding nucleobases A, T, C, G, and U and/or common analogs thereof, but that are capable of forming non-standard (i.e., non-Watson-Crick) base pairs with one another. Nucleobases having these properties are referred to herein as "non-standard synthetic" nucleobases. Examples of such non-standard synthetic nucleobases include, but are not limited to, iso-guanine (iso-G), iso-cytosine (iso-C), xanthine (X), kappa (K), nucleobase H, nucleobase J, nucleobase M and nucleobase N (see U.S. Pat. No. 6,001,983). These non-standard synthetic nucleobases base-pair with one another to form the following non-standard base pairs: iso-C•iso-G, K•X, H•J and M•N. Each of these non-standard base pairs has three hydrogen bonds. Additional non-standard synthetic nucleobases, as well as methods for their synthesis and methods for incorporating them into nucleobase polymers are found in U.S. Pat. Nos. 5,432,272, 5,965,364 and 6,001,983, the disclosures of which are incorporated herein by reference.

"Nucleobase polymer:" refers to a series of nucleobases that are connected to one another by linkages that permit the linked polymer to hybridize by standard Watson-Crick base pairs or non-standard base pairs to a target nucleic acid having the complementary sequence of nucleobases, or that can hybridize to a duplex target nucleic acid to form a triplex structure via Hoogsteen base pairing rules. A variety of nucleobase polymers capable of hybridizing to a complementary nucleic acid are described in the art. All of these nucleobase polymers are within the scope of the invention. Examples of such nucleobase polymers include native DNAs and RNAs, as well as analogs of DNAs and RNAs. Common analogs include, but are not limited, to DNAs and RNAs in which the respective 2'-deoxyribo- or ribo-nucleosides are connected by phosphonate linkages, phosphoramidate linkages, phosphorothioate linkages, phosphate triester linkages. Nucleobase polymers also include molecules having positively charged sugar-guanidyl interlinkages, such as those described in U.S. Pat. No. 6,013,785 and U.S. Pat. No. 5,696,253 (see also, Dagani, 1995, Chem. & Eng. News 4-5:1153; Dempey et al., 1995, J. Am. Chem. Soc. 117:6140-6141). Sugar-guanidyl analogs in which the sugar is 2'-deoxyribose are referred to as "DNGs," whereas those in which the sugar is ribose are referred to as "RNGs."

Examples of nucleobase polymers having a positively charged polyamide backbone with alkylamine side chains are described in U.S. Pat. Nos. 5,786,461; 5,766,855; 5,719,262; 5,539,082 and WO 98/03542 (see also, Haaima et al., 1996, Angewandte Chemie Int'l Ed. in English 35:1939-1942; Lesnik et al, 1997, Nucleosid. Nucleotid. 16:1775-1779; D'Costa et al, 1999, Org. Lett. 1:1513-1516 see also Nielson, 1999, Curr. Opin. Biotechnol. 10:71-75).

Nucleobase polymers having uncharged backbones have also been described in the art. For example, nucleobase polymers having uncharged polyamide backbones are described in WO 92/20702 and U.S. Pat. No. 5,539,082. Nucleobase polymers having uncharged morpholino-phosphoramidate backbones are described in U.S. Pat. Nos. 5,698,685, 5,470,974, 5,378,841 and 5,185,144 (see also, Wages et al, 1997, BioTechniques 23:1116-1121).

Additional nucleobase interlinkages which may comprise a nucleobase polymer include, but are not limited to, peptide-based nucleic acid mimetic interlinkages (see, e.g., U.S. Pat. No. 5,698,685), carbamate interlinkages (see, e.g., Stirchak & Summerton, 1987, J. Org. Chem. 52:4202), amide interlinkages (see, e.g., Lebreton, 1994, Synlett. February, 1994: 137), methylhydroxyl amine interlinkages (see, e.g., Vasseur et al, 1992, J. Am. Chem. Soc. 114:4006), 3'-thioformacetal interlinkages (see, e.g., Jones et al., 1993, J. Org. Chem. 58:2983), sulfamate interlinkages (see, e.g., U.S. Pat. No. 5,470,967), and linkages including locked nucleoside analogs (LNA), which include bicyclic and tricyclic nucleoside and nucleotide analogs that may be incorporated into nucleobase polymers that are capable of forming sequence-specific duplex and triplex structures with single stranded and double stranded nucleic acids (see, e.g., WO 99/14226).

The nucleobase polymers may be composed wholly of a single type of interlinkage, or may comprise combinations of different interlinkages. In certain embodiments, the nucleobase polymer will be a native DNA or RNA, or a common analog thereof.

"Alkyl:" refers to a saturated or unsaturated, branched, straight-chain or cyclic monovalent hydrocarbon group derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used. In certain embodiments, the alkyl groups are ($C_1$-$C_6$) linear alkyl groups. Furthermore, as used herein, the term "lower alkyl" refers to alkyl groups that consist of from one to six carbon atoms, and, in certain embodiments, lower alkyl groups are ($C_1$-$C_6$) linear alkyl.

"Aryl:" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, the aryl group is ($C_5$-$C_{14}$) aryl, and, in certain embodiments ($C_5$-$C_{10}$). In further embodiments, aryls are cyclopentadienyl, phenyl and naphthyl.

"Capillary electrophoresis:" means electrophoresis in a capillary tube or channel, where the largest inner dimension of the channel cross-section, which need not be a circle, is between about 25-500 microns, allowing efficient heat dissipation throughout the separation medium, with consequently low thermal convection within the medium.

"Sieving matrix or sieving medium": refers to an electrophoresis medium containing crosslinks or non-crosslinked polymers which create a network effective to retard migration of charged species in an electric field. Examples of a sieving matrix are those based on cross-linked polyacrylamide or agarose. A sieving medium may also comprise, as disclosed in U.S. Pat. No. 5,567,292, polylactams such as polyvinylpyrrolidone, N,N-disubstituted polyacrylamides and N-substituted polyacrlyamides.

"Non-sieving matrix or non-sieving medium:" refers to a liquid medium which is substantially free of a mesh or network of polymers which are effective to retard the mobility of analytes.

"Distinctive electrophoretic mobility:" refers to the rate at which an analyte migrates in an electric field in a particular electrophoretic medium. A distinctive mobility refers to a distinctive electrophoretic mobility of the analyte, as compared with electrophoretic mobility of all other detectable analytes present in the sample tested.

"Polymorphism or polymorphic sequences:" refers to a sequence present in a population which shows variation between members of the population. For example, the polymorphisms may relate to single nucleotide differences (single nucleotide polymorphisms: SNP) or differences is the number of repeat sequences.

"Endonuclease:" refers to any enzyme which cleaves a nucleic acid internally. An endonuclease may act on either single stranded or double stranded nucleic acids.

"Short tandem nucleotide repeats:" refers to the collection of different, simple tandem repeats that are present throughout the genome of many organisms. In a non-limiting example, one set of repeated sequences has been characterized as those sequences having the general formula ($A_w G_x T_y C_z$) where A, G, T, and C represent the four nucleotides and w, x, y, and z represent number from 0 to 7, wherein the sum of w+x+y+z ranges from 3 to 7 and n is the repeat number (Edwards, A. et al., DNA typing and genetic mapping with trimeric and tetrameric tandem repeats, Am. J. Hum. Genet. (1991) 49(4): 746-56; Caskey, C. T. et al., U.S. Pat. No. 5,364,759).

"Ligand:" refers to a chemical moiety or structure corresponding to one member of a cognate binding pair that is specifically recognized and bound in a stable complex by a second member of the cognate binding pair. Examples of such cognate binding pairs include, but are not limited to, biotin-avidin, and biotin-streptavidin. Other examples include phenyl boronic acid reagents and phenyl boronic acid complexing reagents derived from aminosalicylic acid (see e.g. U.S. Pat. No. 5,594,151). Therefore, as used herein, the term ligand encompasses the term hapten, which refers to a chemical moiety or structure, for example digoxigenin, as one member of a cognate binding pair, where the second member of the cognate binding pair is an element of the immune system, including but not limited to an intact antibody, a single chain antibody, or an antibody fragment.

"Translational frictional drag:" refers to the measure of a polymer's frictional drag as it moves through a defined, sieving or non-sieving medium.

"Distinctive ratio of charge to translational frictional drag:" refers to the distinctive electrophoretic mobility of a mobility-modified nucleobase polymer as compared to other detectable nucleic acids or nucleobase polymers, both modified and unmodified, that are present within the sample analyzed.

5.3 MOBILITY-MODIFYING PHOSPHORAMIDITE REAGENTS

In one embodiment, the present invention provides mobility-modifying phosphoramidite reagents that are nucleobase polymer functionalizing reagents having a structure according to Formula (I):

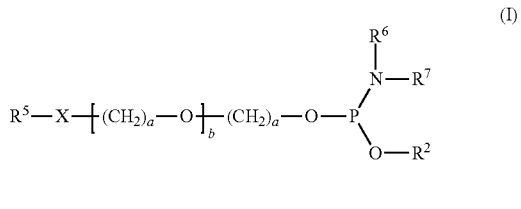

(I)

wherein:

R[5] is selected from the group consisting of hydrogen, protecting group, reporter molecule, and ligand;

X is selected from the group consisting of O, S, NH, and NH—C(O);

each a is independently an integer from 1 to 6; and b is an integer from 0 to 40;

R[6] and R[7] are each independently selected from the group consisting of $C_1$-$C_6$ alkyl, $C_3$-$C_{10}$ cycloalkyl, $C_6$-$C_{20}$ aryl, and $C_{20}$-$C_{27}$ arylalkyl; and R[2] is selected from the group consisting of alkyl comprising at least two carbon atoms, aryl, (R[8])$_3$ Si— where each R[8] is independently selected from the group consisting of linear and branched chain alkyl and aryl, base-stable protecting groups, and R[5]—X—[(CH$_2$)$_a$—O]$_b$—(CH$_2$)$_a$—.

In certain embodiments, R[6] and R[7] are both isopropyl. Where dimers and/or polymers of the mobility-modifying phosphoramidite reagent are desired, R[5] is, inter alia, H or other reactive moiety. Moreover, such dimers and/or polymers can comprise the reagents of the present invention either alone or with other mobility-modifying phosphoramidite reagents of the art. In many embodiments, R[5] is not hydrogen, and in many embodiments R[5] is a protecting group. When R[5] is a protecting group, for example, dimers or polymers of the mobility-modifying phosphoramidite reagent are formed by sequential addition of mobility-modifying phosphoramidite reagent monomers using standard phosphoramidite synthesis chemistry. As used herein, the phrase protecting group encompasses not only the conventional, versatile, selectively cleavable protecting groups well known and widely used in phosphoramidite chemistry and as disclosed below, but also those alternative protecting groups that are not readily or selectively removed by the procedures and conditions of phosphoramidite chemistry. Such alternative protecting groups, particularly those groups resistant to removal under basic conditions, are used in certain embodiments of the present invention. For example, in certain embodiments, an alternative protecting group, R[5] is alkyl or other non-readily or non-selectively cleavable moiety, including, as non-liming examples, compounds of the formula CH$_3$—(CH$_2$)$_d$—O—[—(CH$_2$)$_a$—O—]$_b$—(CH$_2$)$_a$—O—, in which a, and b are as defined in Formula (I) above, and d is an integer in the range of 0 to 5.

The mobility-modifying phosphoramidite reagents of the present invention are generally synthesized according to Scheme I, using methods and reagents well known to those skilled in the art, which provides, for example the illustrative mobility-modifying phosphoramidite reagent of the invention (7). In Scheme (I), DMT represents dimethoxytrityl, iPr represents isopropyl and R[2] and b are as previously defined for structural Formula (I).

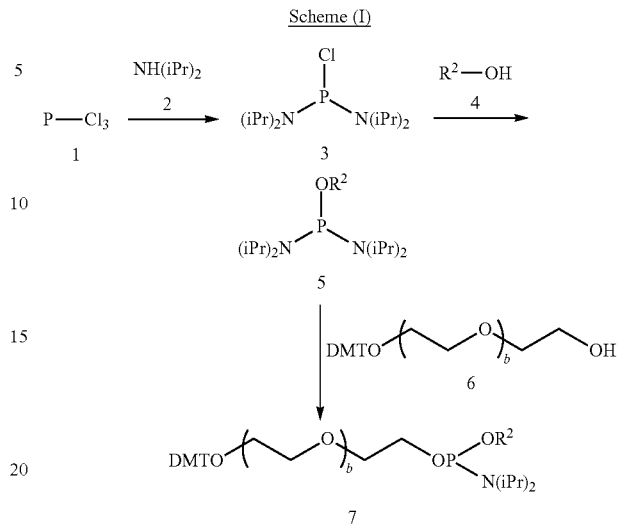

Scheme (I)

Referring to Scheme (I), a DMT protected polyethylene oxide phosphoramidite reagent 7 that can be used in connection with standard phosphoramidite DNA chemistry is prepared.

Initially, phosphorous trichloride 1 is reacted with diisopropylamine 2 in a solvent, for example toluene, to form bis(diisopropylamino)chlorophosphine ester 3. Subsequently, the tetraisopropylaminophosphine 3 is reacted with the hydroxyl group on alcohol 4 thereby generating R[2]-bis(diisopropylamino)phosphite ester 5. Addition of an appropriately protected mobility-modifying polymer having a free hydroxyl, such as DMT protected polyethylene oxide 6, along with an activator, for example tetrazole, gives rise to the phosphoramidite, reagent 7, an R[2]-diisopropylaminophosphite ester wherein the polymer is attached to the phosphorous atom through an ester bond.

The phosphoramidite reagent 7 is suitable for use in DNA synthesizers to couple the mobility-modifying polymer to a nascent nucleobase polymer. As described in Example 2 and illustrated in Scheme (II), infra.

The mobility-modifying phosphoramidite reagents of the present invention are compatible with standard phosphoramidite synthetic schemes, and, therefore can be used with commercially available instruments for nucleobase polymer synthesis. In addition he mobility-modifying phosphoramidite reagents of the present invention are readily attached to either the 5'-end or the 3'-end of a nucleobase polymer.

In one embodiment of the present invention, the mobility-modifying phosphoramidite reagent of the present invention is added to the 5'-end of a nucleobase polymer attached to a solid support (8), as depicted in Scheme II, infra. In this instance the illustrative mobility-modifying phosphoramidite reagent of the present invention (7) is condensed with the free 5'-hydroxyl moiety of the surface-bound nucleobase polymer to yield the intermediate structure (9), which is then sequentially deprotected to remove base-labile and acid-labile protecting groups and to cleave the product from the solid support, yielding the mobility-modified nucleobase polymer (12). In this embodiment, the esterified moiety R[2] is stable to each step in the above reaction scheme, and, therefore the phosphate triester linkage is uncharged. Moreover, as would be apparent to those skilled in the art, the surface-bound intermediate (10), can be treated with mild acid, e.g. 3% dichlroacetic acid (DCA), to remove the DMT protecting group to provide a free hydroxyl moiety and then condensed with (7) to provide a mobility-modified nucleobase polymer with two molecules of (7) joined to the 5'-end of the mobility-modified nucleobase polymer. Therefore, repetition of this condensation reaction with (7) through n cycles of reagent addition, provides a mobility-modified nucleobase polymer with n molecules of the mobility-modifying phosphoramidite reagent of the present invention attached to the 5'-end of the nucleobase polymer.

In another embodiment, the mobility-modifying phosphoramidite reagents of the present invention are added to the 3'-end of a nucleobase polymer, rather than, or in addition to, the 5'-end of the nucleobase polymer to be modified. In one illustrative example of this embodiment, depicted in Scheme V, infra. In this synthetic scheme, a mobility-modifying phosphoramidite reagent of the present invention (7), is condensed with the 5'-hydroxyl moiety of a nucleobase residue, thymidine, which is attached to a solid support, via, the 3'-hydroxyl moiety of the nucleobase residue. The condensation product (23) obtained is then oxidized to the phosphate triester (24), deprotected with mild acid to provide the free hydroxyl moiety of (25). The phosphate triesters synthesized are chiral compounds and both the R and S enantiomers are formed when synthesized according to the methods disclosed herein. The racemic mixture of the phosphate triesters synthesized is used without separation into enantiometrically pure R and S forms. Condensation of (25) with a 5'-protected nucleotide phosphoramidite reagent (26), yields a dinucleobase intermediate having a mobility-modifying phosphoramidite reagent of the present invention positioned between the two nucleobase monomers (27). Repeated cycles of condensation with 5'-protected nucleotide phosphoramidite, followed by deprotection and cleavage from the solid support, provides a nucleobase polymer carrying a mobility-modifying polymer at the 3'-end of that nucleobase polymer (29). As noted supra, one or more of the mobility-modifying phosphoramidite reagents of the present invention can be added to the nucleobase polymer either alone or in combination with one or more mobility-modifying phosphoramidite reagents known in the art. Accordingly, one or more of the linking groups formed between mobility-modifying phosphoramidite reagents or between a mobility-modifying phosphoramidite reagent and the nucleobase polymer can be a charged phosphate diester bond. Furthermore, one or more of the mobility-modifying reagents employed can be a branched compound, e.g. as in structure (21), provided it is not the 5'-proximal moiety with which a 5'-protected nucleotide phosphoramidite is to be condensed.

In another embodiment a mobility-modifying phosphoramidite reagent of the present invention is attached to a readily-cleaved chemical link that is bonded to a solid support such as controlled pore glass or polystyrene. An example of such a readily-cleaved chemical link( bonded to a solid support is compound 33:

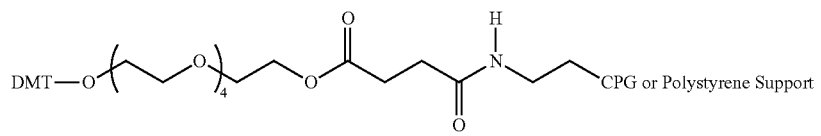

the synthesis of 33 is described below:

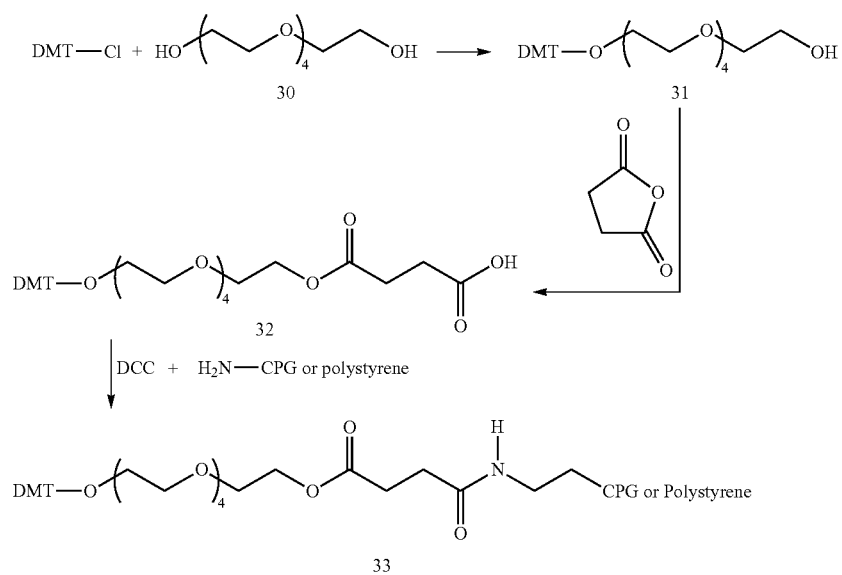

In this manner, nucleobase polymers carrying mobility-modifying reagents at the 3'-end are assembled without the additional nucleobase residue at the 3'-end of the molecule, as depicted in Scheme V and compound (29). However, the advantage of the general method depicted in Scheme V, is that nucleobase-bound solid supports not only are commercially available, but they are also provided in the form of pre-assembled cartridges, which are filled with a nucleotide-bound solid support, that are compatible with automated nucleobase polymer synthesizing machines.

The mobility-modifying phosphoramidite reagents of the present invention yield uncharged phosphate triester linkages when joined to either or both of the 5'-end and/or the 3'-end of a nucleobase polymer, as well as when joined to another mobility-modifying phosphoramidite reagent of the present invention. Accordingly the esterified moiety, i.e. $R^2$ of Formula I, and, in certain embodiments, $R^{10}$ and/or $R^4$ of Formulae II and III, infra, will be stable to all steps of conventional phosphoramidite chemistry. That is the esterified moiety should be not be removed during, inter alia, the deprotection steps, depicted, for example in Schemes III and V. More specifically, the esterified moiety should be stable to the procedures and conditions required for deprotection of protected amines and cleavage of the mobility-modified nucleobase polymer from the solid support, such that the linkage between the mobility-modifying monomer units and between a mobility-modifying monomer unit and the 3'-end or 5'-end of the nucleobase polymer is an uncharged phosphate ester.

Accordingly, when $R^2$ of Formula I, and $R^{10}$ and/or $R^4$ of Formulae II and III, infra, are alkyl, $R^2$, and $R^{10}$ and/or $R^4$ are selected from the group consisting of alkyl comprising at least two carbon atoms, e.g. $C_2$-$C_6$ linear alkyl.

The mobility-modifying phosphoramidite reagents of the present invention may also be used in conjunction with other nobility-modifying phosphoramidite reagents that are known in the art, including, for example, the representative PEO phosphoramidite reagent depicted supra, which comprises an esterified cyanoethyl moiety. As depicted in Scheme III, infra, the surface-bound nucleobase polymer intermediate (10), which comprises one molecule of a mobility-modifying phosphoramidite reagent of the present invention, can be treated with mild acid, e.g. 3% DCA, to remove the DMT protecting group to provide the surface-bound compound (13) carrying a free hydroxyl moiety. Condensation of the PEO phosphoramidite reagent, (14), with surface-bound (13) provides a nucleobase polymer with two mobility-modifying reagents joined to the 5'-end of the nucleobase polymer. In this scheme, deprotection and cleavage of the product from the solid surface also results in removal of the esterified cyanoethyl group of reagent (14). Therefore, in this embodiment, the linkage formed between the second mobility-modifying reagent (14) added and the mobility-modified nucleobase polymer, is a charged phosphate diester bond.

In a further embodiment, the nobility-modifying phosphoramidite reagents of the present invention encompass dendritic reagents comprising two esterified mobility-modifying groups attached to each phosphorous atom. An example of such a compound (21) and a general scheme for its synthesis are depicted in Scheme IV, infra. As would be apparent to those skilled in the art, repeated cycles of condensation using reagent (21) would provide a geometric increase in the number of mobility-modifying phosphoramidite reagents attached to a surface-bound nucleobase polymer, according to the synthetic method depicted in Scheme IV, infra It would also be apparent to one of skill in the art that a nucleobase polymer can be modified with one or more of the mobility-modifying phosphoramidite reagents (7), (14), and (21), generally according to Scheme II, III, or V, infra, to provide a series of mobility-modified nucleobases polymers, having one or more branched and/or unbranched, charged and/or uncharged mobility-modifying moieties.

5.4 COMPOSITIONS OF MOBILITY-MODIFIED NUCLEOBASE POLYMERS

In one aspect of the present invention, mobility-modifying polymer chains are attached to sequence-specific nucleobase polymers by a linking group. Various polymers adaptable to the embodiment include, among others, polyoxides, polyamides, polyimines, and polysaccharides. The compositions also embody polymer chains in the form of copolymers or block polymers, such as polyethylene oxide and polyamine (see e.g. Vinogradov, S. V. (1998) Self assembly of polyamine-poly(ethylene glycol) copolymers with phosphorothioate nucleobase polymers, *Bioconjugate Chem.*, 2: 805-12), having one or more uncharged linkers between monomer units.

In one embodiment, mobility-modifying polymers are polyoxides or polyethers. In this context, the term polyoxide is used to denote polymers with oxygen atoms in the main chain, particularly those with monomer units of the type $[O-(CH_2)_n]$ where n is an integer selected from the range of 1 to 15, in certain embodiments n is selected from the range of 2 to 6, and in other embodiments, n=2, together with their derivatives. Linear polyoxides applicable to the composition include, for example, poly(methylene oxide), poly(ethylene oxide), poly(trimethylene oxide) and poly(tetramethylene oxide). Branched polyoxides provide additional bases for mobility-modification by, in some cases, imparting to the mobility-modified nucleobase polymer a translational frictional drag that is different than that provided by a linear polymer chain. Branched polymers, for example poly(propylene oxide) which are appreciably soluble in aqueous solvents, are used in certain embodiments. Other applicable branched polymers include poly(acetaldehyde), and poly(but-1-ene oxide).

In another embodiment, the mobility-modifying polymer is a monodisperse linear polyoxide of polyethyleneoxide (PEO) because of its high degree of solubility in a variety of aqueous and organic solvents. Moreover, chemistry of poly (ethylene oxide) and methods of use for modifying chemical and biological compounds are well known in the art. (see e.g. Grossman, P. D. et al, U.S. Pat. No. 5,777,096; Muller, W. et al. (1981) Polyethylene glycol derivatives of base and sequence-specific DNA ligands: DNA interaction and application for base specific separation of DNA fragments by gel electrophoresis, *Nucleic Acids Res.* 9: 95-119); Maskos, U., (1992) Oligonucleotide hybridization on glass supports: a novel linker for oligonucleotide synthesis and hybridization properties of oligonucleotides synthesized in situ, *Nucleic Acids Res.* 20:1679-84). Accordingly, those skilled in the art can readily vary the number of polyethylene units in the mobility-modifying polymer to impart distinctive ratio of charge to translational frictional drag to the mobility-modified sequence-specific nucleobase polymer.

In addition, the mobility-modifying polymers of the embodiment may further comprise functional groups, such as a hydroxyl, sulfhydral, amino or amide group. These functional groups permit attachment of various reporter molecules, ligands, or other polymer chains. Protecting groups may be present on the functional group when the mobility-modifying polymer is being coupled to the sequence-specific nucleobase polymer, or during reaction of other functional groups with the sequence-specific mobility-modified nucleobase polymer. Groups suitable for protecting specific functional groups, including methods for removal, are well known in the art such that the art provides ample guidance for selecting the appropriate protecting reagents (see e.g. Greene and Wuts, *Protective Groups in Organic Synthesis,* 2nd ed., John Wiley & Sons, Inc., New York, 1991). For example, hydroxyl groups are protectable with acid labile groups such as dimethoxytrityl (DMT), or with base labile group such as fluorenyl methyl chloroformate (Fmoc).

Protecting groups useful in the present invention, encompass not only the conventional, versatile, selectively cleavable protecting groups well known and widely used in phosphoramidite chemistry and as disclosed above, but also those alternative protecting groups that are not readily or selectively removed by the procedures and conditions of phosphoramidite chemistry. Such alternative protecting groups, particularly those groups resistant to removal under basic conditions, are used in certain embodiments of the present invention. For example, in certain embodiments, as an alternative protecting group, $R^5$ is alkyl or other non-readily or non-selectively cleavable moiety, including, as non-liming examples, compounds of the formula $CH_3-(CH_2)_c-O-[-(CH_2)_a-O-]_b-(CH_2)_a-O-$, in which a, and b are as defined in Formula (I) above, and c is an integer in the range of 0 to 5.

Another aspect of the invention involves linking groups that attach the mobility-modifying polymer to the sequence-specific nucleobase polymer. In a general embodiment, the group attaching the mobility-modifying polymer chain to the nucleobase polymer comprises phosphate triester, phosphonate, phosphoamidate, phosphotriester or phosphodithioate linkage. Phosphonate and phosphate triester linkages permit attachment of other chemical constituents to the phosphorous atom to effect further differences in the ratio of charge to translational frictional drag between mobility-modified nucleobase polymers. Thus, one embodiment includes alkylphosphonate linkages, such a methyl phosphonate.

In a further embodiment, the linkage is a phosphate triester, wherein the free ester has attached various chemical groups so as to render the linker uncharged, such as alkyls, functionalized alkyls, or polymers. When the chemical group is an alkyl, the compound may be a linear or branched alkyl, generally a lower alkyl group. Linear alkyls include, but are not limited to, methyl, ethyl, propyl, or butyl groups, while branched alkyls include, but are not limited to, isopropyl or tertbutyl groups. However the chemical groups attached to the free ester are generally limited to those groups that are stable to all steps of conventional phosphoramidite chemistry, including deprotection steps and especially to the procedures and conditions required for the deprotection of protected amines, such that the resulting linkage is an uncharged phosphate triester. Therefore, when such groups are alkyl, the group is generally an alkyl other than methyl, for example, $C_2$-$C_6$ linear alkyl, since mono methyl phosphate triesters tend to be less stable than higher-order alkyl phosphate triesters. The alkyl group may also have attached functional moieties, such as reporters, ligands or biotin molecules. Reporter molecules include but are not limited to fluorescent, chemiluminescent or bioluminescent molecules, while ligands include, but are not limited to, molecules such as cholesteryl, digoxigenin, 2,4 dinitrophenol, and biotin. When the chemical group is a polymer, the same types of polymers set forth above, including but not limited to polyoxides, polyamides, polyimines, polysaccharides, and polyurethanes, function as suitable substituents.

The sequence-specific nucleobase polymers in one embodiment of the invention are natural or synthetic. Natural nucleic acids and oligonucleotides are obtained by cloning the desired fragment in a cloning vector and isolating the desired nucleic acid fragment by restriction enzyme digestion. Alternatively, they are made using oligonucleotide templates and enzymatic synthesis, such as polymerase chain reaction (Sambrook, J. et al., Molecular Cloning: A Laboratory Manual, Cold Spring Harbor Laboratory, New York, 2000).

In another embodiment, the sequence-specific nucleobase polymers are synthetic nucleobase polymers. Synthetic sequence-specific nucleobase polymers comprise deoxyribonucleic acids (DNA), ribonucleic acids (RNA) or composites of DNA and RNA. Further modification of the nucleobases of the deoxy or ribonucleic acids are possible. Modified bases include inosine, deoxynapthosine, etheno adenosine and cytidine, and bromodeoxyuridine. Other modified bases readily used in nucleobase polymer synthesis are 7-deaza purines, $N^6$ methyl adenosine, $O^6$ methyl guanosine, and 2-aminopurine.

In another embodiment, the sequence-specific nucleic acids and nucleobase polymers are analogs, for example phosphonate nucleobase polymer, nucleobase polymers comprising one or more locked nucleoside analogues, peptide nucleic acids (PNA), phosphorothioate nucleobase polymers, phosphate triester nucleobase polymers, or nucleobase polymers having chain terminating nucleosides.

Phosphonate nucleobase polymers have a backbone comprising phosphonate internucleotide linkages. The phosphonates known in the art of nucleobase polymer synthesis include H-phosphonate, alkyl phosphonate (e.g. methylphosphonate), 2-aminoethylphosphonate, and benzylphosphonate (Samstag, W., (1996) Synthesis and properties of new antisense nucleobase polymers containing benzylphosphonate linkages, *Antisense Nucleic Acid Drug Dev.* 6: 153-56; Fathi, R., (1994) nucleobase polymers with novel, cationic backbone constituents: aminoethylphosphonates, Nucleic Acids Res. 22: 5416-24; Seliger, H., (1990). Simultaneous synthesis of multiple nucleobase polymers using nucleoside-H-phosphonate intermediates, DNA Cell Biol., 9: 691-6; Zhou, Y., (1996) Solid-phase synthesis of oligo-2-pyrimidinone-2'-deoxyribonucleotides and oligo-2-pyrimidione-2'deoxyriboside methylphosphonates, *Nucleic Acids Res.* 24: 2652-2659). The advantages of nucleobase polymers having phosphonate linkages are their property of readily forming stable triple helix structures and their higher resistance to nuclease action.

Locked nucleoside analogues (LNA) include bicyclic and tricyclic nucleoside and nucleotide analogues that may be incorporated into nucleobase polymers that are capable of forming sequence-specific duplex and triplex structures with single stranded and double stranded nucleic acids. Those duplex and triplex structures that comprise LNA-containing, sequence specific nucleobase polymers are more thermostable than the corresponding structures formed with non-analogue-containing nucleobase polymer molecules (see e.g. WO 99/14226).

Peptide nucleic acids (PNA) are synthetic polyamides which comprise repeating units of the amino acid, N-(2-aminoethyl)-glycine to which bases such as adenine, cytosine, guanine, thymine are attached via the methylene carbonyl group. Other bases including pseudo isocytosine, 5 methyl cytosine, pseudouracil, hypoxanthine are suitable for incorporation into PNAs. The resistance of PNA nucleobase polymers to nucleases and the high stability of PNA-DNA hybrids make them desirable probes for identifying target polynucleotides, except in methods requiring nuclease treatments (Egholm, M., et al (1992) Peptide nucleic acids (PNA): Oligomicleotide analogues with an achiral peptide backbone, *J. Am, Chem. Soc.* 114: 1895-1876; Hanvey, J. C., (1992)

Antisense and antigene properties of peptide nucleic acids, *Science* 258:1481-5; Nielson, P. E. et al., (1993) Sequence-specific inhibition of DNA restriction enzyme cleavage by PNA nucleic acids, *Nucleic Acids Res.* 21: 197-200).

Oligonucleotide and nucleobase polymer analogs with phosphorothioate or phosphorodithioate internucleotide linkages have sulfur atom in place of the oxygen as the non-bridging ligands bound to the phosphorous (Eckstein, F., (1985), Nucleoside phosphorthioates, *Ann. Rev. Biochem.*, 54: 317-402). Phosphorothioate diesters are chiral at the phosphorous atom (Rp and Sp) and have utility as nucleobase polymer probes and antisense molecules because of their resistance to nucleases (Zon, G., Phosphorothioate oligonucleotides. In Oligonucleotides and Analogues: A practical approach, (Eckstein, F. ed) IRL Press, Oxford, pg 87-108). Phosphorodithioates have both the non-bridging ligands bound to the phosphorous as sulfur atoms (Caruthers, M. H. et al., (1992), Chemical synthesis of Deoxyoligonucleotides and Deoxyoligonucleotide analogs, *Meth. Enzy.* 211: 3-20).

In another embodiment of the invention, the sequence-specific nucleobase polymer analogs comprise different combinations of internucleotide linkages. Thus a nucleobase polymer may comprise methylphosphonate, phosphate diester, and N-(2-aminoethyl)-glycine internucleotide linkages (Miller, P. S. et al., (1999), A psoralen-conjugated triplex forming oligodeoxyribonucleotide containing alternating methylphosphonate-phosphate diester linkages: synthesis and interactions with DNA, *Bioconjugate Chem.* 10: 572-577; Gildea, B. D. et al., U.S. Pat. No. 6,6063,569). Other sequence-specific nucleobase polymer analogs may comprise a combination of phosphorothioate-phosphate diester internucleotide linkages (see e.g. Ghosh M. K. (1993), Phosphorothioate-phosphate diester oligonucleotide co-polymers: assessment for antisense, *Anticancer Drug Des*, 8(1): 15-32). Combinations of different internucleotide linkages offer nucleobase polymers with different hybridization characteristics and nuclease resistance.

In another embodiment of the present invention, the mobility-modified sequence-specific nucleobase polymer comprises at least one non-negatively charged internucleotide linkage. In one non-limiting example, at least one internucleotide linkage of the mobility-modified sequence-specific nucleobase polymer is an uncharged mono alkyl phosphate triester linkage, while in another non-limiting example, the internucleotide linkage is a positively charged amide linkage comprising an alkylamine side chain. In this embodiment, the non-negatively charged internucleotide linkage further alters the charge to translational frictional drag ratio of the mobility-modified sequence-specific nucleobase polymer of the present invention. In another non-limiting example, at least one internucleotide linkage of the mobility-modified sequence-specific nucleobase polymer is a phosphoamidate linkage, which is another non-negatively charged internucleotide linkage that will alter the charge to translational frictional drag ratio of the mobility-modified sequence-specific nucleobase polymer of the present invention. Synthesis of oligonucleotides comprising a phrophoramidate internucleotide linkage is described in U.S. Pat. No. 5,476,925, which is hereby incorporated by reference in its entirety.

In another embodiment the mobility-modified sequence-specific nucleobase polymers are conjugated to various reporters, ligands and polymer molecules. All components of the mobility-modified sequence-specific nucleic acid or nucleobase polymer are amenable to conjugation, including at internal or terminal nucleotide residues, the phosphate triester group linking the polymer to the nucleobase polymer, and the mobility-modifying polymer. Those skilled in the art are well versed in generating the appropriate modifications to form the desired conjugate (see e.g. Oligonucleotides and Analogs, F. Eckstein, ed., Chapter 8-9, IRL Press, 1990; Agrawal, S. (1986), Efficient methods for attaching non-radioactive labels to the 5' ends of synthetic oligodeoxyribonucleotides, *Nucleic Acids Res.* 14: 6227-45; Nelson, (1992), *Nucleic Acids Res.*, 20 (23): 6253-6259). When the conjugation is to the polymer of the mobility-modified nucleobase polymer, the polymer has appropriate functional groups such as hydroxyl, sulfhydral, amide or amino groups that permit attachment of one or more reporter, and ligand molecules. When the conjugation is to a phosphate triester linking group, the free ester provides the site of attachment.

Conjugating various reporter and ligand moieties permits detection, modification, or immobilization of the sequence-specific mobility-modified nucleobase polymer. They also permit further mobility-modification of the sequence-specific mobility-modified nucleobase polymer. Reporter molecules include, but are not limited to fluorescent compounds, such as fluoresceine, rhodamine, Texas red, cyanine dyes, and acridine dyes. Ligands include, but are not limited to, 2,4 dinitrophenol, digoxigenin, and cholesterin, as well as enzymes, or enzyme substrates that could be attached to the sequence-specific mobility-modified nucleobase polymer. Conjugated ligands, including but not limited to biotin, permit isolation, detection, or immobilization of the mobility-modified nucleobase polymer by binding to avidin or streptavidin.

In view of the embodiments set forth above, certain embodiments of sequence-specific mobility-modified nucleic acids or nucleobase polymers have a structure according to structural formula (II) or (III):

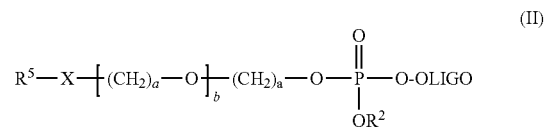

(II)

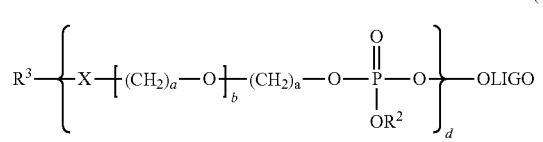

(III)

or a salt thereof, wherein:

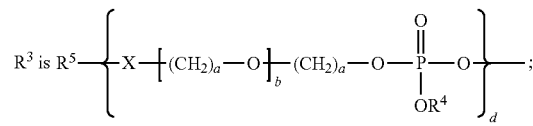

$R^2$, $R^5$, X, a, and b are as in Formula (I);

each $R^{10}$ is independently selected from the group consisting of hydrogen and $R^2$;

each $R^4$ is independently selected from the group consisting of hydrogen and $R^2$;

each b is independently an integer from 0 to 40;

each d is independently an integer from 1 to 200; and

OLIGO is a sequence-specific nucleobase polymer, typically comprising at least 5 nucleobases, with the proviso that at least one $R^{10}$ or at least one $R^4$ is other than hydrogen.

Amongst the various mobility-modified nucleobase polymers of structural formulae (II) and (III) are those compounds in which each X is O, each a is the same (generally 2), each b is in the range of 1 to 15 and, and in certain embodiments, b is in the range of 1 to 6, and the OLIGO is a DNA, RNA, and/or an analog of DNA or RNA, oligomer, each d is in the range of 1 to 200, in certain embodiments in the range of 1 to 100, and further embodiments in the range of 1 to 50.

In the compounds of structural formula (III) each $R^{10}$ and/or $R^4$ may, independently of one another, be a hydrogen atom. When $R^{10}$ and/or $R^4$ are hydrogen, the resultant phosphate ester group typically has a pKa in the range of 0 to 1. Thus, when the pH of the assay conditions is above the pKa, as is usually the case in biological assays, the hydrogen atom exchanges with solvent and at least, a net fraction of the phosphate ester groups are negatively charged. Due to the ionizability of the phosphate ester group, those of skill in the art will appreciate that for purposes of defining the invention, selecting $R^{10}$ and/or $R^4$ to be hydrogen includes within its scope both the unionized form and the ionized (i.e., negatively charged) form of the resultant phosphate ester group.

Similarly, other groups within the illustrated or described compounds may be ionizable. Moreover, many of the compounds may include chiral centers or exist in different tautomeric or geometric isomeric forms. As any structural drawings may represent only a single ionizable, tautomeric, enantiomeric or geometric isometric forms, it will be understood that the structural drawings are not intended to be limiting, and any non-illustrated ionizable, tautomeric, enantiomeric or geometric isomeric forms of the compounds are intended to be within the scope of the present invention.

In the mobility-modified nucleobase polymers of structural formulae (II) and (III), the mobility-modifying segment of the molecule may be branched or linear. When linear, each $R^{10}$ and $R^4$ is either hydrogen (where possible), alkyl comprising at least two carbon atoms, or aryl. When branched, at least one $R^{10}$ or $R^4$ is $R^5$—X[(CH$_2$)$_a$—O]$_b$—(CH$_2$)$_a$—. In these embodiments where an uncharged phosphate ester linkage is desired, the chemical groups attached to the free ester are generally limited to those groups that are stable to all steps of conventional phosphoramidite chemistry, including deprotection steps and especially the procedures and basic conditions required for the deprotection of protected amines. Therefore, when such groups are alkyl, the group is an alkyl other than methyl, for example, $C_2$-$C_6$ linear alkyl, since methyl phophotriesters tend to be less stable than higher-order alkyl phosphate triesters.

Identical or different mobility-modifying polymer combinations can be used to provide the mobility-modified sequence-specific nucleobase polymer with distinctive, predictable mobility alterations. The sequence-specific nucleobase polymers comprise DNA, RNA, or analogs thereof, as described above. The OLIGO may be labeled or unlabeled. Those skilled in the art are well versed in devising nucleobase polymer sequences useful for detecting a selected nucleic sequence within one or more target nucleic acids by the various methods described below.

5.5 METHODS OF SYNTHESIS

The methods for synthesizing the nucleobase polymer-functionalizing reagents of the present invention and for synthesizing the various compositions of mobility-modified sequence-specific nucleobase polymers comprising those functionalizing reagents, follow variations of known reaction schemes used for sequence-specific nucleobase polymer synthesis and modification. As regards the mobility-modifying polymers of the embodiments, methods of synthesizing various polymers are well known. Polymers suitable as mobility-modifiers include, among others, polyoxide, polyamide, polyimine, and polysaccharides (see e.g. Molyneux, P., *Water-Soluble Synthetic Polymers: Properties and Behavior*, CRC Press, 1984; Gravert, D. J., (1977) *Synthesis on soluble polymers: new reactions and the construction of small molecules, Curr Opin Chem Biol*, 1 (1):107-13). Long chain alcohols, such as lipohilic $C_{16}$ alcohols used as spacer arms to conjugate functional moieties, are also suitable as mobility-modifiers. Functional groups, such as the hydroxyls on polyoxides, are protected by an appropriate protecting agent, such as 4',4'-dimethoxytrityl chloride. Groups suitable for protecting specific functional groups, as well as methods for removal, are well known and will be apparent to those skilled in the art. Guidance for selecting protecting reagents can be found, for example, in Greene and Wuts, *Protective Groups in Organic Synthesis*, 2nd ed., John Wiley & Sons, Inc., New York, 1991)

The nucleobase polymers attached to the mobility-modifying polymer chains are natural or synthetic nucleic acids having defined nucleotide sequences. In one embodiment the sequence-specific nucleobase polymer is a natural DNA or RNA. Natural nucleic acids are readily prepared by cloning the desired fragment in a cloning vector and isolating the desired nucleic acid fragment by restriction enzyme digestion of the recombinant molecule. Alternatively, they are made from nucleic acid templates by enzymatic synthesis, such as polymerase chain reaction (Sambrook, J. et al, supra).

In one embodiment, the nucleobase polymers are chemically synthesized using the phosphoramidite or phosphate triester methods, either in solution or on a suitable inert solid support. Methods for nucleobase polymer synthesis are well known to those skilled in the art (see e.g. Caruthers et al. (1982) *Genetic Engineering* 4:1-17; Users Manual Model 392 and 394 Polynucleotide Synthesizers, (1990), pages 6-1 through 6-22, Applied Biosystems, Part No. 901237).

The phosphoramidite method is one method of synthesis for sequence-specific oligodeoxyribonucleic and oligoribonucleic acids. In general, a protected nucleoside is conjugated to a solid support and then treated with acid, for example trichloroacetic acid, to remove the 5'-hydroxyl protecting group, thus generating a free hydroxyl group for the subsequent coupling reaction. A protected nucleoside phosphoramidite monomer and an activating reagent such as tetrazole are reacted with the nucleoside bound to the solid support. The activating agent protonates the nitrogen of the phosphoramidite, permitting nucleophilic attack of the phosphorous atom by the exposed hydroxyl group. Following nucleoside addition, the growing chain is capped, generally with acetic anhydride and 1-methylimidazol, to terminate any nucleotide chains that failed to react. The internucleotide phosphite linkage is oxidized, with iodine as the preferred oxidizing agent, to the more stable phosphate triester. Following oxidation, the hydroxyl protecting group is removed with a weak acid, such as trichloroacetic and the cycle of reactions is repeated until formation of a nucleobase polymer of the desired length and sequence is complete. Base treatment cleaves the nucleobase polymer from the solid support and also removes any phosphate protecting groups, such as β-cyanoethyl. Complete deprotection of the exocyclic amino groups on the nucleoside bases is accomplished by treating the nucleobase polymer in base at elevated temperatures, for example 55° C. in concentrated ammonium hydroxide. The remaining protecting groups, usually dimethoxytrityl (DMT) groups on the 5'-hydroxyl, are removed during synthesis or, alternatively, may be left on if reverse phase HPLC is the purification method of choice. After synthesis, the nucleobase polymer is amenable to labeling at the 5' terminus (see e.g. Oligonucleotides and Analogs, F. Eckstein (1990), Ed. Chapter 8, IRL Press; Orgel et al., (1983) *Nucleic Acids Research* 11:6513; U.S. Pat. No. 5,118,800), the phosphate diester internucleotide linkages (see e.g., Orgel et al., supra at Chapter 9), or the 3' terminus (see e.g. Nelson, (1993), *Nucleic Acids Research* 20:6253-6259).

In another embodiment, the nucleobase polymers are analogs having modifications of the base, the sugar, or the backbone. Modifications in the backbone, include, but are not limited to polyamide (i.e. peptide nucleic acids), phosphonate, phosphorothioate, phosphodithioester, and phosphoamidate internucleotide linkages. Methods of synthesizing sequence-specific nucleobase polymer analogs with modified internucleotide linkages are well known to those skilled in the art (see e.g. Oligonucleotides and Analogs, A Practical Approach, Eckstein, F., Ed., IRL Press, (1990); Agrawal, S., (1993), Protocols for Oligonucleotides and Analogs, *Meth. Mol Biol.,* Vol 20, Humana Press).

Sequence-specific nucleobase polymers with polyamide backbones between nucleobases are also known as peptide nucleic acids (PNA), one example of which is a polymer having repeating units of N-(2-aminoethyl)-glycine to which nucleobases are attached through a methylene carbony group (Nielson, P. E. (1991), Sequence-selective recognition of DNA by strand displacement with a thymine-substituted polyamide, *Science* 254:14971500).

As used herein, "PNA" refers to a polymer of nucleobases linked together via an uncharged polyamide backbone. The PNA backbone may be any backbone of acyclic, achiral and neutral polyamide linkages to which nucleobases can be attached and that satisfies the criteria discussed supra. PNAs useful in the present methods are described, for example, in U.S. Pat. No. 5,539,082 and WO 92/20702, the disclosures of which are incorporated herein by reference. The amino acids which form the polyamide backbone may be identical or different, but are generally identical. In certain embodiments, PNAs are those in which the nucleobases are attached to an N-(2-aminoethyl)-glycine backbone, i.e., a peptide-like, amide-linked unit (see, e.g., U.S. Pat. No. 5,719,262; Bucharrdt et al., 1992, WO 92/20702; Nielsen et al., 1991, Science 254:1497-1500).

Various strategies for PNA synthesis are available. In one method, PNA monomers used for synthesis have the exocyclic amino groups protected by benzyloxycabonyl (Z) while the amine is protected with tertbutyl oxycarbonyl (tBoc). Protected monomer bound to a solid substrate is deprotected using a strong acid, such a trifluoroacetic acid (TFA), to generate a free amino group for the subsequent coupling to the next PNA monomer. A PNA monomer activated, for example by carbodiimides or O-(7 azabenzotriazol-1-yl)-1,1,3,3-tetramethyluronium hexaflurophosphate (HATU), reacts with the free amino group of the solid support bound PNA, to form the amide bond. Capping of the PNA chain is accomplished with acetic anhydride in presence of N-methylpyrrolidone and pyridine (see e.g. Koch, T., et al. (1997) Improvements in automated PNA synthesis using Boc/Z monomers, *J. Peptide Res.* 49:80-88; Maison, W. (1991) Modified PNAs: A simple method for the synthesis of monomeric building blocks, *Bioorg. Med. Chem. Lett.,* 9: 581-584). The completed nucleobase polymer is removed from the solid support with a strong acid, for example hydrofluoric acid or trifluoromethane sulfonic acid. Other strategies for synthesizing PNAs include use of 9-fluorenylmethoxy carbonyl (Fmoc) or monomethoxytrityl protecting groups (Breipohl, G., et al., (1996), Synthesis of polyamide nucleic acids (PNAs) using a novel Fmoc/Mmt protecting group combination, *Bioorg. Med. Chem. Lett.* 6:665-670; Will, D. W. et al., The synthesis of polyamide nucleic acids using a novel monomethoxytrityl protecting group strategy, *Tetrahedron,* 51:12069-12082). Also available are PNA synthesis methods that use acid labile backbone protecting groups and base labile protecting groups for the exocyclic amines on the nucleobases (Gildea, B. D., U.S. Pat. No. 6,063,569).

Phosphonate nucleobase polymer analogs have H-phosphonate or alkylphosphonate internucleotide linkages. Nucleoside hydrogen phosphonate monomers used for the synthetic cycle is suitably protected by protecting groups normally used in the phosphoramidite synthetic scheme. The 5'-OH protecting group on the protected nucleoside bound to the solid support is removed with acid, such as dichloroacetic acid. In the coupling step, the nucleoside phosphonate monomer is activated, for example by pivaloyl chloride, 1-adamantane carbonyl chloride, or dipentaflurorophenyl carbonate, resulting in formation of an anyhydride that reacts with the free hydroxyl group on the solid support bound nucleoside. Capping is dependent on the type of activating reagent: use of unhindered activating reagent, such as paivaloyl chloride, may not require capping. Otherwise, capping is carried out with agents such as cyanoethyl-H-phosphonate or isopropyl-H-phosphonate. Unlike the phosphoramidite method set forth above, there is no oxidation of the phosphonate internucleotide linkage. Subsequent base treatment results in release of the completed nucleobase polymer from the solid support and removal of exocyclic protecting groups (see e.g. Seliger, H. (1990), Simultaneous synthesis of multiple oligonucleotides using nucleoside H-phosphonate intermediates, *DNA Cell Biol.* 9 (9) 691-96.

Nucleobase polymer analogs with alkylphosphonate internucleotide linkages are readily synthesized by several methods (Oligonucleotides and Analogues, A Practical Approach, Eckstein, F., Ed., IRL, Press, pp 137-154). By way of example, one exemplary method uses alkylphosphonamidite chemistry for the synthesis reactions. In this method, the nucleoside monomers used for the synthetic reactions have the exocyclic amines protected with suitable protecting groups, for example benzoyl, isobutyryl, or tert-butylphenoxyacetyl (t-BPA) groups, while the 5' hydroxyls are protected with a group such as a pixyl or dimethoxytrityl. (Sinha, N. D. et al. (1994), Synthesis of oligodeoxynucleoside methylphosphonates utilizing the tert butylphenoxyacetyl group for exocyclic amine protection, *Nucleic Acids. Res.* 22 (15): 3119-23; Hogrefe, R. I. et al. (1993), An improved method for synthesis and deprotection of methylphonate oligonucleotides, *Meth. Mol. Biol.* 20: 143-63; Zhou, Y. (1996), Solid phase synthesis of oligo-2-pyrimidone-2"deoxyribonucleotides and oligo-2-pyrimidone-2'-dexoriboside methylphosphonates, *Nucleic Acids. Res.,* 24: 2652-2659). Alkyphosphonamidites nucleoside reagents are prepared by phosphitylation, which involves reacting alkyldichlorophosphine, such a methyldichlorophosphine, and diisopropylamine with the appropriately protected nucleoside, thereby forming the 5'-protected nucleoside diisopropylmethylphosphonamidite. In the nucleobase polymer synthetic cycle, monomer bound to the solid substrate is deprotected (i.e. depixylated or detritylated) using acid, for example dichloroacetic acid, and reacted with the alkylphosphonamidite nucleoside reagent in presence of an activating agent, such a tetrazole. The free OH group attacks the phosphorous atom generating a methylphosphonite intermediate. Subsequent oxidation, which precedes the capping step, results in conversion to the methylphosphonate linkage. Capping is accomplished with acetic anhydride and dimethylaminopyridine.

Continued cycles of deprotection, coupling, oxidation and capping generate the desired oligonucleotide. Release from the solid support is affected by gentle deprotection, for example by treatment with ethylenediamine or hybrazine hydrate (see e.g. Hogrefe, R. I., An improved method for synthesis and deprotection of methylphosphonate oligonucleotides, In Protocols for Oligonucleotides and Analogs, *Meth. Mol. Biol, Vol* 20, Sudhir Agrawal, Ed., Humana Press, Inc. 1993). Other phosphonates, such as benzylphosphonates and aminoethylphosphonates, may also serve as internucleotide linkages (Samstag, W. et al., supra; Fathi, R., et al., supra).

Phosphorothioate and phosphorodithioate sequence nucleobase polymer analogs have sulphur substituted for oxygen as the non-bridging ligands bonded to the phosphorous atom. Synthesis of sequence-specific nucleobase polymers having phosphorothioate linkages is accomplished by a variety of methods, including H-phosphonate or phosphoramidite chemistry. One exemplary method uses phosphoramidite route to synthesis which permits introduction of the phosphorothioate linkage at any point in the nucleobase polymer synthetic scheme. In this method, the solid support bound nucleoside, which is protected at the 5' OH group with DMT, is deprotected and coupled to the incoming nucleoside phosphoramidite reagent in the presence of an activating agent, such as tetrazole. The β-cyanoethyl phosphite linkage is converted to the phosphorothioate with a sulfurization reagent, such as tetraethylthiuram disulfide (TETD), 3H-1,2-benzotdithiole-3-one-1,1,-dioxide (Beacauge reagent), or dibenzoyl tetrasulfide. Capping and release from solid support follows normal phosphoramidite chemistry procedures.

Dithioate analogs are prepared similarly to phosphorothioate except that a nucleoside 3' phosphorothioamidite is used. These synthons are generated, for example using a suitably protected nucleoside and tris(pyrrolidino)phosphine with a tetrazole activating agent. The resulting nucleoside diamidite is converted to the phosphorthioamidite with addition of 2,4 dichlorobenzylmercaptan (see e.g. Caruthers, M. H., et al. (1992) Chemical Synthesis of Deoxyoligonucleotides and Deoxyoligonucleotide analogs, *Meth. Enzy.* 211: 3-20). Reaction with deprotected, solid support bound nucleoside results in a nucleobase polymer with a thiophosphite triester linkage having the 2,4 dichlorobenzylmercaptan. Introduction of elemental sulfur yields the phosphorodithioate derivative. Deprotection is accomplished with thiophenol, which removes the 2,4 dichlorobenzylmercaptan, while treatment with base releases the oligonucleotide from the solid support.

Another nucleobase polymer analog embodied in the invention include nucleobase polymers with phosphate triester linkages. Synthesis of phosphate triester analogs use suitably protected (for example, benzoyl, isobutyryl, or isopropoxyacetyl protecting groups) O-alkyl-N,N diisopropylphosphoramidites. Alkyl groups include, but are not limited to, methyl, ethyl, trifluoroethyl, isopropyl, and neopentyl. In these embodiments, the chemical groups attached to the free ester are generally limited to those groups that are stable to all steps of conventional phosphoramidite chemistry, including deprotection steps and especially the procedures and conditions required for deprotection of protected amines, such that the resulting linkage is an uncharged phophotriester. Therefore, when such groups are alkyl, the group is, in certain embodiments, an alkyl other than methyl, for example, $C_2$-$C_6$ linear alkyl, since methyl phophotriesters tend to be less stable than higher-order alkyl phosphate triesters. Synthesis follows general phosphoramidite chemistry with variations in linkage to solid supports (e.g. oxalyl linker) and release from solid support following synthesis (e.g. 25% aq $NH_3$). Other nucleobase polymer analogs embodied in the invention include boranophosphates, and phosphofluoridate linkages. Methods for their synthesis are described in Protocols for Oligonucleotides and Analogs, *Meth. Mol. Biol., Vol* 20, Chapters 11 and 12, S. Agrawal, Ed., 1993, Humana Press, Inc., which is hereby incorporated by reference.

The sequence-specific nucleobase polymers embodied in the invention are not limited those with homogeneous internucleotide linkages; sequence-specific nucleobase polymers comprising more than one type of internucleotide linkage are also encompassed by the present invention. Thus, mobility-modified sequence-specific nucleobase polymers with combinations of phosphate diester, phosphate triester, phosphorothioate, and alkylphosphonate internucleoside linkages are all encompassed within the scope of the invention. Synthesis of sequence-specific nucleobase polymers having various combinations of internucleoside linkages are well known in the art, and references describing their synthesis are incorporated by reference herein (see e.g. Zhou, L. (1994), Synthesis of phosphorothioate-methylphosphonate oligonucleotide copolymers, *Nucleic Acids Res.* 22:453-456; Miller, P. S. (1999), Psoralen conjugated triplex forming oligodeoxyribonucleotide containing alternating methylphosphonate-phosphate diester linkages: synthesis and interactions with DNA, *Bioconjugate Chem.* 10:572-577)

In another aspect, the mobility-modified sequence-specific nucleobase polymers of the present invention comprise modified bases, a plethora of which have been described in the literature. Methods for synthesizing protected, modified bases and their incorporation into nucleobase polymers are well known in the art (see e.g. Connolly, B. A., Oligodexoynucleotides containing modified basis, In Oligonucleotide Analogs: A practical approach, supra). Base analogs incorporable into nucleic acids, include among others, deoxynapthosine, etheno adenosine and cytidine, 6-thioguanosine, 4-thiothymidine, 7-deaza purines, $N^6$-methyl adenosine, $O^6$-methyl guanosine, and 2-aminopurine.

In another embodiment of the present invention, the linkages used to attach the mobility-modifying polymer chain to the sequence-specific nucleobase polymer comprise various phosphoester analogs, other than phosphate diester linkages, including, but not limited to phosphate triester, alkylphosphonate, and phosphorothiate groups, or other suitable linkages. As set forth below, synthetic methods to generate various linkages can adopt synthetic strategies used in nucleobase polymer synthesis.

In one aspect, the linkage between the sequence-specific nucleobase polymer and the mobility-modifying polymer chain is an alkylphosphonate linkage. In one synthetic scheme, methyldichlorophosphine is reacted with diisopropylamine to form methylcholoro-N,N-diisopropylaminophosphine. Addition of suitably protected polymer, such as DMT pentaethylene oxide, in the presence of diisopropylamine generates methylphosophonamidite derivative with the attached polymer. Coupling of methylphosphoamidite derivative to a free hydroxyl group of a protected, solid support bound oligonucleotide occurs in the presence of activating agent, such as tetrazole, resulting in a methylphosphonite linkage. Subsequent oxidation, for example with iodine, results in conversion of the methylphosphonite to the methylphosphonate. Other phosphonate linking groups, such as benzylphosphonate, may be synthesized according to similar chemistry used to generate benzylphosphonate oligonucleotides.

In one embodiment, linking of the mobility-modifying polymer to the sequence-specific nucleobase polymer is accomplished through a phosphate triester linkage. Various routes of synthesis are available to form phosphate triester linkages between the mobility-modifying polymer and sequence-specific nucleobase polymer. In one embodiment, attaching the polymer chain to the nucleobase polymer follows phosphoramidite chemistry, as described in detail in Examples 1 and 2 and as illustrated in Schemes (II) and (III), below with ethylene oxide mobility-modifying polymers.

In Schemes (II) and (III), DMT represents dimethoxytrityl, iPr represents isopropyl and $R^2$ and b are as previously defined for structural formula (I).

when such groups are alkyl, the group is an alkyl other than methyl, for example, $C_2$-$C_6$ linear all,yl, since mono methyl phosphate triesters tend to be less stable than higher-order mono alkyl phosphate triesters. The embodiments of the invention also envision attachment of various modified alkyls having functional moieties, such as reporters, and ligand molecules. For example, β-cyanoethoxy phosphoramidites with conjugated functional moieties, including but not limited to biotin, psoralen, acridine dye, cholesterol, fluoresceine, rhodamine, 2,4 dinitrophenol, tris-(2,2'-bipyridine rutheium

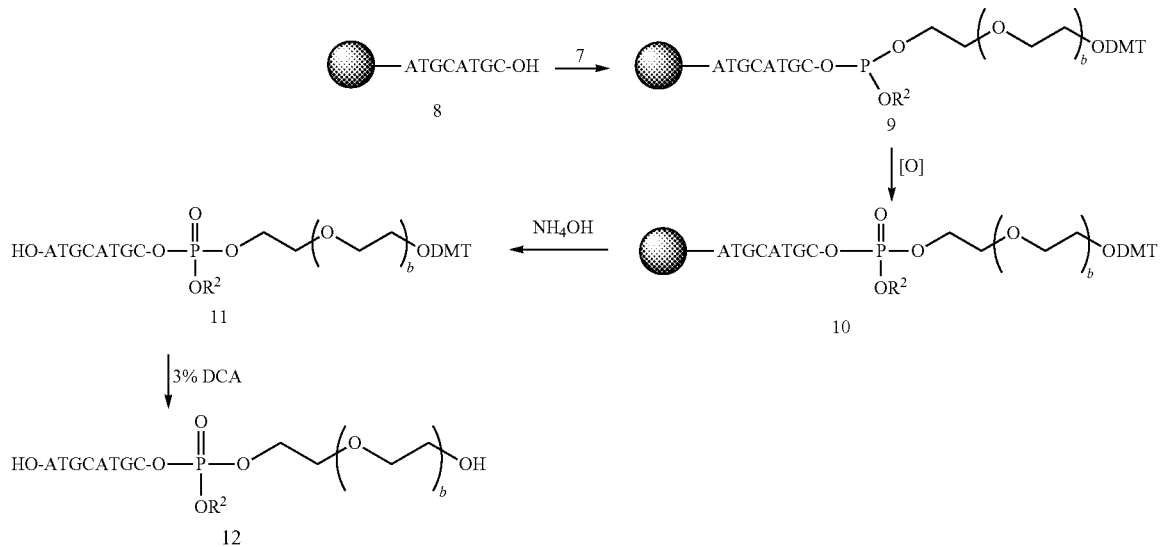

Scheme (II)

Referring to Scheme (II), the $R^2$-N,N-diisopropylaminophosphite 7 is reacted with the free 5' hydroxyl of a nascent nucleobase polymer 8, thereby generating a nucleobase polymer with a mobility-modifying polymer attached to the 5'-terminus by an $R^2$-phosphite triester linkage. Subsequent oxidation with iodine and deprotection with base converts the phosphite linkage to the $R^2$-phosphate triester linkage. The resultant mobility-modified sequence-specific nucleobase polymer 10 is cleaved off the solid support with base (e.g., $NH_4OH$, 55° C., 4 hr) to yield 11. Oligonucleotide 11 may be purified, for example by reverse-phase HPLC, and the remaining trityl group removed with weak acid (e.g., 3% dichloroacetic acid in $CH_2Cl_2$) to yield mobility-modified nucleobase polymer 12, which may be further purified, for example by chromatography on a PD 10 column. Alternatively, the trityl group may be removed prior to cleavage from the solid support and the resultant mobility-modified nucleobase polymer purified by conventional means.

As will be appreciated by those skilled in the art, when $R^2$ is an alkyl, the alkyl phosphoramidite reagent used to couple the mobility-modifying polymer segment to the nucleobase polymer may have linear or branched alkyls of various lengths. Where the phosphate ester is to remain uncharged, the chemical groups attached to the free ester are generally limited to those groups that are stable to all steps of conventional phosphoramidite chemistry, including deprotection steps and especially to the procedures and conditions required for the deprotection of protected amines, such that the resulting linkage is an uncharged phosphate triester. Therefore, (II) chelate (TBR), and histidines are well known in the art (see e.g. Smith, T. H. (1999), Bifunctional Phosphoramidite Reagents for the Introduction of Histidyl and Dihistidyl Residues into Oligonucleotides, *Bioconjugate Chem.*, 10: 647-652; Kenten, J. H. (1992), Improved electrochemiluminescent label for DNA probe assays: rapid quantitative assays of HIV-1 polymerase chain reaction products, *Clin. Chem*, 38:873-9). In general, these functional moieties are coupled to the phosphoramidite by a hydroxyl group present on polyoxide or aliphatic spacer arms conjugated to the derivatized moiety. Accordingly, the cognate alkyl phosphoramidite reagent having a derivatized, functional moiety and an attached mobility-modifying polymer can be readily synthesized by those skilled in the art by adapting the synthetic scheme provided in the instant application.

In some embodiments of the invention, multiple mobility-modifying polymers are attached to the nucleobase polymer. In one embodiment, the multiple mobility-modifying polymers are attached linearly to one another, either by way of uncharged linkages such as phosphate triester linkages (exemplified by the compounds of structural formula (II)), or by way of charged linkages such as negatively charged phosphate ester linkages (exemplified by the compounds of structural formula (III)). A method for synthesizing these types of mobility-modified nucleobase polymer polymers using standard phosphoramidite DNA chemistry is illustrated in Scheme (III), below.

Scheme (III)

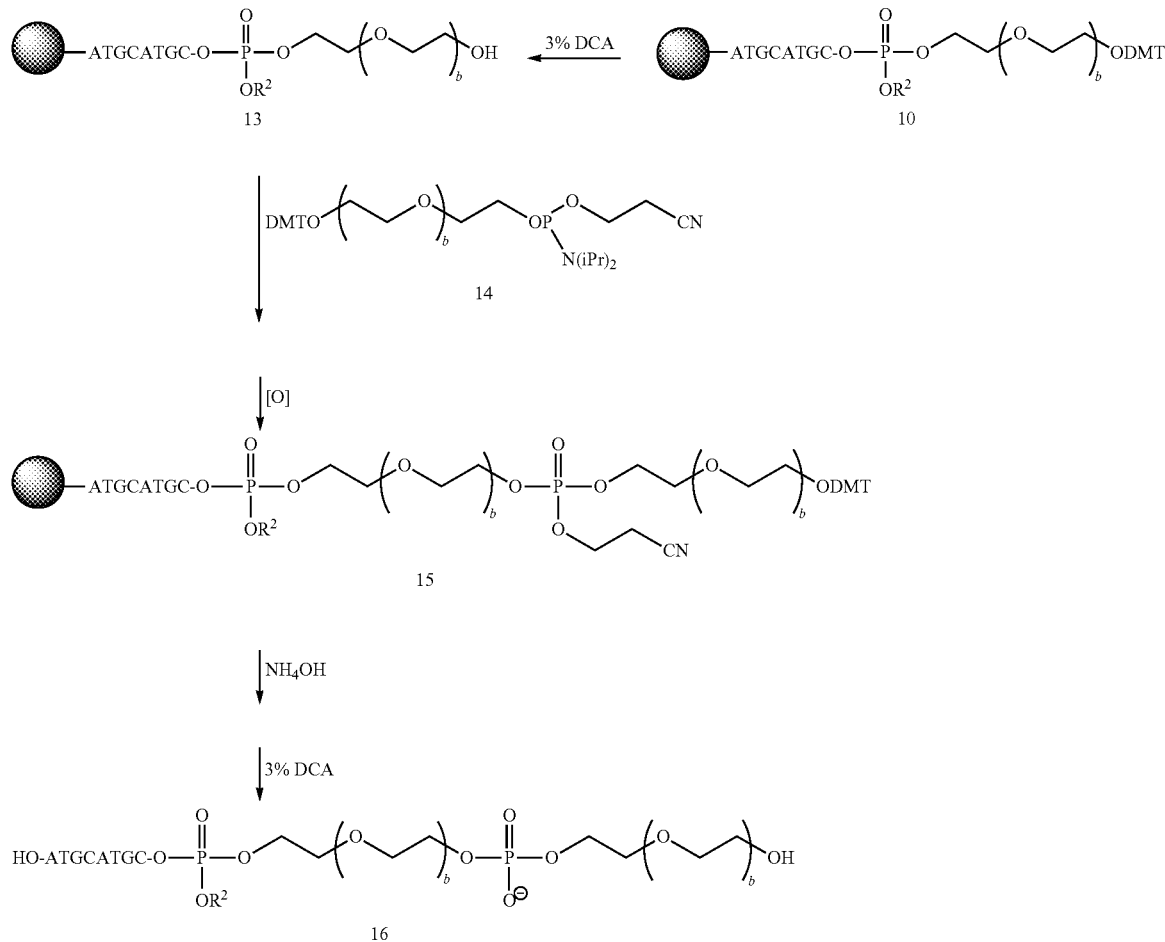

In Scheme (III), the various abbreviations and substituents are as defined for Schemes (I) and (II).

Referring to Scheme (III), support-bound nascent mobility-modified nucleobase polymer 10, which is synthesized as illustrated in Scheme (II), is treated with a weak acid, in this case 3% dicliloroacetic acid in dichloromethane, to remove the DMT protecting group, yielding support-bound compound 13. Support-bound compound 13 is coupled with DMT-protected polyethylene oxide β-cyanoethyl phosphoramidite reagent 14 in the presence of an activator such as tetrazole (typically 0.5 M in acetonitrile). Phosphoramidite reagent 14 may be prepared using standard syntheses. For example, phosphoramidite reagent 14 may be prepared according to Scheme (I) by substituting 2-cyanoethan-1-ol for compound 4. Oxidation, such as by reaction with a solution of iodine in tetrahydrofuran, 2,6-lutidine and water, yields compound 15. Cleavage from the resin, removal of any groups protecting the nucleobases and removal of the DMT protecting group yields mobility-modified nucleobase polymer 16. Additional polymers may be added by removing the DMT group from compound 15 and reacting it with phosporamidite reagent 7 or 14.

When the polymers are added sequentially, as for example in an automated DNA synthesis instrument, addition of additional mobility-modifying polymer chains is accomplished by deprotecting the OH protecting group on the terminus of the mobility-modifying polymer chain and repeating the cycles of coupling and oxidation as set forth above. Different mobility-modifying polymer chains may be added at each cycle to provide mobility-modified sequence-specific nucleobase polymers with distinctive ratios of charge to translational frictional drag.

Alternatively, the invention also contemplates mobility-modified nucleobase polymers in which the polymeric segment is a branched or dendritic structure. An exemplary method for synthesizing a phosphoramidite reagent that can be used in conjunction with standard DNA synthesis chemistry to synthesize such branched and/or dendridic mobility-modified nucleobase polymers is illustrated in Scheme (IV), below. In Scheme (IV), the various abbreviations and substituents are as defined for Schemes (I) and (II).

Scheme (IV)

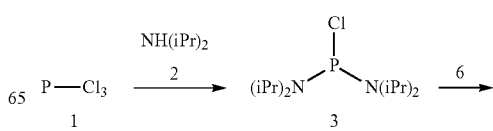

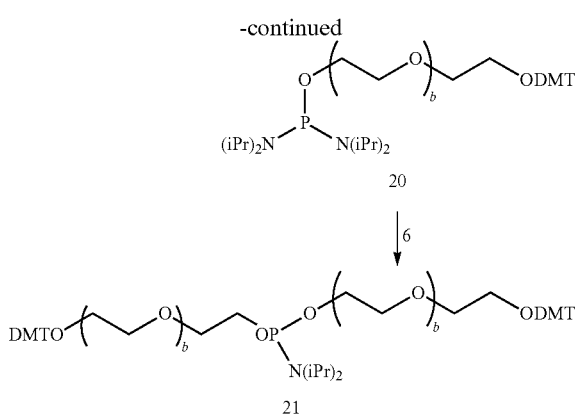

Scheme (IV) is similar to Scheme (J), except that a suitably protected polymer, such as DMT protected poly(alkylene oxide) 6 substitutes for alcohol 4, thereby forming bis(diisopropylamino)phosphite 20 having an attached polymer. Subsequent coupling of the second mobility-modifying polymer 6 generates a phosphoramidite reagent 21 having two mobility-modifying polymer chains. Coupling to the free hydroxyl group of a solid support bound sequence-specific nucleobase polymer and subsequent oxidation produces a branched mobility-modified sequence-specific nucleobase polymer.

Further addition of mobility-modified polymers are possible. The protecting group, for example DMT, on the mobility-modified polymers linked to the sequence-specific nucleobase polymer are removed with a weak acid, thus generating free hydroxyl groups. Reactions with derivatized N,N-diisopropylaminophosphite having an attached mobility-modifying polymer results in coupling of the additional mobility-modifying polymer units to the free hydroxyl groups. Coupling of any additional mobility-modifying polymer units may be limited to only one of the sequence-specific nucleobase polymer linked mobility-modifying polymers if the other linked mobility-modifying polymer has a nonreactive terminus. Alternatively, protecting the hydroxyl group of one nucleobase polymer linked polymer with protecting group that is stable to reagents used to remove DMT protecting groups, such as levulinyl, restricts coupling of any additional polymer units to the polymer protected with DMT (Iwai, S. (1988), 5'-Levulinyl and 2'-tetrahydrofuranyl protection for the synthesis of oligoribonucleotides, *Nucleic Acids Res*, 16:9443-56). This orthogonal strategy removes the protecting groups under mutually exclusive conditions.

The mobility-modifying phosphoramidite reagent of the present invention is also added to the 3'-end of a nucleobase polymer, according to Scheme V, which is depicted below:

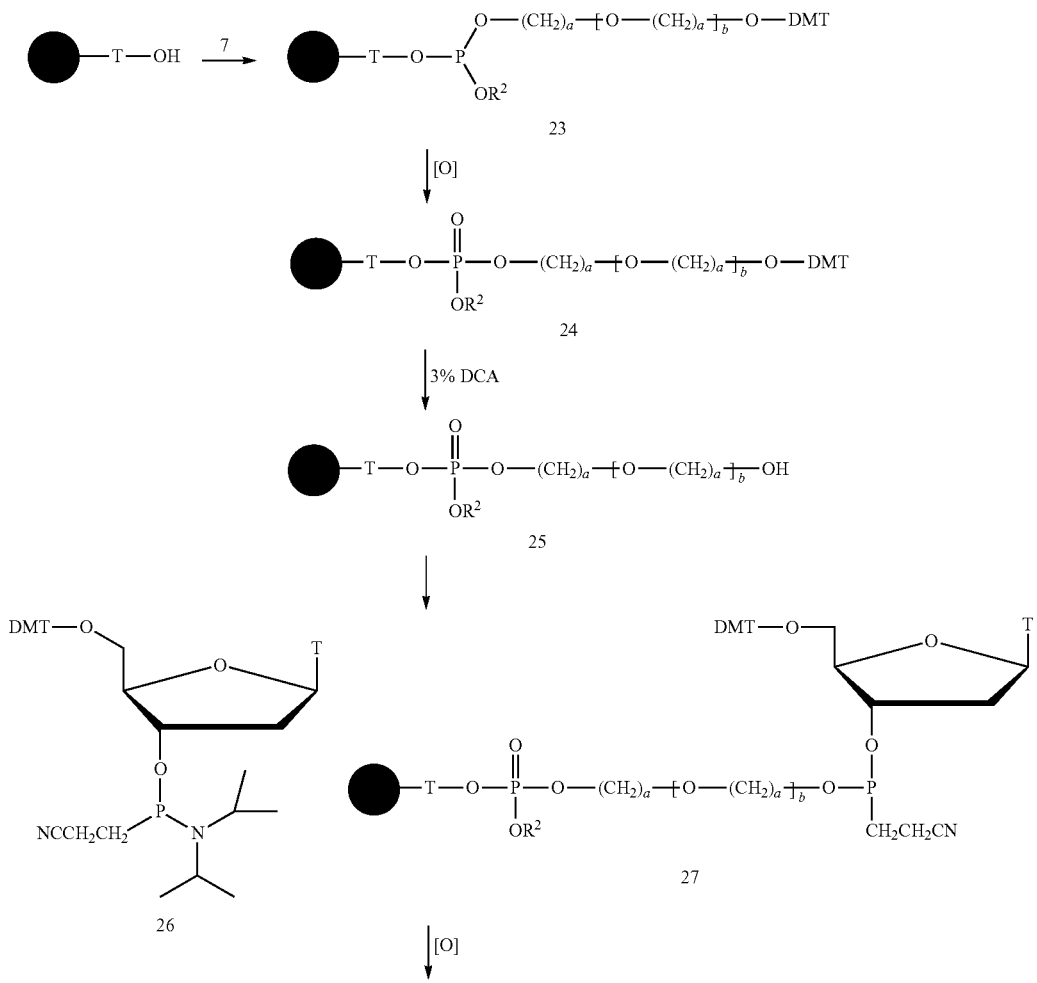

-continued

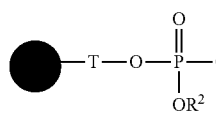 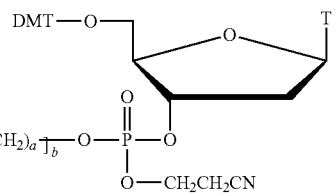

28

According to Scheme V, the mobility-modifying phosphoramidite reagent of the present invention is condensed with the free 5'-hydroxyl of a nucleobase monomer residue that is bound to a solid support (indicated in Scheme V as •), rather than the free 5'-hydroxyl of a nucleobase polymer bound to a solid support, as depicted in Scheme II. The first step in Scheme V generates a mobility-modified phosphoramidite polymer bound to the solid support via a nucleobase monomer linker (24). Mild acid treatment of 24 cleaves the DMT protecting group, thereby providing a free hydroxyl moiety upon which a nucleobase polymer is assembled via repeated cycles of condensation of activated, protected phosphoramidite nucleobase monomers using standard phosphoramidite chemistry, generally using an automated instrument. For example, eight further cycles are carried out, in which the following monomers are added, in order, A, T, G, C, A, T, G, and C.

After addition of the desired specific nucleobase polymer sequence to the surface-bound mobility-modifying polymer of the present invention, the mobility-modified sequence specific nucleobase polymer, in which the mobility-modifying polymer segment is carried at the 3'-end of the nucleobase polymer, is deprotected and cleaved from the solid support, yielding, continuing with the above illustrative synthesis, the product according to (29):

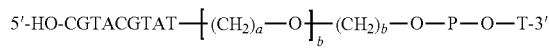

29

Alternatively, the substrate-bound molecule having a mobility-modifying polymer attached to the 3'-end of a nucleobase polymer, e.g. structure (28) of Scheme V, is subjected only to a mild acid treatment, removing the 5'-DMT moiety, and providing a free hydroxyl group on a substrate-bound nucleobase polymer structure, which would be analogous with (8) of Scheme II. Subsequent condensation with a mobility-modifying phosphoramidite reagent of the present invention would provide a sequence-specific nucleobase polymer having mobility-modifying polymer segments attached at both the 3'-end and the 5'-end.

In another embodiment, a mobility-modified nucleobase polymer is synthesized that comprises a mobility-modifying polymer attached to the 5'-end of a first nucleobase polymer as well as to the 3'-end of a second nucleobase polymer; that is the mobility-modifying polymer is "inserted" within a nucleobase polymer. In one non-limiting illustrative approach, a nucleobase polymer comprising a mobility-modifying polymer is synthesized according to Scheme II to provide intermediate (10), which comprises a first nucleobase polymer attached to a solid substrate and carrying a mobility-modifying polymer on the 5'-end of the first nucleobase polymer. Treatment of (10) with mild acid (3% DCA) to remove the DMT protecting group provides a structure, analogous to compound (25), onto which a second nucleobase polymer is added according to Scheme V, thereby providing a mobility-modified nucleobase polymer that comprises a first and a second nucleobase polymer in which a mobility-modifying polymer is attached to the 5'-end of the first nucleobase polymer as well as to the 3'-end of the second nucleobase polymer.

Therefore, the present invention also relates to a mobility-modified sequence-specific nucleobase polymer comprising a mobility-modifying polymer linked to the 3'-end of a first sequence-specific nucleobase polymer and to the 5'-end of a second sequence-specific nucleobase polymer according to Structural formula (IV):

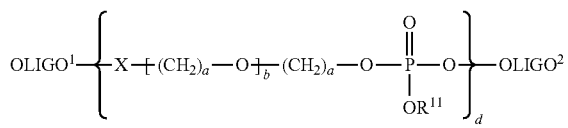

(IV)

or a salt thereof, wherein:
each $R^{11}$ is independently selected from the group consisting of hydrogen, alkyl comprising at least two carbon atoms, aryl, $(R^8)_3$ Si— where each $R^8$ is independently selected from the group consisting of linear and branched chain alkyl and aryl, base-stable protecting groups, $R^5$—X—$[(CH_2)_a$—$O]_b$—$(CH_2)_a$—, protecting group, reporter molecule, and ligand, with the proviso that at least one $R^{11}$ is not hydrogen;
each X is independently selected from the group consisting of O, S, NH and NH—C(O);
each a is independently an integer from 1 to 6;
each b is independently an integer from 0 to 40;
d is an integer from 1 to 200;
OLIGO$^1$ is a first sequence-specific nucleobase polymer; and
OLIGO$^2$ is a second sequence-specific nucleobase polymer.

OLIGO$^1$ and OLIGO$^2$ are sequence-specific nucleobase polymers, typically comprising at least 5 nucleobases. Moreover, where desired, mobility-modifying polymers of the present invention are also added to the 5'-end of the first nucleobase polymer and/or to the 3'-end of the second nucleobase polymer generally according to Schemes V and II, respectively, in addition to the mobility-modifying polymer positioned between the first and second nucleobase polymers, according to Structural formula V.

In yet another embodiment, the multiple mobility-modifying polymer chains may be synthesized independently and then attached in a single step to the sequence-specific nucleobase polymer. Various schemes may be devised for synthesizing the multiple mobility-modifying polymer chains independently of the sequence-specific nucleobase polymer. In one method, a mobility-modifying polymer chain such as pentaethylene oxide is protected with two different protecting groups, which are removable under mutually exclusive deprotecting conditions. One such orthogonal strategy is to protect the polymer with dimethoxytrityl at the hydroxyl group at one terminus and with levulinyl at the hydroxyl group of the other terminus. Alternatively, the polymer is attached to a solid support, analogous to attachment of nucleosides to solid supports for sequence-specific nucleobase polymer synthesis, through a bond that is resistant to conditions of DMT deprotection. In either case, treatment with weak acid preferentially removes the DMT protecting group, thereby exposing a free OH, while the other hydroxyl group remains protected. In the presence of an activating agent, such as tetrazole, a derivatized phosphoramidite reagent having an attached mobility-modifying polymer reacts with the hydroxyl group, resulting in coupling of the two polymers. Subsequent oxidation of the intermediate phosphite generates the β-cyanoethyl phosphate or phosphate triester linkage depending on the type of phosphoramidite reagent used for the coupling. Repeating the cycles of deprotection, coupling and oxidation generates linked mobility-modifying polymer chains, wherein the multiple mobility-modifying polymer chain is protected with DMT at one end and the other end with levulinyl. Deprotection by removal of the levuliny with hydrazine, or cleavage from the solid support bound polymer, exposes a free hydroxyl, which is then available for synthesizing the derivatized phosphoramidite reagent, for example an alkyl-N,N-diisopropylaminophosphite having an attached multiple mobility-modifying polymer chain. Coupling of the derivatized phosphoramidite reagent to a suitably protected nucleobase polymer results in attachment of the multiple mobility-modifying polymer chain to the sequence specific nucleobase polymer. Subsequent oxidation with iodine followed by treatment with base removes any protecting groups on the exocylic amines and β-cyanoethyl groups on the phosphates, with concomitant release of the mobility-modified sequence specific nucleic acid or nucleobase polymer from the solid support. Treatment with weak acid removes any remaining DMT protecting group on the mobility-modifying polymer.

5.6 METHODS OF USE

The present invention further encompasses methods of using mobility-modified sequence-specific nucleobase polymers, as well as compositions comprising a plurality of mobility-modified sequence-specific nucleobase polymers, wherein each said mobility-modified nucleobase polymer optionally has a structure independently selected from the group consisting of Structural formulae (II) and (III), and wherein each mobility-modified nucleobase polymer has a distinctive ratio of charge to translational frictional drag, to detect and characterize one or more selected nucleotide sequences within one or more target nucleic acids.

In one aspect, the present invention provides a method of detecting a plurality of sequences within one or more target nucleic acids, comprising contacting a plurality of mobility-modified sequence-specific nucleobase polymers, wherein each mobility-modified nucleobase polymer has a structure independently selected from the group consisting of Structural formulae (II) and (III), with one or more target nucleic acids, generally under conditions that distinguish those mobility-modified sequence-specific nucleobase polymers that hybridize to the target nucleic acid, and detecting those mobility-modified sequence-specific nucleobase polymers which have hybridized to the target nucleic acid.

In one aspect of this method, the target nucleic acids are immobilized. In this aspect, the immobilized target nucleic acids are contacted with mobility-modified sequence-specific nucleobase polymer probes, which further comprise a detectable label, under conditions that distinguish those probes having sufficient homology to hybridize to the target nucleic acid. Non-hybridized probes are washed away and hybridized probes, which are bound to the target nucleic acid immobilized on the membrane, are detected. Alternatively, the non-hybridized probes are washed away and hybridized probes are recovered as single-stranded products after denaturation of the base-paired structure formed between the mobility-modified sequence-specific nucleobase polymer probe and the immobilized target nucleic acid.

In another aspect of this method, the target nucleic acid, which may be immobilized, is contacted with a plurality of sequence-specific nucleobase polymer probes whereby two nucleobase polymer probes hybridize to adjacent sequences of the target nucleic acid such that the 5'-end of one nucleobase polymer probe, which generally will carry a 5'-phosphate moiety, abuts the 3'-end of the second nucleobase polymer probe, so that the two nucleobase polymer probes can be covalently joined to one another, in certain embodiments, with a DNA chemical or enzymatic ligating activity, to form a ligated product. In this aspect of the method, the ligated product is formed by the joining of two nucleobase polymer probes, at least one of which comprises a detectable label and at least one of which is a mobility-modified sequence-specific nucleobase polymer selected from the group consisting of Structural formulae (II) and (III), such that the ligated product has a distinctive ratio of charge to translational frictional drag. In a further aspect, three or more nucleobase polymer probes are hybridized to adjacent sequences of a target nucleic acid in such a manner that at least three nucleobase polymer probes can be covalently joined to form a ligated product, wherein at least one of the nucleobase polymer probes so joined comprises a detectable label, and at one of the nucleobase polymer probes so joined is a mobility-modified sequence-specific nucleobase polymer selected from the group consisting of Structural formulae (II) and (III) such that the ligated product has a distinctive ratio of charge to translational frictional drag. Generally, the ligated product, which is hybridized to the target nucleic acid, is released by denaturation, and the single stranded ligated product having a distinctive ratio of charge to translational frictional drag, is detected and analyzed, to provide information about the selected nucleotide sequence within the target nucleic acid.

This cycle of hybridization, joining, and denaturation, may be repeated in order to amplify the concentration of the ligated product formed. In this instance, the joining is optionally accomplished by means of a thermostable ligating enzyme. These reactions are conveniently carried out in thermal cycling machines with thermally stable ligases. (Barany, F. (1991), Genetic disease detection and DNA amplification using cloned thermostable ligase, *Proc. Natl. Acad Sci. USA* 88 (1): 189-193; Housby J. N. et al. (2000), Optimised Ligation of oligonucleotides by thermal ligases: comparison of *T. scotoductus* and *Rhotothermus marinus* DNA ligases to other thermophilic ligases, *Nuc. Acids Res.* 28 (3): E10).

Furthermore, additional nucleobase polymers, which together are sufficiently complementary to the ligated product to hybridize thereto and be covalently joined to one another as above, are also included, thereby affording geometric amplification of the ligated product, i. e., a ligase chain reaction (Wu, D. Y. and Wallace B. (1989), The ligation amplification reaction (LAR)-Amplification of Specific DNA sequences using sequential Rounds of Template Dependent Ligation, *Genomics* 4:560-569; Barany, (1991), *Proc Natl. Acad. Sci. USA*, 88:189; Barany, (1991), PCR Methods and Applic., 1:5). To suppress unwanted ligation of blunted ended hybrids formed between complementary pairs of the mobility-modified and second oligonucleotides and the second pair of oligonucleotides, conditions and agents inhibiting blunted ended ligation, for example 200 mM NaCl and phosphate, are included in the ligation reaction.

The product of such a ligase chain reaction therefore is a double stranded molecule consisting of two strands, each of which is the product of the joining of at least two sequence-specific nucleobase polymer probes. Accordingly, in yet another aspect of the present invention, at least one of the sequence-specific nucleobase polymers incorporated within the ligase chain reaction product comprises a detectable label, and at one of the sequence-specific nucleobase polymers is a mobility-modified sequence-specific nucleobase polymer selected from the group consisting of Structural formulae (II) and (III) such that the ligase chain reaction product has a distinctive ratio of charge to translational frictional drag.

In another aspect of the oligonucleotide ligase assays described above, mismatches, i.e. non-complementary nucleobases, existing between selected nucleotide sequences within the target nucleic acid and either or both of the mobility-modified sequence-specific nucleobase polymer and the second oligonucleotide interfere with the ligation of the two nucleobase polymers either by preventing hybrid formation or preventing proper joining of the adjacent terminal nucleotide residues. Thus, when the binding conditions are chosen to permit hybridization of both nucleobase polymers despite at least one mismatch, the formation of a mobility-modified ligated product reveals the sequence of the selected nucleotide sequence as it exists within the target nucleic acid, at least with respect to the terminal, adjacent residues of the two nucleobase polymers. Those skilled in the art are well versed in selecting appropriate binding conditions, such as cation concentration, temperature, pH, and oligonucleotide composition to selectively hybridize the nucleobase polymers to the selected nucleotide sequences within the target nucleic acid.

Since the base pairing of terminal adjacent residues affects ligation, in one embodiment the nucleobase polymer providing the 3' terminal nucleobase involved in the joining reaction is designed to be perfectly complementary to the target sequence while the nucleobase polymer providing the 5' terminal nucleobase residue involved in the joining reaction is designed to be perfectly complementary in all but the 5' terminal nucleobase. In another embodiment, the nucleobase polymers are designed such that the nucleobase polymer providing the 3' terminal nucleobase is perfectly complementary except for the 3' terminal nucleobase residue while the oligonucleotide providing the 5' terminal nucleobase is perfectly complementary (Wu, D. Y. and Wallace, B.,(1989), Specificity of nick-closing activity of bacteriophage T4 DNA ligase, *Gene* 76: 245-254; Landegren, U. et al. (1988) A ligase mediated gene detection technique, *Science* 2241: 1077-1080).

In a modification of the method set forth above, the mobility-modified sequence-specific nucleobase polymer probe comprises a nucleobase sequence that is complementary to the target sequence, but comprises a non-terminal mismatch with respect to non-target sequences. In this aspect of the invention, the composition of the mobility-modified sequence-specific nucleobase polymer probe and the nature of the experimental conditions are such that the probe will only hybridize to the target sequence. In this embodiment for example, a second nucleobase polymer that hybridizes to the target nucleobase, either upstream or downstream of the hybridized mobility-modified sequence-specific nucleobase polymer probe, may be ligated to that probe to form the ligated, mobility-modified product that is diagnostic of the presence of the target nucleotide sequence.

In a further modification of the embodiment set forth above, the mobility-modified sequence-specific nucleobase polymer is hybridized to a selected nucleotide sequence within a target nucleic acid that is immediately adjacent to the site of interest. A second sequence-specific nucleobase polymer is hybridized to the selected region within the target nucleic acid such that the hybridized oligonucleotides are separated by a gap of at least one nucleotide residue. In another embodiment, the length of the gap is a single nucleotide residue representing a single polynucleotide polymorphism in the target nucleic acid. Following hybridization, the complex, which consists of the two nucleobase polymers hybridized to the target nucleic acid, is treated with a nucleic acid polymerase in the presence of at least one deoxyribonucleoside triphosphate. If the deoxyribonucleoside triphosphate(s) provided are complementary to the target polynucleotide's nucleotide residues which define the gap, the polymerase fills the gap between the two hybridized nucleobase polymers. Subsequent treatment with ligase joins the two hybridized oligonucleotides to form a ligated, mobility-modified product, which can, in one embodiment, be separated from the template by thermal dissociation, thereby providing a diagnostic product having a distinctive ratio of charge to translational frictional drag. This diagnostic product will generally comprise a reporter molecule, which may be included within either of the ligated nucleobase polymers, be attached to the one or more nucleobases added by the polymerizing activity, or be added subsequent to the covalent joining of the nucleobase polymers, using methods disclosed infra. By treating with polymerase in the presence of fewer than four nucleoside triphosphates, the nucleotide residues comprising the gap may be determined. Further amplification of ligated mobility-modified product is achieved by repeated cycles of denaturation, annealing, nucleic acid polymerase gap filling, and ligation in the presence of at least one of the nucleoside triphosphates.

If the treatment with nucleic acid polymerase occurs in the presence of one labeled nucleoside triphosphate or a mixture containing one labeled and 3 unlabeled nucleoside triphosphates, ligated mobility-modified products comprising at least one incorporated, labeled nucleoside are readily detected upon electrophoretic separation of the labeled mobility-modified ligated products. Modification of the nucleotide mixture to one having one labeled nucleoside triphosphate and three chain terminating nucleoside triphosphates suppresses unwanted ligation of oligonucleotides with incorrectly incorporated nucleotide residues.

Mobility-modified sequence-specific nucleobase polymers of the present invention are also useful as primers for nucleic acid sequence analysis by the chain termination method, a method well known to those skilled in the art. In one embodiment, mobility-modified nucleobase polymers are hybridized to target nucleic acid and extended by a nucleic acid polymerase in the presence of a mixture of nucleoside triphosphates and a chain terminating nucleoside triphosphate. The polymerase reaction generates a plurality of chain terminated mobility-modified nucleic acids fragments, which are separated, for example by capillary electrophoresis. Chain termination by the incorporated chain terminating nucleoside triphosphate identifies the 3' terminal residue of the terminated nucleic acid fragment.

For the purposes of detecting the chain terminated species, various substituents of the mobility-modified nucleic acid fragments are amenable to conjugation with detectable reporter molecules. These include the functional groups on the mobility-modifying polymer, the phosphate triester group linking the mobility-modifying polymer to the sequence-specific nucleobase polymer, or nucleoside triphosphate precursors, including the chain terminators, incorporated into the nucleic acid. Detectable reporter molecules may be radioactive, chemiluminescent, bioluminescent, fluorescent, or ligand molecules. In one embodiment, the detectable label is a fluorescent molecule, for example fluorescein isothiocyanate, Texas red, rhodamine, and cyanine dyes and derivatives thereof. In another embodiment, the fluorescent dyes are mobility-modified to reduce the variations in electrophoretic mobility of nucleic acids caused by the fluorescent label (see e.g. Ju, J. et al. (1995). Design and synthesis of fluorescence energy transfer dye-labeled primers and their application for DNA sequencing and analysis, *Anal. Biochem.* 231: 131-40; Metzker, et al. (1996) Electrophoretically uniform fluorescent dyes for automated DNA sequencing, *Science* 271: 1420-22; Hung, S. C. et al. (1997) Comparison of fluorescence energy transfer primers with different donor-acceptor dye combinations, *Anal. Biochem.* 252: 77.88; Ti, O. et al. (1998) The influence of fluorescent dye structure on the electrophoretic mobility of end-labeled DNA, *Nucleic Acids Res,* 26: 2797-2802)

In one embodiment, the mobility-modified sequence-specific nucleobase polymers of the present invention are used within a format for sequencing selected regions within a target polynucleotide wherein one of four spectrally resolvable fluorescent molecules is used to label the nucleic acid fragments in reactions having one of four chain terminating nucleoside triphosphates. In another aspect of this embodiment, the mobility-modified sequence-specific nucleobase polymers of the present invention are used for sequencing selected regions within a target polynucleotide wherein one of four spectrally resolvable fluorescent molecules is used to label an oligonucleotide primers in a reaction containing one of four chain terminating nucleoside triphosphates. Thus, in both aspects of this embodiment, detecting the fluorescent color of the chain terminated nucleic acid fragment identifies the 3' terminal nucleotide residue. Separation of the chain-terminated products by electrophoresis, typically in a single gel lane or capillary, along with simultaneous on-line detection of four spectrally resolvable fluorescent molecules allows rapid sequence determination from the colors of the separated nucleic acid fragments (Prober, J. M. et al. (1985), A System for Rapid DNA Sequencing with Fluorescent Chain Terminating Dideoxynucleotides, *Science* 238: 336-341; Karger, A. E. et al., (1991), Multiwavelength Fluorescence Detection for DNA Sequencing Using Capillary Electrophoresis, *Nucleic Acids Res.* 19 (18):4955-62).

When the nucleotide sequence of interest is a small region of the target nucleic acid, for example a site including single nucleotide polymorphism, modified sequencing formats, optionally, are used. In one such embodiment, a mobility-modified sequence-specific nucleobase polymer is hybridized in a sequence-specific manner such that the 3'-terminal nucleotide residue of the mobility-modified sequence-specific nucleobase polymer is immediately adjacent to the site of interest. The hybridized nucleobase polymer is extended by a nucleic acid polymerase in the presence of at least one chain terminating nucleoside triphosphate extends the oligonucleotide by one nucleotide if the chain terminating nucleotide is complementary to the target nucleic residue immediately downstream of the 3'-terminus of the hybridized mobility-modified sequence-specific nucleobase polymer. Separation and detection of the extended, mobility-modified sequence-specific mobility-modified sequence-specific nucleobase polymer provides the identity of the residue immediately adjacent to the hybridized mobility-modified sequence-specific nucleobase polymer primer. In this embodiment, the use of a plurality of different mobility-modified sequence-specific nucleobase polymers permits the simultaneous detection and analysis of a plurality of target sequences in a single separation.

Detecting the extended primer is accomplished by including a reporter molecule conjugated to the extended, mobility-modified sequence-specific nucleobase polymer are used as primers in the same maimer as described above for standard sequencing reactions. Thus, in one embodiment, the chain terminating nucleoside triphosphate is labeled with one of four spectrally resolvable fluorescent molecules such that the fluorescent label uniquely identifies the chain terminating nucleotide. The composition of the residue immediately adjacent to the hybridized oligonucleotide primer is then readily ascertained from the colors of the extended oligonucleotide primer. As will be apparent to those skilled in the art, this modified sequencing format is adaptable to other mixtures of fluorescently labeled chain terminating nucleoside triphosphates. Thus the embodiments encompass nucleotide combinations having two or four chain terminating nucleoside triphosphates wherein only one chain terminator is labeled with one of four resolvable reporter labels. Mixing the products of the extension reactions, followed by separation and detection of the extended products in a single gel lane or capillary provides the ability to determine all possible sequence variations at the nucleotide residue adjacent to the hybridized primer. Further increase in sensitivity of the methods are possible by using substantially exonuclease-resistant chain terminators, such as those which form thio-ester internucleotide linkages, to reduce removal of incorporated chain terminators by polymerase associated exonuclease.

In another embodiment, mobility-modified sequence-specific nucleobase polymers are used in polymerase chain reactions (PCR) to detect and amplify selected nucleotides within one or more target nucleic acids (Mullis, K., U.S. Pat. No. 4,683,202; Saiki, R. K., et al., Enzymatic Amplification of β-Globin Genomic Sequences and Restriction Site Analysis for Diagnosis of Sickle Cell Anemia, In *PCR: A practical approach*, M. J. McPherson, P. Quirke, and G. R. Taylor, Eds., Oxford University Press, 1991). In this aspect of the present invention, the detection method involves PCR amplification of nucleotide sequences within the target nucleic acid. In this aspect, a target nucleic acid, which may be immobilized, is contacted with a plurality of sequence-specific nucleobase polymers, two of which hybridize to complementary strands, and at opposite ends, of a nucleotide sequence within the target nucleic acid. Repeated cycles of extension of the hybridized sequence-specific oligonucleotides, optionally by a thermo-tolerant polymerase, thermal denaturation and dissociation of the extended product, and annealing, provide a geometric expansion of the region bracketed by the two nucleobase polymers. The product of such a polymerase chain reaction therefore is a double-stranded molecule consisting of two strands, each of which comprises a sequence-specific nucleobase polymer probe. In this aspect of the present invention, at least one of the sequence-specific oligonucleotides is a mobility-modified sequence-specific nucleobase polymer selected from the group consisting of Structural formulae (II) and (III) such that the double stranded polymerase chain reaction product has a distinctive ratio of charge to translational frictional drag. The polymerase chain reaction product formed in this aspect of the invention further comprises a label, which may be incorporated within either of the sequence-specific nucleobase polymer probes used as primers, or it may be incorporated within the substrate deoxyribonucleoside triphosphates used by the polymerizing enzyme. In yet another aspect, the polymerase chain reaction product formed is analyzed under denaturing conditions, providing separated single stranded products. In this aspect, at least one of the single stranded products comprises both a label and a mobility-modified sequence-specific nucleobase polymer primer selected from the group consisting of Structural formulae (II) and (III) such that the single-stranded product derived from double stranded polymerase chain reaction product has a distinctive ratio of charge to translational frictional drag. As is well known in the art, such a single-stranded product may also be generated by carrying out the PCR reaction with limiting amounts of one of the two sequence-specific nucleobase polymer probes used as a primer. By using distinctive mobility-modified sequence-specific nucleic acids or nucleobase polymers as primers, the PCR reaction can detect many selected regions within one or more target polynucleotides in a single assay by allowing separation of one PCR product from another. Moreover, those skilled in the art will recognize that using various combinations of nucleobase polymer primers provides additional ways to generate distinctive mobility-modified PCR products. For example, a combination of a mobility-modified nucleobase polymer and a second nucleobase polymer primer pair in the PCR reaction generates a PCR product with a single mobility-modified strand. On the other hand, a combination of a mobility-modified nucleobase polymer and a second nucleobase polymer, which is also mobility-modified, generates a PCR product having both strands that are mobility-modified, thus distinguishing itself from the PCR product with one mobility-modified strand. Thus, by varying the type of mobility-modifying group and the nucleic acid strands that are mobility-modified, the embodiments enlarge the capacity to detect multiple target segments.

Detection of the PCR products may be accomplished either during electrophoretic separation or after an electrophoretic separation. Intercalating dyes such as ethidium bromide, ethidium bromide dimers, SYBR® Green, or cyanine dye dimers such as TOTO, YOYO and BOBO are available for post separation detection (Haugland, R. P. Handbook of Fluorescent Probes and Research Chemicals, $6^{th}$ ed, Molecular Probes, Inc., 1996). Alternatively, the PCR products further comprise reporter molecules, including but not limited to radioactive, chemiluminescent, bioluminescent, fluorescent, or ligand molecules that permit detection either during or subsequent to an electrophoretic separation. Methods for labeling the mobility-modified PCR products follow the general schemes presented for labeling in other methods described infra.

Detecting a selected nucleotide sequence within a target nucleic acid by PCR amplification also encompasses identifying sequence variations within segments of the target nucleic acid. These variations include, among others, single nucleotide polymorphisms and polymorphisms in variable nucleotide tandem repeats (VNTR) and short tandem repeats (STR), such as those defined by sequence tag sites (STS). Identifying polymorphic loci are of particular interest because they are often genetic markers for disease susceptibility (see e.g. Gastier, J. M., (1995), Hum Mol Genet, 4(10): 1829-36; Kimpton, C. P., (1993), Automated DNA profiling employing multiplex amplification of short tandem repeat loci, PCR Methods Appl., 3(1): 13-22). If the polymorphisms relate to variations in VNTR or STR, sequences, direct analysis of PCR, products without further treatment suffices for detecting polymorphisms since the products differ in nucleotide length. The presence of mobility-modified PCR products, however, expands the capability of the PCR analysis to detect multiple polymorphic loci in a single reaction.

If the polymorphisms relate to single nucleotide differences, the variations are detectable by conducting PCR reactions using nucleobase polymer primers designed to have mismatches with the selected nucleic acid sequence within a target nucleic acid. The presence of intentional mismatches within the duplex formed by hybridization of the nucleobase polymer primer and the selected nucleic acid sequence within the target nucleic acid affects the thermal stability of those duplex molecules, which is reflected in the $T_m$ of those structures and thus, under selected conditions, results in preferential amplification of one target segment as compared to another. Such allele-specific polymerase chain reactions permit identification of mutations in single cells, or tissues containing a low copy number of one selected nucleotide sequences amongst a high background of other nucleotide sequences within one or more target nucleic acids (Cha, R. S., (1993), Mismatch amplification mutation assay (MAMA): application to the c-H-ras gene., PCR Methods Appl., 2(1) 14-20; Glaab., W. E. et al, (1999), A novel assay for allelic discrimination that combines fluorogenic 5' nuclease polymerase chain (TaqMan®) and mismatch amplification mutation., Mutat. Res. 430: 1-12).

In yet another aspect, single nucleotide differences are distinguished through analysis of higher order conformations of single stranded nucleic acids that form in a sequence dependent manner. In this embodiment, single stranded nucleic acids are generated by dissociating the PCR products into single strands, or by preferentially amplifying one strand by using limiting amounts of one primer in the PCR reaction (i.e. single-sided PCR). Under selected conditions, the single stranded nucleic acids are allowed to form higher order structures by intramolecular hydrogen bonding of the single stranded nucleic acid. Those skilled in the art are well versed in defining such permissive conditions (i.e. temperature, denaturant concentration, pH, cation concentration etc.) for forming the higher order structures. These conformations, which are sequence dependent and which therefore can be extremely sensitive to single nucleotide changes, affect the electrophoretic mobility of the nucleic acid, and thus reveal variation in a selected nucleotide sequence within a target nucleic acid by their unique electrophoretic mobility profiles. To enhance formation of higher order structures modifications are introduced into the nucleobase polymer primers used for the PCR reactions. For example, a nucleobase polymer primer is engineered with additional bases complementary to a part of the selected nucleotide sequence within a target nucleic acid containing the sequence variation, such that higher order conformations form when the additional bases on the nucleobase polymer primer "snapback" or re-anneal to the normal sequence but not to variant sequences (Wilton, S. D. (1998), Snapback SSCP analysis: engineered conformation changes for the rapid typing of known mutations, Hum. Mutat. 11(3): 252-8). Since the reliability of detecting single nucleotide variations is affected by size of the single stranded nucleobase polymer, conformation analysis using mobility-modified sequence-specific nucleobase polymers, with each having a distinctive ratio of charge to translational frictional drag, permits detection of a plurality of selected nucleotide sequences within a target nucleic acid while maintaining the optimal length needed for forming higher order structures (Sheffield, V. C., (1993), The sensitivity of single stranded conformation polymorphism analysis for the detection of single base substitutions, *Genomics* 16 (2): 325-32).

In yet another aspect of the invention, mobility-modified sequence-specific nucleobase polymers are cleaved to detect selected nucleotide sequences within one or more target nucleic acids. In one such embodiment, mobility-modified sequence-specific nucleobase polymers are hybridized to selected nucleotide sequences within one or more target nucleic acids. In another embodiment, mobility-modified PCR products comprising at least one mobility-modified sequence-specific nucleobase polymer serve as substrates for sequence-specific enzymes, such as restriction enzymes. Digestion of the substrates by the enzymes creates cleaved products having a distinctive ratio of charge to translational frictional drag, which provides information about sequence composition of the target polynucleotides. This form of restriction fragment length polymorphism (RFLP) analysis is well known to those skilled in the art (see e.g., Kidd, I. M., (1998), A multiplex PCR assay for the simultaneous detection of human herpesvirus 6 and human herpesvirus 7, with typing of HHV-6 by enzyme cleavage of PCR products, *J. Virol. Methods* 70 (1): 29-36; Gelernter, J., (1991), Sequence tagged sites (STS) Taq I RFLP at dopamine beta-hydroxylase, *Nucleic Acids. Res.* 19 (8): 1957).

In another aspect, mobility-modified nucleobase polymers hybridized to selected nucleotide sequences within a target nucleic acid, wherein there is at least one nucleobase not complementary to the corresponding nucleobase in the target nucleic acid, are treated with agents that specifically cleave the non-base-paired nucleotide residues. Generally, the unpaired residue occurs on the hybridized mobility-modified nucleobase polymer (Bhattacharya, et al., (1989), *Nucleic Acids. Res.* 17, 6821-6840). Although chromosomal DNA may serve as the target nucleic acids, target nucleic acids are cloned DNA fragments comprising selected nucleotide sequences of a target nucleic acid, or PCR amplification products comprising selected nucleotide sequences of a target nucleic acid.

Cleavage may be accomplished with either chemical or enzymatic reagents. In chemical cleavage reactions, the hybrids containing at least one non-complementary nucleobase, are treated with chemicals which specifically modify the unpaired residue, rendering the internucleotide linkage of the modified nucleoside susceptible to hydrolysis. Suitable chemical agents include but are not limited to carbodiimide, osmium tetraoxide, hydroxylamine or potassium permanganate/tetraethylammonium chloride (Ellis, T. P., et al., (1998), Chemical cleavage of mismatch: a new look at an established method, *Hum Mutate* 11: 345-53; Roberts, E., (1997), Potassium permanganate and tetraethylammonium chloride are safe and effective substitute for osmium tetraoxide in solid phase fluorescent chemical cleavage mismatch, *Nucleic Acids. Res.* 25: 3377-78). The use of potassium permanganate/tetraethylammonium chloride rather than osmium tetraoxide enhances cleavage at T/G mismatched pairs.

Enzymatic cleaving reagents encompass a variety of nucleases which recognize unpaired regions. These include but are not limited to single stranded specific nucleases such as S1 nuclease from *Aspergillus oryzue*, P1 from *Penicillum citrinum*, and mung bean nuclease (Shenk, et al., (1975) *Proc. Natl. Acad. Sci. USA* 72 989-93). Although these nucleases are less reactive towards single nucleotide mismatches, they can digest unpaired residues created by longer insertions and deletions (Dodgson, J. B. et al., (1977), Action of single-stranded specific nucleases on model DNA heteroduplexes of defined size and sequence, *Biochemistry,* 16:2374-49). Cel 1 and SP endonucleases show activity toward unpaired nucleotide residues resulting from nucleotides sequence variations comprising deletions, insertions, and missense mutations, within selected nucleotide sequences of target nucleic acids. (Oleykowski, C. A., (1998) Mutation detection using a novel plant endonuclease, *Nucleic Acids. Res.* 26: 4597-602; Yeung, A. T., U.S. Pat. No. 5,869,245). Resolvases from various sources, such as bacteriophage and yeast, represent yet another class of cleaving enzymes useful in this embodiment of the invention. Representative examples of resolvases include but are not limited to phage encoded T4 endonuclease VII and T7 endonuclease I, both of which cleave at mismatches (Cotton, R. G. H., U.S. Pat. No. 5,958,692; Solaro, et al., (1993), Endonuclease VII of Phage T4 Triggers Mismatch Correction in vitro. *J. Mol. Biol.* 230: 868-877; (Chang, D. Y. et al., (1991), Base mismatch specific endonuclease activity in extracts from *Saccharomyces cerevisiae*; Nucleic Acids Research 19 (17): 4761-66).

In another aspect, of the present invention encompasses methods that prevent cleavage at unpaired residues. Proteins, including but not limited to the MutS protein of *E. coli.*, bind to sites of single nucleotide mismatches in duplex nucleic acid structures (Su, S. S. et al., (1986), *Escherichia coli* mutS encoded protein binds to mismatched DNA base pairs, *Proc. Natl Acad. Sci. USA* 83: 5057-5061). The MutS protein is pair of the methylation directed *E coli*. MutH/S/L mismatch repair system, homologs of which are present in other bacteria, yeast and mammals (Eisen, J. A., (1998), A phylogenetic study of the MutS family of proteins, *Nucleic Acids. Res.* 26: 4291-300; Alani, E. (1996), The *Saccharomyces cerevisiae* Msh2 and Msh6 proteins form a complex that specifically binds to duplex oligonucleotides containing mismatched DNA base pairs, *Mol. Cell Biol.* 16: 5604-15; Modrich, P. et al., (1996), Mismatch repair in replication fidelity, genetic recombination and cancer biology, *Annu. Rev. Biochem.* 65: 101-33). Therefore in one embodiment of the invention, duplex structures comprising at least one non-base-paired nucleobase unit formed by hybridization of a mobility-modified sequence-specific nucleobase polymer with a selected nucleotide sequence within a target nucleic acid, are treated with mismatch binding proteins such as MutS and then exposed to one or more exonucleases which degrade the duplex strands in a unidirectional fashion. A bound mismatch binding protein inhibits further action of the exonuclease on the strand containing the mismatch, thereby providing nucleic acid products of defined length and which possess a distinctive ratio of charge to translational frictional drag (Ellis, L. A., (1994), MutS binding protects heteroduplex DNA from exonuclease digestion in vitro: a simple method for detecting mutations, *Nucleic Acids Res.* 22 (13):2710-1; Taylor, G. R., U.S. Pat. No. 5,919,623). Unidirectional exonucleases suitable for use in this assay include, but are not limited to exonuclease III, bacteriophage λ exonuclease, and the 3' to 5' exonucleases of T7 DNA polymerase, T4 DNA polymerase, and Vent® DNA polymerase.

In yet another aspect, a mobility-modified sequence-specific nucleobase polymer is used in a cleavage based method of detecting selected nucleotide sequences within a target nucleic acid may be a DNA-RNA-DNA nucleobase polymer, where an internal RNA segment is flanked by DNA segments. This tripartite mobility-modified sequence-specific nucleobase polymer is hybridized to a selected nucleotide sequence within a target nucleic acid at a temperature below the $T_m$ of the overall, i.e. tripartite nucleobase polymer. Digestion of this duplex structure with an appropriate RNase, hydrolyzes only the RNA portion of the DNA-RNA-DNA nucleobase polymer when hybridized to a DNA template. In one embodiment, the RNase is a thermo-stable RNase H (Bekkaoui, F., (1996), Cycling probe technology with RNase H attached to an oligonucleotide, *Biotechniques,* 20 (2): 240-8). If the temperature of the reaction maintained above the $T_m$ of the flanking DNA segments remaining after digestion of the internal RNA segment, those DNA segments dissociate, thus allowing another DNA-RNA-DNA oligomer to associate with the target polynucleotide. Repeated hybridization, RNA cleavage, and dissociation of the flanking DNA segments amplifies the level of detectable dissociated DNA segments. The reaction temperature, in one embodiment, is held constant during the amplification process, thus obviating any need for thermal cycling (Duck, P. (1990), Probe amplifier system based on chimeric cycling oligonucleotides, *Biotechniques* 9: 142-48; Modrusan, Z. (1998) Spermine-mediated improvement of cycling probe reaction, *Mol. Cell Probes* 12: 107-16). In this aspect of the present invention, the sequence-specific DNA-RNA-DNA nucleobase polymer used comprise at least one mobility-modifying polymer and at least one reporter molecule attached to either or both of the flanking DNA segments, thereby providing a labeled digestion product having a distinctive ratio of charge to translational frictional drag.

In another aspect, detection of selected nucleotide sequences within one or more target nucleic acids based on cleavage of a mobility-modified nucleobase polymer relies upon cleavage substrates formed by invasive hybridization, as described in Brow et al. U.S. Pat. No. 5,846,717. In this embodiment, the 5'-portion of a mobility-modified sequence-specific nucleobase polymer, which comprises a reporter molecule and which is hybridized to a target nucleic acid, is displaced by a second nucleobase polymer that hybridizes to the same region and thereby exposing that displaced sequence to cleavage with a cleaving reagent. In practicing the embodiment, the target nucleic acid is contacted with a mobility-modified sequence-specific nucleobase polymer and with a second nucleobase polymer. The mobility-modified sequence-specific nucleobase polymer has a 5'-segment complementary to a second region of the selected nucleotide sequence contained within a target nucleic acid and a 3'-portion complementary to a third region of the selected nucleotide sequence contained within a target nucleic acid, wherein the second region is downstream from the third region. The second nucleobase polymer has a 5'-segment complementary to a first region of the selected nucleotide sequence contained within a target nucleic acid and a 3'-segment complementary to the second region of the selected nucleotide sequence contained within a target nucleic acid, wherein the first region is downstream from the second region. Under selected conditions, hybrids form in which the mobility-modified sequenced specific nucleobase polymer and the second nucleobase polymer hybridize to the target polynucleotide such that the second nucleobase polymer displaces the 5' portion of the hybridized mobility-modified sequence-specific nucleobase polymer, whereas the 3' portion of the mobility-modified sequence-specific nucleobase polymer and the 5' portion of the second nucleobase polymer remain annealed to the selected nucleotide sequence contained within a target nucleic acid. The displaced strand, which is a single stranded segment that is not base-paired corresponds to the 5'-end of the mobility-modified sequence-specific nucleobase polymer then serves as a substrate for cleavage nucleases, thus producing discrete mobility-modified digestion products having distinct ratios of charge to translational frictional drag that reflect presence of specific sequences on the target polynucleotide.

Cleaving enzymes recognizing displaced strands are either naturally occurring nucleases or modified nucleases. Naturally occurring structure-specific nucleases include, but are not limited to *Pyrococcus woesii* FEN-1 endonuclease, thermostable *Methoanococcus jannaschii* FEN-1 endonucleases, yeast Rad2, and yeast Rad1/Rad10 complex (Kaiser et al., U.S. Pat. No. 6,090,606, Cleavage Reagents; Kaiser, et al. U.S. Pat. No. 5,843,669, Cleavage of nucleic acid using thermostable *Methoanococcus jannaschii* FEN-1 endonucleases). Other structure-specific enzymes suitable for the cleaving reaction are those derived from modifications of known nucleases and polymerases (Dahlberg et al., U.S. Pat No. 5,795,763, Synthesis Deficient Thermostable DNA Polymerase; Dahlberg et al., U.S. Pat No. 6,614,402, 5' Nucleases Derived from Thermostable DNA Polymerase). Modified polymerase that lack polymerase activity but still retain 5'-nuclease activity, are also used as cleaving reagents.

Another embodiment is directed toward the use of the mobility-modifying polymers of the present invention in "invader assays," which are SNP-identifying procedures based upon flap endonuclease cleavage of structures formed by two overlapping nucleobase polymers that hybridize to a target nucleic acid (see e.g. Cooksey et al., 2000, Antimicrobial Agents and Chemotherapy 44: 1296-1301). Such cleavage reactions release products corresponding to the 5'-terminal nucleobase(s) of the "downstream" nucleobase polymer. Where those cleavage products are labeled and can be separated from the uncleaved nucleobase polymer, an invader assay can be used to discriminate single base differences in, for example, genomic sequences or PCR-amplified genomic sequences.

Attachment of the mobility-modifying polymers of the present invention to the labeled 5'-terminus of the downstream nucleobase polymer used in an invader assay provides detectably-labeled cleavage products with distinctive charge to translational frictional drag ratios. Accordingly, a plurality of SNP's are analyzed simultaneously using a plurality of sequence-specific downstream nucleobase polymers, wherein the sequence-specific downstream nucleobase polymers comprise a mobility-modifying polymer of the present invention attached to the labeled 5'-terminus, such that the labeled product generated by flap endonuclease cleavage at each SNP has a distinctive charge to translational frictional drag ratio.

In a further aspect of the invader assay, for example, the downstream nucleobase polymer, which carries a label and a first mobility-modifying polymer of the present invention attached to the 5'-terminus, further comprises a second mobility-modifying polymer attached to the 3'-terminus. The presence of the second mobility-modifying polymer increases the sensitivity of the invader assay by enhancing the difference between the electrophoretic mobility of the flap endonuclease generated product, comprising the 5'-terminus, label, and first mobility-modifying polymer, and the electrophoretic mobility of the uncleaved downstream nucleobase polymer. Accordingly, the second mobility-modifying polymer has a molecular weight of at least 2000. In other embodiments, the second mobility-modifying polymer has a molecular weight of at least 5,000, at least 10,000, at least 20,000, and at least 100,000. In one embodiment, the second mobility-modifying polymer is a mobility-modifying polymer of the present invention, while in other embodiments, the second mobility-modifying polymer is a mobility-modifying polymer of the art, which is, in one illustrative, non-limiting example, an uncharged mono methyl polyethyleneglycol polymer. Moreover, the second mobility-modifying polymer may comprise a mixture of species of different molecular weight, provided that those species do not interfere substantially with detection of the signal product, i.e., the flap endonuclease generated product, comprising the 5'-terminus, label, and first mobility-modifying polymer (see Example 5, below).

More generally, in other embodiments of the present invention, invader assays are performed in which the downstream oligonucleobase polymer comprises a label and a mobility-modifying polymer of the present invention attached to a first region of the downstream oligonucleobase polymer, and a second, high-molecular weight mobility-modifying polymer attached to a second region of the downstream oligonucleobase polymer, wherein first and second regions are separated by the flap endonuclease cleavage site. One aspect of this embodiment is described above and in Example 5, wherein the label and mobility-modifying polymer of the present invention are attached to the 5'-end of the sequence-specific oligonucleobase polymer and a second, high molecular weight mobility-modifying polymer is attached to the 3'-end of the sequence-specific oligonucleobase polymer. In other embodiments, for example, a second, high molecular weight mobility-modifying polymer is attached, via a linker arm nucleotide residue, to the sequence-specific nucleobase polymer, rather than at the 5'-end or 3'-end of the sequence-specific nucleobase polymer. Accordingly, the second, high molecular weight mobility-modifying polymer, is attached at any nucleobase residue within the second region of the downstream nucleobase polymer, or to the 5'-end or 3'-end, whichever is included within the second region of the downstream oligonucleobase polymer. Similarly, in some embodiments, the label, which is a fluorescent dye in certain non-limiting examples, is also attached via a linker arm nucleotide residue at any nucleobase residue within the first region of the downstream nucleobase polymer. Synthesis of such linker arm nucleotides and the coupling of, inter alia, a fluorescent dye or an uncharged mono methyl polyethyleneglycol polymer to the linker, are within the scope of the art (see e.g., Section 4.5 above). Moreover, e.g., linker arm nucleoside phosphoramidite monomers, as well as linker arm nucleoside phosphoramidite monomers comprising flourescent moieties, are commercially available (Glen Research, Inc., Sterling, Va.). In these embodiments, the mobility-modifying polymer of the present invention is attached to the first region of the downstream nucleobase polymer, where the point of attachment may be at the 5'-end or the 3'-end, whichever is encompassed within the first region of the downstream nucleobase polymer, or the mobility-modifying polymer of the present invention may be incorporated within the first region of the downstream nucleobase polymer, providing a molecule according to Structural formula (IV). Therefore, in each of these embodiments, the presence of the second high molecular weight mobility-modifying polymer attached to the second region of the downstream nucleobase polymer increases the sensitivity of the invader assay by enhancing the difference between the electrophoretic mobility of the flap endonuclease generated product comprising a label and a mobility-modifying polymer of the present invention, i.e., the first region of the downstream oligonucleobase polymer, and the electrophoretic mobility of the uncleaved downstream nucleobase polymer.

In a still further embodiment of an invader assay, the downstream nucleobase polymer carries a label and a first mobility-modifying polymer, which is in one non-limiting embodiment, a standard PEO mobility-modifying polymer of the art, that is attached to the first region of the downstream nucleobase polymer, and a second, high molecular weight mobility-modifying polymer attached to the second region of the downstream nucleobase polymer. As above, the presence of the second mobility-modifying polymer increases the sensitivity of the invader assay by enhancing the difference between the electrophoretic mobility of the flap endonuclease generated product, i.e., the first region of the downstream nucleobase polymer, which comprises a label and a first mobility-modifying polymer, and the electrophoretic mobility of the uncleaved downstream nucleobase polymer. Accordingly, the second mobility-modifying polymer has a molecular weight of at least 2000. In other embodiments, the second mobility-modifying polymer has a molecular weight of at least 5,000, at least 10,000, at least 20,000, and at least 100,000. In one embodiment, the second mobility-modifying polymer is a mobility-modifying polymer of the present invention, while in other embodiments, the second mobility-modifying polymer is a mobility-modifying polymer of the art, which is, in one illustrative, non-limiting example, an uncharged mono methyl polyethyleneglycol polymer.

In another aspect of the present invention, the mobility-modified sequence-specific nucleobase polymer serves as a cleavage substrate in detection reactions involving multiple sequential cleavage reactions, as described in Hall, J. G. et al., U.S. Pat. No. 5,994,069. In this embodiment, a first cleavage structure is formed as set forth above, except that in the present embodiment, the first nucleobase polymer is optionally a mobility-modified sequence-specific nucleobase polymer. The reaction mixture further includes a second target nucleic acid and a third nucleobase polymer, which is a mobility-modified sequence-specific nucleobase polymer, and further comprises at least one attached reporter molecule. The second target polynucleotide has a first, a second and a third region, wherein the first region is downstream of the second region, and the second region is downstream of the third region. The third nucleobase polymer has a 5' portion fully complementary to the second region of the second target polynucleotide and a 3' portion fully complementary to the third region of the second target polynucleotide. Treatment of the first cleavage structure results in release of a fourth nucleobase polymer, which has a 5' portion complementary to the first region of the second target polynucleotide and a 3' portion fully complementary to the second region of the second target polynucleotide. This released fourth nucleobase polymer forms a cleavage structure with the second target polynucleotide and the third nucleobase polymer under conditions where the 3' portion of the third nucleobase polymer and the 5' portion of the fourth nucleobase polymer remains annealed to the second target polynucleotide. Cleavage of the third nucleobase polymer with a cleavage reagent generates a fifth and sixth nucleobase polymer, either or both of which comprise a reporter molecule and a mobility-modifying polymer, thereby providing a digestion product having a distinctive ratio of charge to translational frictional drag. The fifth nucleobase polymer is released upon cleavage, while the sixth nucleobase polymer remains hybridized to the second target polynucleotide until dissociated by denaturation. Subsequent separation and detection of the fifth or sixth nucleobase polymer provides information about the presence of the first and second selected nucleotide sequence within the target nucleic acid.

In a further aspect of the present invention relating to a nucleotide sequence detection method involving multiple sequential cleavage reactions, a first cleavage structure is formed by first and second nucleobase polymer and a selected nucleotide sequence within a target nucleic acid, as set forth above. This aspect of the method further comprises a mobility-modified sequence-specific second target nucleobase polymer, which has a first, a second, and a third region, wherein the first region is downstream of the second region, and wherein the third region upstream of the second region, is fully self complementary and also complementary to the second region, such that it forms a hairpin structure under selected conditions. Cleavage of the first cleavage structure with a cleaving reagent generates a fourth nucleobase polymer, which has a 5'-portion complementary to the first region and a 3'-portion fully complementary to the second region of the nucleobase polymer. Hybridization of the released fourth nucleobase polymer to the first and second regions of the mobility-modified sequence-specific nucleobase polymer forms a second cleavage structure with a displaced third region that is complementary to the second region. Cleavage of this second cleavage structure generates a fifth and sixth nucleobase polymers, either of which comprises a mobility-modifying polymer and a label, thereby providing s digestion product having a distinctive ratio of charge to translational frictional drag, and whose separation and detection provides information about the presence of the first target nucleic acid and the second nucleobase polymer.

Methods for labeling and detecting the cleaved nucleobase polymers, as set forth infra., are equally applicable to the labeling and detection of products of the cleavage reactions. Moreover, labeling of released cleavage products is also accomplished by extension of the product by template independent polymerases, including but not limited to terminal transferase and polyA polymerase as described in U.S. Pat No. 6,090,606, which is hereby specifically incorporated by reference.

In yet another aspect, the mobility-modified sequence-specific nucleobase polymers of the present invention are employed within a general method to effect the electrophoretic separation of target nucleic acids of different sizes in non-sieving media. Normally, nucleic acids of different length, i.e. consisting of different numbers of nucleobase residues, nevertheless display an essentially invariant ratio of charge to translational frictional drag. Accordingly, such molecules cannot be separated electrophoretically in non-sieving media. However, attachment of a mobility-modified sequence-specific nucleobase polymer of the present invention to target nucleic acids of different length alters their ratio of charge to translational frictional drag of the target nucleic acids in a manner and to a degree sufficient to effect their electrophoretic separation in non-sieving media. Furthermore, and in contrast to electrophoretic separations in sieving media, longer nucleic acids to which a mobility-modified sequence-specific nucleobase polymer of the present invention has been attached will migrate more rapidly than a shorter nucleic acid to which the same mobility-modified sequence-specific nucleobase polymer has been attached. Applicants believe, although without wishing to be held to that belief, that such separations are based upon the proportionately smaller effect of attachment of a mobility-modifying sequence-specific nucleobase polymer of defined mass and size to a longer chain nucleic acid molecule than to a shorter chain nucleic acid molecule. Consequently, the ratio of charge to frictional translational drag will be greater for the longer chain, providing the longer chain nucleic acid with a greater velocity in an electric field.

Attachment of a mobility-modified sequence-specific nucleobase polymers selected from the group consisting of Structural formulae (II) and (III) to a population of nucleic acids of different length can be accomplished using a variety of approaches, including but not limited to enzymatic ligation or direct, synthetic incorporation of the mobility-modifying sequence-specific nucleobase polymers of the present invention into the population of nucleic acids of different lengths that are to be separated.

In one aspect of this method, a mobility-modifying sequence-specific nucleobase polymer is enzymatically ligated to a population of nucleic acids of different length but having a common nucleotide sequence at the 5'-end, as is seen within the products of a chain termination nucleic acid sequencing reaction or, effectively, in chemical cleavage sequencing reactions which are transparent to all sequences other than those comprising the labeled 5'-end of the nucleic acid substrate. In this embodiment a synthetic template oligonucleotide, having two distinct sequence regions would be used as a template to align the hybridized 3'-end of a mobility-modifying sequence-specific nucleobase polymer so that it would directly abut the hybridized 5'-end, which is generally phosphorylated, that is common to the population of nucleic acids to be separated, and permit the two molecules to be covalently joined. Therefore the 5'-region of the synthetic template oligonucleotide would consist of a nucleotide sequence complementary to the common 5'-end sequence of the molecules to be separated, while the 3'-region of the synthetic template would consist of sequences complementary to the 3'-end of the mobility-modifying sequence-specific nucleobase polymer to be joined. In another embodiment of this approach, the common 5'-end of the population of nucleic acids to be separated corresponds to that generated by a sequence-specific restriction endonuclease. Therefore the synthetic template nucleic acid consists of at least eight nucleobases, of which at least three would be complementary to a common 5'-sequence of the population of molecules to be separated. The design of such template nucleic acids, as well as the conditions under which the enzymatic joining of the hybridized target nucleic acid and the mobility-modified sequence-specific nucleobase polymer would be carried out, are well known to those of ordinary skill in the art. Accordingly, this embodiment of the invention is applicable to any population of molecules of different sizes, provided each has a common 5'-end sequence of at least three nucleotides, in certain embodiments, at least four nucleotides, and in further embodiments, at least eight nucleotides. Similar procedures, wherein the sequence common to a population of molecules of different sizes occurs at the 3'-end, and consequently, the mobility-modifying sequence-specific nucleic to be attached has a phosphorylated 5'-end with the mobility-modifying polymer attached to the 3'-end, are also included within the scope of the present invention.

In a further embodiment, a mobility-modifying sequence-specific nucleobase polymer is synthesized so as to be complementary to a nucleotide sequence within, for example, a sequencing vector, that is upstream of, i.e. toward the 5'-end of, the binding site of a sequencing primer used in Sanger, enzymatic chain termination sequencing reaction. In this embodiment, the mobility-modified sequence-specific nucleobase polymer is enzymatically ligated to the sequencing primer either before or after extension of the sequencing primer during a chain termination sequencing reaction. In this embodiment, the mobility-modified sequence-specific nucleic acid is synthesized so that, once hybridized to the template polynucleotide, its 3'-end would either directly abut the 5'-end of the hybridized sequencing primer, or that 3'-end would hybridize to sequences upstream of the 5'-end of the sequencing primer. In the latter instance, the resulting gap is filled with a nucleic acid polymerase and the extended molecule is then enzymatically ligated to the sequencing primer.

Another embodiment of the invention is related to the separation and detection of mobility-modified sequence-specific nucleobase polymers and polynucleotides. Separation of oligonucleotides is effected by electrophoresis, chromatography, or mass spectroscopy. In methods employing electrophoresis, the format may be thin flat chambers. In another embodiment, the separation is carried out by electrophoresis in capillary tubes. The advantage of capillary electrophoresis is efficient heat dissipation, which increases resolution and permits rapid separation under high electrical fields. Moreover, the small diameters of the capillary tubes allow separation of numerous samples in arrays of capillaries.

Sieving or nonsieving media are applicable to separation of mobility-modified nucleobase polymers including but not limited to the reaction products generated in the detection methods disclosed herein. Sieving media include covalently crosslinked matrices, such as polyacrylamide crosslinked with bis-acrylamide (see e.g. Cohen, A. S. et al. (1988) Rapid separation and purification of oligonucleotides by high performance capillary gel electrophoresis, *Proc. Natl Acad. Sci USA* 85: 9660; Swerdlow, H. et al., (1990), Capillary gel electrophoresis for rapid, high resolution DNA sequencing, *Nuc. Acids Res.* 18 (6): 1415-1419) or linear polymers, for example hydroxypropylmethylcellulose, methyl cellulose, or hydroxylethylcellulose (Zhu et al. (1992), *J. Chromatogr.* 480: 311-319; Nathakarnkitkool, S., et al. (1992), *Electrophoresis* 13: 18-31).

In one embodiment, the electrophoretic medium is a non-sieving medium. Although polynucleotides are not readily separable in a non-sieving medium, mobility-modified nucleobase polymers and polynucleotides have distinctive ratios of charge to translational frictional drag that permit separation in a non-sieving media, even when the nucleobase polymer and polynucleotides are of the same length.

5.7 KITS

Kits of the invention comprise one or more mobility-modified sequence-specific nucleobase polymers. The kits may also comprise a second nucleobase polymer, typically an oligonucleotide, which is optionally mobility-modified, where the intended assay requires a second oligonucleotide; for example, kits for oligonucleotide ligation assays and PCR analysis. Similarly, kits designed for ligase chain reaction amplification will further comprise at least two additional nucleobase polymers, which together are complementary to a diagnostic ligase reaction product. The kits further may also comprise treating reagents such as restriction enzymes, DNA polymerases, RNases, mismatch binding proteins, ligases, and exonucleases. Primer extension kits appropriate for sequencing or oligonucleotide extension assays for detecting single nucleotide polymorphisms, may further comprise nucleoside triphosphates and/or chain terminating nucleotides. The kit may also comprise reaction buffers for carrying out hybridizations and enzymatic treatments.

The invention further comprises kits comprising one or more of the mobility-modifying phosphoramidite reagents of present invention. One or more of the mobility-modifying phosphoramidite reagents, in such kits, may further comprise one or more protecting groups, reporter molecules, or ligands. Such kits may also comprise one or more solvents, reagents, or solid surface-bound nucleobase materials for use in the synthesis of mobility-modified sequence specific nucleobase polymers.

6. EXAMPLES

The following examples serve to illustrate certain preferred embodiments and aspects of the present invention and are not to be construed as limiting the scope thereof.

Example 1

Synthesis of DMT-Protected Poly(ethylene oxide) Alkyl Phosphoramidite

Bis(diisopropylamino)chlorophosphine was synthesized by reacting phosphorous trichloride and diisopropylamine in toluene. Fifty ml of the resulting bis(diisopropylamino)phosphine was placed in a 250 ml flask and 3.01 ml of ethanol added slowly over a two minute period and the reaction allowed to proceed for several days. After filtering the mixture and removing the solvent, the structure of the bis(diisopropylamino)ethylphosphite ester reagent was analyzed by $^{31}P$ and $^1H$ NMR ($^{31}P$ NMR in $CD_3CN$ 125.9 ppm).

Mono dimethoxytrityl (DMT) protected pentaethylene oxide (3.0 gm, 5.5 mmole) tetrazole diisopropylamine salt (0.095 gm, 0.055 mmole) were dissolved in 10 ml of methylene chloride and reacted with bis(diisopropylamino)ethylphosphite ester (1.75 gm, 7.2 mmole) for 15 hours. The phosphoramidite product, DMT-pentaethyleneoxide ethyl-N,N-diisopropylphosphoramidite, was washed two times with saturated $NaHCO_3$ solution, followed by a third wash with saturated NaCl solution and dried over $Na_2SO_4$ The solution was basified by addition of triethylamine (TEA) (100 µl), and the solvent was removed. Recovered crude (4.2 gm) was purified using silica gel chromatography, yielding 2.8 gm product ($^{31}P$ NMR in $CD_3CN$ 145.3 ppm). To synthesize mobility-modifying phosphoramidite reagents lacking the ethyl ester, DMT protected tetraethylene oxide was reacted with β-cyanoethyl chloro N,N-diisopropylaminophosphite under standard conditions (see e.g. Levenson. C., et al., U.S. Pat. No. 4,914,210).

Example 2

Synthesis of Mobility-Modified Sequence-Specific Nucleobase Polymers

Sequence-specific nucleobase polymers labeled at the 3'-nucleoside with tetramethyl rhodamine were synthesized on a Applied Biosystems 394 synthesizer using standard phosphoramidite chemistry. To synthesize mobility-modifying nucleobase polymers, the phosphoramidite reagents of Example 1 were reacted with the 5' OH end of the immobilized nucleobase polymer. Subsequent oxidation with iodine and deprotection with base converts β-cyanoethylphosphite linkages to phosphate diester linkages while ethyl phosphite linkages are converted to ethyl phosphate triester linkages. After cleavage from the solid support and deprotection with base at 55° C. for 4 hrs, the nucleobase polymers were purified by high performance liquid chromatography (HPLC). Treatment with 100 µl of 80% acetic acid for 15 min removed the final DMT protecting group. The mobility-modified nucleobase polymers were purified on a PD 10 column.

Example 3

Separation Characteristics of Mobility-Modified Sequence-Specific Nucleobase Polymers A series of twelve-residue nucleobase polymers ("12 mers") were synthesized to which were attached different mobility-modifying monomeric units of pentaethylene oxide via either charged phosphate diester (PEO) or uncharged ethyl phosphate triester (PEE) linkages, which were synthesized as set forth in Example 2. The relative electrophoretic mobility profile for each compound was evaluated by separation by capillary electrophoresis in a non-sieving medium (Applied Biosystems 310 Genetic Analyzer). Fluorescent internal size standards provided the reference markers for peak retention analysis using GeneScan® software.

An unmodified 12-mer nucleobase polymer migrates with an apparent base size of 24.7. Attachment of three units of pentaethylene oxide covalently linked to the nucleobase polymer moiety through negatively charged phosphate diester linkages, retards the mobility of the 12 mer by 5.3 bases, while modification with only a single monomeric unit of pentaethylene oxide attached through an uncharged ethyl phosphate triester linkage retards the mobility by 8.3 bases. Furthermore, the attachment of additional pentaethylene oxide units linked through uncharged ethyl phosphate triester linkages produces non-linear decreases in mobility of the oligonucleotide.

TABLE 1

| Oligonucleotide: 3' TMRA labeled 12 mer | Mobility (base size) | Mobility change relative to unmodified oligonucleotide |
|---|---|---|
| 5' OH | 24.7 | — |
| 5' (PEO)$_3$ | 30.0 | 5.3 |
| 5' (PEE)$_1$ | 33.0 | 8.3 |
| 5' (PEE)$_3$ | 60.0 | 35.3 |
| 5' (PEE)$_6$ | 116.0 | 91.3 |

TMRA: carboxytetramethylrhodamine
PEO: phosphate diester linked pentaethylene oxide
PEE: ethyl phosphate triester linked pentaethylene oxide Example 4

Analysis of Synthetic Modified Oligonucleotide Products of Invader Assay

The SNP-identifying procedure generally referred to as an invader assay is based upon flap endonuclease cleavage of structures formed by two overlapping oligonucleotides that hybridize to a target nucleic acid (see erg. Cooksey et al., 2000, Antimicrobial Agents and Chemotherapy 44: 1296-1301). Such cleavage reactions release products corresponding to the 5'-terminal nucleotide or 5'-terminal oligonucleotide of the downstream oligonucleotide. Where those cleavage products are labeled and can be separated from the uncleaved oligonucleotide, the invader assay can be used to discriminate single base differences in, for example, genomic or PCR-amplified genomic sequences.

In order to demonstrate the utility of the mobility-modifying polymer segments of the present invention for use, e.g., in invader assays, the compounds of Table 2, which represent exemplary reaction products that could be generated within an invader assay, were synthesized using methods disclosed supra. Each of the compounds of Table 2 was labeled at the 5'-end with a fluorescent dye as indicator. The relative mobility of each of these compounds was determined by capillary electrophoresis using all Applied Biosystems instrument, model number 310, and data analysis was performed using GeneScan software, version 2.1fc4.

TABLE 2

| Oligonucleotide: 5' FAM labeled | Mobility (base size) | Mobility change relative to unmodified oligonucleotide |
|---|---|---|
| G | 39.6 | — |
| 5' (PEO)$_1$-(PEE)$_1$ | 75.5 | 35.9 |
| 5' (PEE)$_1$ | 95.1 | 55.5 |
| 5' (PEO)$_2$-(PEE)$_1$ | 65.5 | 25.9 |
| 5' (PEE)$_3$ | 250 | 210.4 |
| 5' (PEE)$_2$ | 160 | 120.4 |
| 5' (PEO)$_2$-(PEE)$_2$ | 104 | 64.4 |
| 5' (PEE)$_{10}$ | 1300 | 1260 |

FAM: carboxyfluorescein
PEO: phosphate diester linked pentaethylene oxide
PEE: ethyl phosphate triester linked pentaethylene oxide The data in Table 2 demonstrate the unexpectedly large effect on mobility provided by the mobility-modifying polymer segments of the present invention, especially in comparison to the phosphate diester linked pentaethylene oxide monomers of the art. The data of Table 2 further demonstrate the extent of electrophoretic separation that can be obtained using the mobility-modifying phosphoramidite functionalizing reagents of the present invention. Moreover, the data of Table 2 also demonstrate that compounds of intermediate mobility are obtained by combining the mobility-modifying phosphoramidite functionalizing reagents of the present invention with, as a non-limiting example, phosphate diester linked pentaethylene oxide monomers of the art.

Example 5

Analysis of Cleaved Modified Oligonucleotide Products of Invader Assay

An invader assay probe is synthesized that comprises a fluorescent dye (FAM) coupled to a first mobility-modifying polymer, a dimer of a mobility-modifying phosphoramidite funetionalizing reagent of the present invention ((PEE).sub.2), linked to the following oligonucleotide: 5'-GG-GACGGGGTTCAGC-3'-NH$_2$, (SEQ ID NO:4) using standard DNA synthesis methods and PEE phosphoramidite reagents. After cleavage from the support and deprotection with base at 55E C for 4 hours, the oligonucleotide is purified by HPLC. The oligonucleotide: 5'-FAM-(PEE)$_2$-GG-GACGGGGTTCAGC-3'-NH$_2$ (SEQ ID NO:5) is dissolved in water, coupled with a second mobililty-modifying polymer, mono-methyl polyethylene glycol 5000 propionic acid N-succinimidyl ester (Fluka) in the presence of NaHCO$_3$ for two hours, and purified by HPLC, yielding the derivatived, mobility-modified product 5'-FAM-(PEE)$_2$-GGGACGGGGTTCAGC-3'-PEG 5000 (SEQ ID NO:6).

The invader assay is performed using, as template, a 527 by PCR product generated by amplification of a segment of human genomic DNA corresponding to the TNF-α gene, using the following PCR primers: 5'-GAGTCTCCGGGT-CAGAATGA (SEQ ID NO:7) (forward) and 5'- TCTCG-GTTTCTTCTCCATCG (SEQ ID NO:8) (reverse). In the first step of the invader assay, approximately 0.2 pmole of the PCR product is denatured at 95E C for 5 min. in the presence of 0.5 pmole of invading probe (5'-GAGGCAAT-AGTITTTGAGGGGCATGT) (SEQ ID NO:9). In the second step, 50 ng of Cleavase VII is added along with 10 pmole of 5'-mobility-modified oligonucleobase probe, 5'-FAM-(PEE)$_2$-GGGACGOGGTTCAGC-3'-PEG 5000 (SEQ ID NO:10), in a total reaction volume of 10 µl further comprising 10 mM MOPS, pH 8.0, 7.5 mM MgCl$_2$, 0.05% Tween 20, and 0.05% Nonidet P40. The invader assay is incubated for 15 hours at 66E C. The reaction is terminated and a 1 µl aliquot thereof is electrophoresed on an Applied Biosystems instrument, model number 310, with data analysis performed using GeneScan software, version 2.1fc4. Analysis of the results demonstrates the presence of the cleavage product 5'-FAM-(PEE)$_2$-G, which is well separated from the uncleaved probe, 5'-FAM-(PEE)$_2$- GGGACGGGGTTCAGC-3'-PEG 5000 (SEQ ID NO:11). The uncleaved probe was detected as a plurality of closely-spaced peaks arising from the plurality of molecular weight species included within the commercially-available mono methyl polyethylene glycol polymer product attached to the 3'-end of the labeled probe, 5'-FAM-(PEE)$_2$-GGGACGGGGTTCAGC-3' (SEQ ID NO:12) as the second mobility-modifying polymer.

All publications and patents referred to herein are hereby incorporated by reference in their entirety. As recognized by those skilled in the art of molecular biology, the use of mobility-modified sequence-specific nucleobase polymers are adaptable to a variety of methods. Various modifications and variations of the above described method and composition will be apparent to those skilled in the art without departing from the spirit and scope of the invention. As a specific example, although various embodiments of the invention may be descriptively exemplified with DNA or RNA oligonucleotides, skilled artisans will recognize that the described embodiments may also work with other nucleobase polymers, including analogs and derivatives of RNA and DNA oligonucleotides. Although specific preferred embodiments of the claims are described, the invention as claimed should not be limited to the specific embodiments. Various modification of the described modes which are obvious to those skilled in the art are intended to be within the scope of the following claims.

What is claimed is:

1. A mobility-modified sequence-specific nucleobase polymer comprising a mobility-modifying polymer linked to a sequence-specific nucleobase polymer, according to Structural formula (II) or (III):

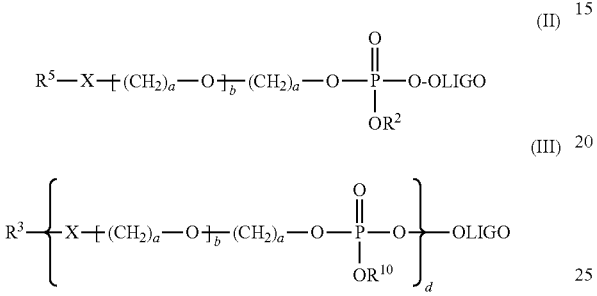

or a salt thereof, wherein:
  $R^2$ is selected from the group consisting of alkyl comprising at least two carbon atoms, aryl, $(R^8)_3$Si— where each $R^8$ is independently selected from the group consisting of linear and branched chain alkyl and aryl, base-stable protecting groups, and $R^5$—X—[(CH$_2$)$_a$—O]$_b$—(CH$_2$)$_a$—;
  each $R^{10}$ is independently selected from the group consisting of hydrogen and $R^2$;
  $R^5$ is selected from the group consisting of hydrogen, protecting group, reporter molecule, and ligand;

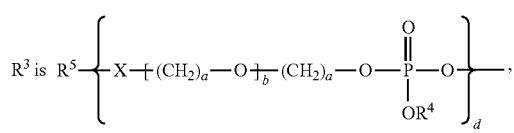

each $R^4$ is independently selected from the group consisting of hydrogen and $R^2$;
  each X is O;
  each a is independently an integer from 1 to 6;
  each b is independently an integer from 0 to 40;
  each d is independently an integer from 1 to 200; and
  OLIGO is a sequence-specific nucleobase polymer, with the proviso that at least one $R^{10}$ or at least one $R^4$ is other than hydrogen.

2. The mobility-modified sequence-specific nucleobase polymer of claim 1 in which each a is 2.

3. The mobility-modified sequence-specific nucleobase polymer of claim 2 in which each b is 4.

4. A method for detecting a plurality of selected nucleotide sequences within one or more target nucleic acids, comprising:
  a) contacting the target nucleic acids with a plurality of nucleobase polymer primers whereby a first nucleobase polymer primer and a second nucleobase polymer primer each hybridize to complementary strands and at opposite ends of each of a plurality of selected nucleotide sequences, wherein at least one of each said first nucleobase polymer primer and said second nucleobase polymer primer is a mobility-modified sequence-specific nucleobase polymer according to claim 2;
  b) extending each said first nucleobase polymer primer and each said second nucleobase polymer primer with a DNA polymerizing activity in the presence deoxyribonucleoside triphosphate substrates;
  c) denaturing the plurality of base-paired structures formed by base pairing interactions between each extended first nucleobase polymer primer and the target nucleic acid and each extended second nucleobase polymer primer and the target nucleic acid;
  d) repeating steps (a) through (c) a plurality of times to form a plurality of polymerase chain reaction products, wherein each said polymerase chain reaction product has a distinctive ratio of charge to translational frictional drag; and
  e) detecting said polymerase chain reaction products.

5. The mobility-modified sequence-specific nucleobase polymer of claim 1 in which OLIGO is a DNA, RNA, DNA analog, or RNA analog oligonucleotide.

6. The mobility-modified sequence-specific nucleobase polymer of claim 1 in which OLIGO is an analog of a DNA or RNA oligonucleotide.

7. The mobility-modified sequence-specific nucleobase polymer of claim 1 in which OLIGO comprises at least one non-negatively charged internucleotide linkage.

8. The mobility-modified sequence-specific nucleobase polymer of claim 7, wherein said internucleotide linkage is a mono alkyl phosphate triester.

9. The mobility-modified sequence-specific nucleobase polymer of claim 1 in which $R^5$ is a reporter molecule.

10. The mobility-modified sequence-specific nucleobase polymer of claim 9 in which the reporter molecule is a fluorophore, a chemiluminescent moiety, or a ligand.

11. A composition comprising a plurality of mobility-modified sequence-specific nucleobase polymers, wherein each said nucleobase polymer is a compound according to claim 1, and wherein each said nucleobase polymer has a distinctive ratio of charge to translational frictional drag.

12. The composition of claim 11, wherein said each mobility-modified sequence-specific nucleobase polymer of said plurality comprises an OLIGO, and wherein each OLIGO has the same number of nucleobase units.

13. A method for detecting a plurality of selected nucleotide sequences within one or more target nucleic acids, comprising:
  contacting at least one or more target nucleic acids with a plurality of mobility-modified sequence-specific nucleobase polymers under conditions that distinguish those nucleobase polymers that hybridize to the target nucleic acid, wherein each said nucleobase polymer is a compound according to claim 1, and wherein each said nucleobase polymer has a distinctive ratio of charge to translational frictional drag; and detecting those nucleobase polymer that have hybridized to the target nucleic acid.

14. A method for detecting a plurality of selected nucleotide sequences within one or more target nucleic acids, comprising:
   contacting the target nucleic acids with a first plurality of mobility-modified sequence-specific nucleobase polymer probes and a second plurality of sequence-specific nucleobase polymer probes under conditions that distinguish between those probes that hybridize to the target nucleic acids, wherein each mobility-modified sequence-specific nucleobase polymer is a compound according to claim 1 and has a distinctive ratio of charge to translational frictional drag;
   covalently joining first and second probes that adjacently hybridize to the same target nucleic acid molecules to form a ligation product, wherein each said ligation product has a distinctive ratio of charge to translational frictional drag; and
   detecting said ligation products.

15. A method of separating a plurality of target nucleic acid molecules, comprising:
   attaching a mobility-modified sequence-specific nucleobase polymer according to claim 1 to each target nucleic acid of the plurality, thereby forming a plurality of mobility-modified target nucleic acids, wherein each target nucleic acid having the same number of nucleotide residues has a distinctive ratio of charge to translational frictional drag; and
   fractionating the plurality of mobility-modified target nucleic acids.

16. A kit comprising at least one mobility-modified sequence specific nucleobase polymer, wherein the mobility-modified sequence specific nucleobase polymer comprises a mobility-modifying polymer linked to a sequence-specific nucleobase polymer, according to structural formula (II) or (III):

$$R^5-X + (CH_2)_a - O +_b (CH_2)_a - O - \overset{O}{\underset{OR^2}{P}} - O\text{-OLIGO} \quad (II)$$

$$R^3 + \left[ X + (CH_2)_a - O +_b (CH_2)_a - O - \overset{O}{\underset{OR^{10}}{P}} - O \right]_d \text{-OLIGO} \quad (III)$$

or a salt thereof, wherein:
   $R^2$ is selected from the group consisting of alkyl comprising at least two carbon atoms, aryl, $(R^8)_3$ Si—where each $R^8$ is independently selected from the group consisting of linear and branched chain alkyl and aryl, base-stable protecting groups, and $R^5-X-[(CH_2)_a-O]_b-(CH_2)_a-$;
   $R^5$ is selected from the group consisting of hydrogen, protecting group, reporter molecule, and ligand;

$$R^3 \text{ is } R^5 + \left[ X + (CH_2)_a - O +_b (CH_2)_a - O - \overset{O}{\underset{OR^4}{P}} - O \right]_d;$$

each $R^{10}$ is independently selected from the group consisting of hydrogen and $R^2$;
each $R^4$ is independently selected from the group consisting of hydrogen and $R^2$;
each X is independently selected from the group consisting of O, S, NH and NH—C(O);
each a is independently an integer from 1 to 6;
each b is independently an integer from 0 to 40;
each d is independently an integer from 1 to 200; and
OLIGO is a sequence-specific nucleobase polymer, with the proviso that at least one $R^{10}$ or at least one $R^4$ is not hydrogen.

17. The kit of claim 16 wherein the mobility-modifying polymer linked to a sequence-specific nucleobase polymer according to structural formula (II) or (III) is the compound wherein X is O.

18. The kit of claim 16 wherein the mobility-modifying polymer linked to a sequence-specific nucleobase polymer according to structural formula (II) or (III) is the compound wherein each a is 2.

19. The kit of claim 16 wherein the mobility-modifying polymer linked to a sequence-specific nucleobase polymer according to structural formula (II) or (III) is the compound wherein each b is 4.

20. The kit of claim 16 wherein the mobility-modifying polymer linked to a sequence-specific nucleobase polymer according to structural formula (II) or (III) is the compound wherein OLIGO is a DNA, RNA, DNA analog, or RNA analog oligonucleotide.

21. The kit of claim 20 wherein OLIGO is an analog of a DNA or RNA oligonucleotide.

22. The kit of claim 16 wherein the mobility-modifying polymer linked to a sequence-specific nucleobase polymer according to structural formula (II) or (III) is the compound wherein OLIGO comprises at least one non-negatively charged internucleotide linkage.

23. The kit of claim 22 wherein the internucleotide linkage is a mono alkyl phosphate triester.

24. The kit of claim 16 wherein the mobility-modifying polymer linked to a sequence-specific nucleobase polymer according to structural formula (II) or (III) is the compound wherein $R^5$ is a reporter molecule.

25. The kit of claim 24 wherein the reporter molecule is a fluorophore, a chemiluminescent moiety, or a ligand.

26. The kit of claim 16 further comprising a second nucleobase polymer wherein the second nucleobase polymer is optionally mobility-modified according to structural formula (II) or (III).

27. The kit of claim 26 wherein the second nucleobase polymer is an oligonucleotide.

28. The kit of claim 16 comprising a plurality of mobility-modified sequence-specific nucleobase polymers according to structural formula (II) or (III), and wherein each mobility-modified sequence-specific nucleobase polymer has a distinctive ratio of charge to translational frictional drag.

29. The composition of claim 28, wherein each mobility-modified sequence-specific nucleobase polymer of the plurality of mobility-modified sequence-specific nucleobase polymers according to structural formula (II) or (III) comprises an OLIGO, and wherein each OLIGO has the same number of nucleobase units.

30. The kit of claim 16 further comprising one or more reagents selected from restriction enzymes, DNA polymerases, RNAses, mismatch binding proteins, ligases, exonucleases, and a combination thereof.

31. The kit of claim 16 further comprising one or more reagents selected from nucleoside triphosphates, chain terminating nucleotides, and a combination thereof.

32. The kit of claim 16 further comprising one or more reaction buffers configured for use in hybridizations or enzymatic treatments.

\* \* \* \* \*